(12) United States Patent
Babu et al.

(10) Patent No.: US 8,440,813 B2
(45) Date of Patent: *May 14, 2013

(54) ANTIVIRAL NUCLEOSIDE ANALOGS

(75) Inventors: Yarlagadda S. Babu, Birmingham, AL (US); Pooran Chand, Birmingham, AL (US); V. Satish Kumar, Birmingham, AL (US); Pravin L. Kotian, Birmingham, AL (US); Minwan Wu, Birmingham, AL (US)

(73) Assignee: BioCryst Pharmaceuticals, Inc., Durham, NC (US)

( * ) Notice: Subject to any disclaimer, the term of this patent is extended or adjusted under 35 U.S.C. 154(b) by 560 days.

This patent is subject to a terminal disclaimer.

(21) Appl. No.: 12/522,892

(22) PCT Filed: Jan. 11, 2008

(86) PCT No.: PCT/US2008/050929
§ 371 (c)(1),
(2), (4) Date: Jul. 30, 2009

(87) PCT Pub. No.: WO2008/089105
PCT Pub. Date: Jul. 24, 2008

(65) Prior Publication Data
US 2010/0015094 A1    Jan. 21, 2010

Related U.S. Application Data

(60) Provisional application No. 60/880,278, filed on Jan. 12, 2007.

(51) Int. Cl.
C07H 5/04    (2006.01)
C07D 253/10    (2006.01)
A61K 31/7052    (2006.01)

(52) U.S. Cl.
USPC .......................... 536/29.2; 544/183; 514/243

(58) Field of Classification Search .................. 544/183; 514/243; 536/29.2
See application file for complete search history.

(56) References Cited

U.S. PATENT DOCUMENTS

| | | | | |
|---|---|---|---|---|
| 6,812,219 B2 * | 11/2004 | LaColla et al. | .................. | 514/49 |
| 7,994,139 B2 * | 8/2011 | Babu et al. | ....................... | 514/23 |
| 8,119,607 B2 | 2/2012 | Francom et al. | | |
| 2007/0032448 A1 * | 2/2007 | Hong et al. | ....................... | 514/45 |
| 2010/0035836 A1 | 2/2010 | Francom et al. | | |

FOREIGN PATENT DOCUMENTS

WO    WO-2010/002877 A2    1/2010

OTHER PUBLICATIONS

Wolff, Manfred E. "Burger's Medicinal Chemistry, 5ed, Part 1", John Wiley & Sons, 1995, pp. 975-977.*
Banker, G.S. et al, "Modern Pharmaceutics, 3ed.", Marcel Dekker, New York. 1996, pp. 451 and 596.*
Patil, S.A. et al.,Tetrahedron Letters, vol. 35, 1994, pp. 5339-5342(Abstract provided).*
Kwong, A.D. et al., Current Opinion in Pharmacology 2008, 8:522-531.*
Yin, Y.W. et al., Current Opinion in Structural Biology 2011, 21:83-91.*
Freshney et al.,Culture of Animal Cells, A Manual of Basic Technique, Alan R. Liss, Inc., 1983, New York, p. 4.*
Dermer et al., Bio/Technology, 1994, 12:320.*
Golub et al., Science, 286, 531-537, 1999.*
Cecil Textbook of Medicine, edited by Bennet, J.C., and Plum F., 20th edition,vol. 1, 1004-1010, 1996.*
Patil et al. Tetrahedron Letters, 35, 5339-5342, 1994.*
International Search Report from WO 2010/002877 dated Sep. 23, 2010.
International Preliminary Report on Patentability from WO 2010/002877 dated Jan. 5, 2011.
International Search Report from WO 2008/089105 dated Jul. 7, 2008.
International Preliminary Report on Patentability from WO 2008/089105 dated Jul. 14, 2009.
Non-final Office Action from U.S. Appl. No. 12/496,311 dated Sep. 16, 2011.
Chu, C. K. et al., "Nucleosides. CXXXV. Synthesis of Some 9-(2-Deoxy-2-fluoro-β-D-arabinofuranosyl)-9H-purines and Their Biological Activites", *Chem. Pharm. Bull.*, 37(2):336-339 (Pharmaceutical Society of Japan, 1989).
Herdewijn, P. et al., "Synthesis and Anti-HIV Activity of Various 2'- and 3'-Substituted 2',3'-dideoxyadenosines: A Structure-Activity Analysis", *J. Med. Chem.*, 30:2131-2137 (American Chemical Society, USA, 1987).
Kodama, E-I. et al., "4'-Ethynyl Nucleoside Analogs: Potent Inhibitors of Multidrug-Resistant Human Immunodeficiency Virus Variants In Vitro", *Antimicrobial Agents and Chemotherapy*, 45(5):1539-1546 (American Society for Microbiology, USA, May 2001).
Koshida, R. et al., "Structure-Activity Relationships of Fluorinated Nucleoside Analogs and Their Synergistic Effect in Combination with Phosphonoformate against Human Immunodeficiency Virus Type 1", *Antimicrobial Agents and Chemotherapy*, 33(12):2083-2088 (American Society for Microbiology, USA, Dec. 1989).

(Continued)

*Primary Examiner* — Venkataraman Balasubramanian
(74) *Attorney, Agent, or Firm* — Dana M. Gordon; Foley Hoag LLP

(57) ABSTRACT

The invention provides compounds of Formula (I), as described herein, as well as pharmaceutical compositions comprising the compounds, and synthetic methods and intermediates that are useful for preparing the compounds. The compounds of Formula (I) are useful as anti-viral agents and/or as anti-cancer agents.

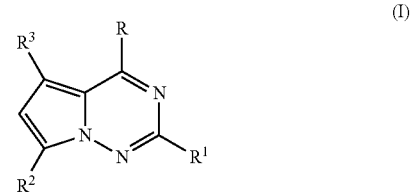

(I)

1 Claim, No Drawings

OTHER PUBLICATIONS

Lin, T.-S. et al., "Synthesis and Anticancer Activity of Various 3'-Deoxy Pyrimidine Nucleoside Analogues and Crystal Structure of 1-(3-Deoxy-β-D-*threo*-pentofuranosyl)cytosine", *J. Med. Chem.*, 34:693-701 (American Chemical Society, USA, 1991).

Olsen, D. B. et al., "A 7-Deaza-Adenosine Analog is a Potent and Selective Inhibitor of Hepatitis C Virus Replication with Excellent Pharmacokinetic Properties", *Antimicrobial Agents and Chemotherapy*, 48(10):3944-3953 (American Society for Microbiology, USA, Oct. 2004).

Watanabe, K. A. et al., "Nucleosides. 110. Synthesis and Antiherpes Virus Activity of Some 2'-Fluoro-2'-deoxyarabinofuranosylpyrimidine Nucleosides", *Journal of Medicinal Chemistry*, 22(1):21-24 (American Chemical Society, USA, 1979).

Yokota, T. et al., "Comparative Activities of Several Nucleoside Analogs against Duck Hepatitis B Virus In Vitro", *Antimicrobial Agents and Chemotherapy*, 34(7):1326-1330 (American Society for Microbiology, USA, Jul. 1990).

\* cited by examiner

ANTIVIRAL NUCLEOSIDE ANALOGS

This application is a National Stage application under 35 U.S.C. §371 of International Application No. PCT/US2008/050929, having an International Filing Date of 11 Jan. 2008, and claims priority to U.S. Provisional Application No. 60/880,278 that was filed on 12 Jan. 2007, which applications are hereby incorporated by reference herein in their entireties.

PRIORITY OF INVENTION

This application claims priority to U.S. Provisional Application No. 60/880,278 that was filed on 12 Jan. 2007.

BACKGROUND OF THE INVENTION

Viral diseases are a major cause of death and economic loss in the world.

The Flaviviridae family of viruses consists of three genera: the flaviviruses (including dengue, West Nile, and yellow fever viruses), hepatitis virus (HCV), and the pestiviruses (including bovine viral diarrhea virus, BVDV). The disease states and conditions caused by members of this family include yellow fever, dengue, Japanese encephalitis, St. Louis encephalitis, Hepatitis B and C, West Nile disease, and AIDS. Currently, human immunodeficiency virus (HIV), hepatitis B virus (HBV) and hepatitis C virus (HCV) infections are responsible for the largest number of viral related deaths worldwide. Although there are some drugs useful for treating HIV, there are only a few drugs useful for treating HBV, and no drugs that are broadly useful for treating HCV.

Ribavirin (1-β-D-ribofuranosyl-1-1,2,4-triazole-3-carboxamide) is a synthetic, non-interferon-inducing, broad spectrum antiviral nucleoside. Ribavirin is structurally similar to guanosine, and has in vitro activity against several DNA and RNA viruses including Flaviviridae (Davis. Gastroenterology 118:S104-S114, 2000). Ribavirin reduces serum amino transferase levels to normal in 40% of patients, but it does not lower serum levels of HCV-RNA (Davis. Gastroenterology 118:S104-S114, 2000). Thus, ribavirin alone is not effective in reducing viral RNA levels. Additionally, ribavirin has significant toxicity and is known to induce anemia.

Interferons (IFNs) are compounds which have been commercially available for the treatment of chronic hepatitis for nearly a decade. IFNs are glycoproteins produced by immune cells in response to viral infection. IFNs inhibit viral replication of many viruses, including HCV. When used as the sole treatment for hepatitis C infection, IFN suppresses serum HCV-RNA to undetectable levels. Additionally, IFN normalizes serum amino transferase levels. Unfortunately, the effects of IFN are temporary and a sustained response occurs in only 8%-9% of patients chronically infected with HCV (Davis. Gastroenterology 118:S104-S114, 2000).

HCV is a positive stranded ss RNA virus with a well characterized RNA-dependent RNA polymerase (RdRp) and a well characterized disease progression. HCV has infected an estimated 170 million people worldwide, leading to a major health crisis as a result of the disease. Indeed, during the next few years the number of deaths from HCV-related liver disease and hepatocellular carcinoma may overtake those caused by AIDS. Egypt is the hardest hit country in the world, with 23% of the population estimated to be carrying the virus; whereas, in the USA the prevalence of chronic infections has recently been determined to be around 1.87% (2.7 million persons). HCV infections become chronic in about 50% of cases. Of these, about 20% develop liver cirrhosis that can lead to liver failure, including hepatocellular carcinoma.

The NS5B region of HCV encodes a 65 KDa RdRp thought to be responsible for viral genome replication. RdRps function as the catalytic subunit of the viral replicase required for the replication of all positive-strand viruses. The NS5B protein has been well characterized, shown to possess the conserved GDD motif of RdRps and in vitro assay systems have been reported. Cellular localization studies revealed that NS5B is membrane-associated in the endoplasmic reticulum like NS5A, suggesting that those two proteins may remain associated with one another after proteolytic processing. Additional evidence suggests that NS3, NS4A and NS5B interact with each other to form a complex that functions as part of the replication machinery of HCV.

The X-ray crystal structure of NS5B apoenzyme has been determined and three very recent publications describe the unusual shape of the molecule. This unique shape for a polymerase, resembling a flat sphere, is attributed to extensive interactions between the fingers and thumb subdomains in such a way that the active site is completely encircled, forming a cavity 15 Å across and 20 Å deep. Modeling studies showed that the NS5B apoenzyme can accommodate the template-primer without large movement of the subdomains, suggesting that the structure is preserved during the polymerization reaction. The RdRp polypeptides from various members of the Flaviviridae family and other viral families have been shown to be conserved (J. A. Bruenn, Nucleic Acids Research, Vol. 19, No. 2 p. 217, 1991).

Currently, there are no safe and effective therapeutic agents on the market that target HCV polymerase. There is currently a need for therapeutic agents and therapeutic methods that are useful for treating viral infections, such as HCV, HIV, and HBV.

In addition, there is also a current need for therapeutic agents and therapeutic methods that are useful for treating cancer. Even though significant advances have occurred in the treatment of cancer, it still remains a major health concern. It has been reported that cancer is the cause of death of up to one of every four Americans. Notwithstanding the advances in treatments for cancer and other diseases there is still a need for novel drugs that are effective to treat cancer.

SUMMARY OF THE INVENTION

The present invention provides compounds that are inhibitors of viral RNA and DNA polymerases (e.g. polymerases from hepatitis B, hepatitis C, human immunodeficiency virus, Polio, Coxsackie A and B, Rhino, Echo, small pox, Ebola, and West Nile virus) and that are useful for treating HCV, as well as other viral infections (e.g. flaviviral infections), and cancer.

Accordingly, the invention provides a novel compound of Formula I as described herebelow, or a pharmaceutically acceptable salt or prodrug thereof.

The invention also provides a pharmaceutical composition comprising a compound of Formula I, or a pharmaceutically acceptable salt or prodrug thereof, and a pharmaceutically acceptable carrier. The composition can optionally comprise one or more additional anti-viral or anti-cancer agents.

The invention also provides a method for treating a viral infection in an animal comprising administering to the animal an effective amount of a compound of Formula I, or a pharmaceutically acceptable salt or prodrug thereof.

The invention also provides a method for inhibiting a viral RNA or DNA polymerase comprising contacting the polymerase (in vitro or in vivo) with an effective inhibitory amount of a compound of Formula I, or a pharmaceutically acceptable salt or prodrug thereof.

The invention also provides a method for treating cancer in an animal comprising administering to the animal an effective amount of a compound of Formula I, or a pharmaceutically acceptable salt or prodrug thereof.

The invention also provides a compound of Formula I, or a pharmaceutically acceptable salt or prodrug thereof, for use in medical therapy (e.g. for use in treating a viral infection or for use in treating cancer).

The invention also provides the use of a compound of Formula I, or a pharmaceutically acceptable salt or prodrug thereof, to prepare a medicament useful for treating a viral infection in an animal (e.g. a human).

The invention also provides the use of a compound of Formula I, or a pharmaceutically acceptable salt or prodrug thereof, to prepare a medicament useful for treating cancer in an animal (e.g. a human).

The invention also provides novel synthetic intermediates and synthetic methods that are disclosed herein as being useful for preparing compounds of Formula I, or a salt or prodrug thereof. Some compounds of Formula I may be useful as synthetic intermediates for preparing other compounds of Formula I.

DETAILED DESCRIPTION OF THE INVENTION

Definitions

The term "pharmaceutically acceptable salt" as used herein refers to a compound of the present disclosure derived from pharmaceutically acceptable bases, inorganic or organic acids. Examples of suitable acids include, but are not limited to, hydrochloric, hydrobromic, sulfuric, nitric, perchloric, fumaric, maleic, phosphoric, glycollic, lactic, salicyclic, succinic, toluene-p-sulfonic, tartaric, acetic, citric, methanesulfonic, formic, benzoic, malonic, naphthalene-2-sulfonic, trifluoroacetic and benzenesulfonic acids. Salts derived from appropriate bases include, but are not limited to, alkali such as sodium and ammonia.

The terms "treat", "treating" and "treatment" as used herein include administering a compound prior to the onset of clinical symptoms of a disease state/condition so as to prevent any symptom, as well as administering a compound after the onset of clinical symptoms of a disease state/condition so as to reduce or eliminate any symptom, aspect or characteristic of the disease state/condition. Such treating need not be absolute to be useful.

The term "animal" as used herein refers to any animal, including mammals, such as, but not limited to, mice, rats, other rodents, rabbits, dogs, cats, swine, cattle, sheep, horses, and primates. In one specific embodiment of the invention the animal is a human.

The term "therapeutically effective amount", in reference to treating a disease state/condition, refers to an amount of a compound either alone or as contained in a pharmaceutical composition that is capable of having any detectable, positive effect on any symptom, aspect, or characteristics of a disease state/condition when administered as a single dose or in multiple doses. Such effect need not be absolute to be beneficial.

The term "alkyl" as used herein refers to alkyl groups having from 1 to 6 carbon atoms. This term is exemplified by groups such as methyl, ethyl, n-propyl, iso-propyl, n-butyl, t-butyl, n-pentyl and the like. In a specific embodiment, the alkyl groups have from 1-4 carbon atoms and are referred to as lower alkyl.

The term "substituted alkyl" as used herein refers to an alkyl group having from 1 to 3 substituents, said substituents being selected from the group consisting of alkoxy, alkoxyalkyl, tri($C_1$-$C_4$alkyl)silyl, substituted alkoxy, acyl, substituted acyl, acylamino, acyloxy, oxyacyl, amino, substituted amino, aminoacyl, aryl, substituted aryl, aryloxy, substituted aryloxy, cyano, halogen, hydroxyl, nitro, $N_3$, carboxyl, carboxyl esters, thiol, thioalkyl, substituted thioalkyl, thioaryl, substituted thioaryl, thioheteroaryl, substituted thioheteroaryl, thiocycloalkyl, substituted thiocycloallcyl, thioheterocyclic, substituted thioheterocyclic, cycloalkyl, substituted cycloalkyl, heteroaryl, substituted heteroaryl, heterocyclic, and substituted heterocyclic. In one specific embodiment of the invention, the term "substituted alkyl" refers to an alkyl group substituted with 1 to 3 substituents, said substituents being selected from the group consisting of alkoxy, alkoxyalkyl, tri($C_1$-$C_4$alkyl)silyl, acyl, acylamino, acyloxy, oxyacyl, amino, aminoacyl, aryl, aryloxy, cyano, halogen, hydroxyl, nitro, $N_3$, carboxyl, carboxyl esters, thiol, thioalkyl, thioaryl, thioheteroaryl, thiocycloalkyl, thioheterocyclic, cycloalkyl, heteroaryl, and heterocyclic.

The terms "alkenyl" or "alkene" as used herein refers to an alkenyl group having from 2 to 10 carbon atoms and having at least 1 site of alkenyl unsaturation. Such groups are exemplified by vinyl(ethen-1-yl), allyl, but-3-en-1-yl, and the like.

The term "substituted alkenyl" as used herein refers to alkenyl groups having from 1 to 3 substituents, said substituents being selected from those describe above for a substituted alkyl.

The term "alkynyl" or "alkyne" as used herein refers to an alkynyl group having from 2-10 carbon atoms and having at least 1 site of alkynyl unsaturation. Such groups are exemplified by, but not limited to, ethyn-1-yl, propyn-1-yl, propyn-2-yl, 1-methylprop-2-yn-1-yl, butyn-1-yl, butyn-2-yl, butyn-3-yl, and the like.

The term "substituted alkynyl" as used herein refers to alkynyl groups having from 1 to 3 substituents, said substituents being selected those describe above for a substituted alkyl.

The term "alkoxy" refers to the group alkyl-O—.

The term "substituted alkoxy" as used herein refers to the group substituted alkyl-O—.

The term "acyl" as used herein refers to the groups alkyl-C(O)—, alkenyl-C(O)—, alkynyl-C(O)—, cycloalkyl-C(O)—, aryl-C(O)—, heteroaryl-C(O)—, and heterocyclic-C(O).

The term "substituted acyl" as used herein refers to the groups substituted alkyl-C(O)—, substituted alkenyl-C(O)—, substituted alkynyl-C(O)—, substituted cycloalkyl-C(O)—, substituted aryl-C(O)—, substituted heteroaryl-C(O), and substituted heterocyclic-C(O)—.

The term "acylamino" as used herein refers to the group-C(O)N$Z_1Z_2$ where each $Z_1$ and $Z_2$ are independently selected from the group consisting of hydrogen, alkyl, substituted alkyl, alkenyl, substituted alkenyl, alkynyl and substituted alkynyl, and the substituents described above in the definition of substituted alkyl.

The term "acyloxy" as used herein refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O—.

The term "oxyacyl" as used herein refers to the groups alkyl-OC(O)—, substituted alkyl-OC(O)—, alkenyl-OC (O)—, substituted alkenyl-OC(O)—, alkynyl-OC(O)—, substituted alkynyl-OC(O)—, aryl-OC(O)—, substituted aryl-OC(O)—, cycloalkyl-OC(O)—, substituted cycloalkyl-OC(O)—, heteroaryl-OC(O)—, substituted heteroaryl-OC(O)—, heterocyclic-OC(O)—, and substituted heterocyclic-OC(O)—.

The term "amino" as used herein refers to the group —$NH_2$.

The term "substituted amino" as used herein refers to the group —$NZ_1Z_2$ where $Z_1$ and $Z_2$ are as described above in the definition of acylamino, provided that $Z_1$ and $Z_2$ are both not hydrogen.

The term "aminoacyl" as used herein refers to the groups —$NZ_3C(O)$alkyl, —$NZ_3C(O)$substituted alkyl, —$NZ_3C(O)$cycloalkyl, —$NZ_3C(O)$substituted cycloalkyl, —$NZ_3C(O)$alkenyl, —$NZ_3C(O)$substituted alkenyl, —$NZ_3C(O)$alkynyl, —$NZ_3C(O)$substituted alkynyl, —$NZ_3C(O)$aryl, —$NZ_3C(O)$substituted aryl, —$NZ_3C(O)$heteroaryl, —$NZ_3C(O)$substituted heteroaryl, —$NZ_3C(O)$heterocyclic, and —$NZ_3C(O)$substituted heterocyclic, where $Z_3$ is hydrogen or alkyl.

The term "aryl" as used herein refers to a monovalent aromatic cyclic group of from 6 to 14 carbon atoms having a single ring (e.g., phenyl) or multiple condensed rings (e.g., naphthyl or anthryl) which condensed rings may or may not be aromatic. Exemplary aryls include, but are not limited to, phenyl and naphthyl.

The term "substituted aryl" as used herein refers to aryl groups which are substituted with from 1 to 3 substituents selected from alkyl, substituted alkyl, alkenyl, substituted alkenyl, alkynyl and substituted alkynyl, and those substituents described above in the definition of substituted alkyl.

The term "aryloxy" as used herein refers to the group aryl-O— that includes, by way of example but not limitation, phenoxy, naphthoxy, and the like.

The term "substituted aryloxy" as used herein refers to substituted aryl-O-groups.

The term "carboxyl" as used herein refers to —COOH or salts thereof.

The term "carboxyl esters" as used herein refers to the groups-C(O)O-alkyl, —C(O)O-substituted alkyl, —C(O)O-aryl, and —C(O)O-substituted aryl The term "cycloalkyl" as used herein refers to a saturated or unsaturated cyclic hydrocarbon ring systems, such as those containing 1 to 3 rings and 3 to 7 carbons per ring. Exemplary groups include but are not limited to cyclopropyl, cyclobutyl, cyclopentyl, cyclohexyl, cycloheptyl, and adamantyl.

The term "substituted cycloalkyl" as used herein refers to a cycloalkyl having from 1 to 5 substituents selected from the group consisting of oxo (=O), thioxo (=S), alkyl, substituted alkyl, and those substituents described in the definition of substituted alkyl.

The term "cycloalkoxy" as used herein refers to —O-cycloalkyl groups.

The term "substituted cycloalkoxy" as used herein refers to —O-substituted cycloalkyl groups.

The term "formyl" as used herein refers to HC(O)—.

The term "halogen" as used herein refers to fluoro, chloro, bromo and iodo.

The term "heteroaryl" as used herein refers to an aromatic group of from 1 to 10 carbon atoms and 1 to 4 heteroatoms selected from the group consisting of oxygen, nitrogen, sulfur in the ring. The sulfur and nitrogen heteroatoms atoms may also be present in their oxidized forms. Such heteroaryl groups can have a single ring (e.g., pyridyl or furyl) or multiple condensed rings (e.g., indolizinyl or benzothienyl) wherein the condensed rings may or may not be aromatic and/or contain a heteroatom. Exemplary heteroaryl groups include, but are not limited to, heteroaryls include pyridyl, pyrrolyl, thienyl, indolyl, thiophenyl, and furyl.

The term "substituted heteroaryl" as used herein refers to heteroaryl groups that are substituted with from 1 to 3 substituents selected from the same group of substituents defined for substituted aryl.

The term "heteroaryloxy" as used herein refers to the group —O-heteroaryl.

The term "substituted heteroaryloxy" as used herein refers to the group —O-substituted heteroaryl.

The term "heterocycle" or "heterocyclic" or "heterocycloalkyl" refers to a saturated or unsaturated group (but not heteroaryl) having a single ring or multiple condensed rings, from 1 to 10 carbon atoms and from 1 to 4 hetero atoms selected from the group consisting of nitrogen, oxygen, sulfur, within the ring wherein, in fused ring systems, one or more the rings can be cycloalkyl, aryl or heteroaryl provided that the point of attachment is through the heterocyclic ring. The sulfur and nitrogen heteroatoms atoms may also be present in their oxidized forms.

The term "substituted heterocycle" or "substituted heterocyclic" or "substituted heterocycloalkyl" refers to heterocycle groups that are substituted with from 1 to 3 of the same substituents as defined for substituted aryl.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), piperidinyl, pyrrolidine, tetrahydrofuranyl, and the like.

The term "heterocyclyloxy" as used herein refers to the group —O-heterocyclic.

The term "substituted heterocyclyloxy" as used herein refers to the group-O-substituted heterocyclic.

The term "phosphate" as used herein refers to the groups —OP(O)(OH)$_2$ (monophosphate or phospho), —OP(O)(OH)OP(O)(OH)$_2$ (diphosphate or diphospho) and —OP(O)(OH)OP(O)(OH)OP(O)(OH)$_2$ (triphosphate or triphospho) or salts thereof including partial salts thereof. It is understood that the initial oxygen of the mono-, di-, and triphosphate may include the oxygen atom of a sugar.

The term "phosphate esters" as used herein refers to the mono-, di- and tri-phosphate groups described above wherein one or more of the hydroxyl groups is replaced by an alkoxy group.

The term "phosphonate" refers to the groups —OP(O)(Z4)(OH) or —OP(O) ($Z_4$)(O$Z_4$) or salts thereof including partial salts thereof, wherein each $Z_4$ is independently selected from hydrogen, alkyl, substituted alkyl, carboxylic acid, and carboxyl ester. It is understood that the initial oxygen of the phosphonate may include the oxygen of a sugar.

The term "thiol" as used herein refers to the group —SH.

The term "thioalkyl" or "alkylthioether" or "thioalkoxy" refers to the group-S-alkyl.

The term "substituted thioalkyl" or "substituted alkylthioether" or "substituted thioalkoxy" refers to the group —S-substituted alkyl.

The term "thiocycloalkyl" as used herein refers to the group —S-cycloalkyl.

The term "substituted thiocycloalkyl" as used herein refers to the group —S-substituted cycloalkyl.

The term "thioaryl" as used herein refers to the group —S-aryl.

The term "substituted thioaryl" as used herein refers to the group —S-substituted aryl.

The term "thioheteroaryl" as used herein refers to the group —S-heteroaryl.

The term "substituted thioheteroaryl" as used herein refers to the group —S-substituted heteroaryl.

The term "thioheterocyclic" as used herein refers to the group —S-heterocyclic.

The term "substituted thioheterocyclic as used herein refers to the group —S-substituted heterocyclic.

The term "amino acid sidechain" refers to the $Z_7$ substituent of α-amino acids of the formula $Z_6NHCH(Z_7)COOH$ where $Z_7$ is selected from the group consisting of hydrogen, alkyl, substituted alkyl and aryl and $Z_6$ is hydrogen or together with $Z_7$ and the nitrogen and carbon atoms bound thereto respectively form a heterocyclic ring. In one embodiment, the α-amino acid sidechain is the sidechain of one of the twenty naturally occurring L amino acids.

Sugars described herein may either be in D or L configuration.

compounds of Formula I

Compounds of the invention include compounds of Formula I:

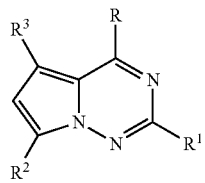

(I)

wherein:

R is $OR_a$, $SR_a$, $NR_aR_b$, $NR_aNR_bR_c$, alkyl, substituted alkyl, alkenyl, substituted alkenyl, alkynyl, substituted alkynyl, aryl, substituted aryl, $(CH_2)_n$—$CH(NHR_a)CO_2R_b$, $(CH_2)_n$—S-alkyl, $(CH_2)_n$—S-aryl, Cl, F, Br, I, CN, $COOR_a$, $CONR_aR_b$, $NHC(=NR_a)NHR_b$, $NR_aOR_b$, $NR_aNO$, $NHCONHR_a$, $NR_aN=NR_b$, $NR_aN=CHR_b$, $NR_aC(O)NR_bF$, $NR_aC(S)NR_bR_cC$, $NR_aC(O)OR_b$, $CH=N$—$OR_a$, $NR_aC(=NH)NR_bR_cC$, $NR_aC(O)NR_bNR_cR_d$, $O$—$C(O)R_a$, $OC(O)$—$OR_a$, $ONH$—$C(O)O$-alkyl, $ONHC(O)O$-aryl, $ONR_aR_b$, $SNR_aR_b$, $S$—$ONR_aR_b$, $CHO$, $C(=S)N R_aR_b$, nitro, $CH(NR_a)OR_b$, or $SO_2NR_aR_b$; and $R^3$ is H, CN, $NO_2$, alkyl, substituted alkyl, alkenyl, substituted alkenyl, alkynyl, substituted alkynyl, $CH=CF_2$, $CH(=NR_a)OR_b$, CHO, $CH=CH$—$OCH_3$, $NHCONH_2$, $NHCSNH_2$, $CONR_aR_b$, $CSNR_aR_b$, $CO_2R_a$, alkoxy, $NH_2$, alkylamino, dialkylamino, halogen, (1,3-oxazol-2-yl), (1,3-oxazol-5-yl), (1,3-thiazol-2-yl), (imidazol-2-yl), (2-oxo[1,3]dithiol-4-yl), (furan-2-yl), (2H[1,2,3]triazol-4-yl), $C(=NH)NH_2$, $C(=NH)NHOH$, $C(=NOH)NH_2$, acyl, substituted acyl, $OR_a$, $C(=NR_a)R_b$, $CH=NNR_aR_b$, $CH=NOR_a$, $CH(OR_a)_2$, $B(OR_a)_2$, $C≡C$—$C(=O)NR_aR_b$, $(CH_2)_n$—S-alkyl, $(CH_2)_n$—S-aryl, $(CH_2)_n$—S(O)-alkyl, $(CH_2)_n$—S(O)-aryl, $(CH_2)_n$—$S(O_2)$-alkyl, $(CH_2)_n$—$S(O_2)$-aryl, $(CH_2)_n$—$SO_2NR_aR_b$, or $(CH_2)_n$—$OR_a$; or R and $R^3$ together with atoms to which they are attached may form a cycloalkyl, substituted cycloalkyl, aryl, substituted aryl, heterocycloalkyl, substituted heterocycloalkyl, heteroaryl, or substituted heteroaryl;

n is 0-5;

$R^1$ is H, $NR_aR_b$, Cl, F, $OR_a$, $SR_a$, $NHCOR_a$, $NHSO_2R_a$, $NHCONHR_a$, CN, alkyl, aryl, $ONR_aR_b$, or $NR_aC(O)OR_b$;

$R^2$ is a nucleoside sugar group;

$R_a$, $R_b$, $R_c$, and $R_d$ are independently selected from the group consisting of H, alkyl, substituted alkyl, alkenyl, substituted alkenyl, alkynyl, substituted alkynyl, cycloalkyl, heterocyclic, aryl, substituted aryl, acyl, substituted acyl, $SO_2$-alkyl, amino, substituted amino, and NO; or $R_a$ and $R_b$ together with the nitrogen to which they are attached form a pyrrolidino, piperidino, piperazino, azetidino, morpholino, or thiomorpholino ring; or $R_b$ and $R_c$ together with the nitrogen to which they are attached form a pyrrolidino, piperidino, piperazino, azetidino, morpholino, or thiomorpholino ring; and $R_c$, and $R_d$ are independently selected from the group consisting of H, alkyl, substituted alkyl, cycloalkyl, substituted cycloalkyl, aryl, substituted aryl, heteroaryl, and substituted heteroaryl; or $R_c$, and $R_d$ together with N atom to which they are attached may form a heterocycloalkyl, substituted heterocycloalkyl, heteroaryl, or substituted heteroaryl;

or a pharmaceutically acceptable salt or prodrug thereof.

In one embodiment of the invention compounds of the invention include compounds of Formula I:

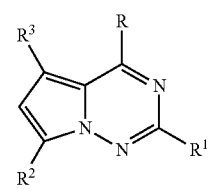

(I)

wherein:

R is $OR_a$, $SR_a$, $NR_aR_b$, $NR_aNR_bR_c$, alkyl, substituted alkyl, alkenyl, substituted alkenyl, alkynyl, substituted alkynyl, aryl, substituted aryl, $(CH_2)_n$—$CH(NHR_a)CO_2R_b$, $(CH_2)_n$—S-alkyl, $(CH_2)_n$—S-aryl, Cl, F, Br, I, CN, $COOR_a$, $CONR_aR_b$, $NHC(=NR_a)NHR_b$, $NR_aOR_b$, $NR_aNO$, $NHCONHR_a$, $NR_aN=NR_b$, $NR_aN=CHR_b$, $NR_aC(O)NR_bR_c$, $NR_aC(S)NR_bR_c$, $NR_aC(O)OR_b$, $CH=N$—$OR_a$, $NR_aC(=NH)NR_bR_c$, $NR_aC(O)NR_bNR_cR_d$, $O$—$C(O)R_a$, $OC(O)$—$OR_a$, $ONH$—$C(O)O$-alkyl, $ONHC(O)O$-aryl, $ONR_aR_b$, $SNR_aR_b$, $S$—$ONR_aR_b$, CHO, $C(=S)N R_aR_b$, nitro, $CH(NR_a)OR_b$, or $SO_2NR_aR_b$; and $R^3$ is H, CN, $NO_2$, alkyl, substituted alkyl, alkenyl, substituted alkenyl, alkynyl, substituted alkynyl, $CH=CF_2$, $CH(=NR_a)OR_b$, CHO, $CH=CH$—$OCH_3$, $NHCONH_2$, $NHCSNH_2$, $CONR_aR_b$, $CSNR_aR_b$, $CO_2R_a$, alkoxy, $NH_2$, alkylamino, dialkylamino, halogen, (1,3-oxazol-2-yl), (1,3-oxazol-5-yl), (1,3-thiazol-2-yl), (imidazol-2-yl), (2-oxo[1,3]dithiol-4-yl), (furan-2-yl), (2H[1,2,3]triazol-4-yl), $C(=NH)NH_2$, $C(=NH)NHOH$, $C(=NOH)NH_2$, acyl, substituted acyl, $OR_a$, $C(=NR_a)R_b$, $CH=NNR_aR_b$, $CH=NOR_a$, $CH(OR_a)_2$, $B(OR_a)_2$, $C≡C$—$C(=O)NR_aR_b$, or $N(=NHNH_2)NHNH_2$; or R and $R^3$ together with atoms to which they are attached may form a cycloalkyl, substituted cycloalkyl, aryl, substituted aryl, heterocycloalkyl, substituted heterocycloalkyl, heteroaryl, or substituted heteroaryl;

n is 0-5;

$R^1$ is H, $NR_aR_b$, Cl, F, $OR_a$, $SR_a$, $NHCOR_a$, $NHSO_2R_a$, $NHCONHR_a$, CN, alkyl, aryl, $ONR_aR_b$, or $NR_aC(O)OR_b$;

$R^2$ is a nucleoside sugar group;

$R_a$, $R_b$, $R_c$, and $R_d$ are independently selected from the group consisting of H, alkyl, substituted alkyl, alkenyl, substituted alkenyl, alkynyl, substituted alkynyl, cycloalkyl, heterocyclic, aryl, substituted aryl, acyl, substituted acyl, $SO_2$-alkyl, amino, substituted amino, and NO; or $R_a$ and $R_b$ together with the nitrogen to which they are attached form a pyrrolidino, piperidino, piperazino, azetidino, morpholino, or thiomorpholino ring; or $R_b$ and $R_c$ together with the nitrogen to which they are attached form a pyrrolidino, piperidino, piperazino, azetidino, morpholino, or thiomorpholino ring; and $R_c$, and $R_d$ are independently selected from the group consisting of H, alkyl, substituted alkyl, cycloalkyl, substituted cycloalkyl, aryl, substituted aryl, heteroaryl, and substituted heteroaryl; or $R_d$, and $R_d$ together with N atom to which they are attached may form a heterocycloalkyl, substituted heterocycloalkyl, heteroaryl, or substituted heteroaryl;

or a pharmaceutically acceptable salt or prodrug thereof.

In one embodiment of the invention, the compound of Formula (I) is not a compound of formula (12):

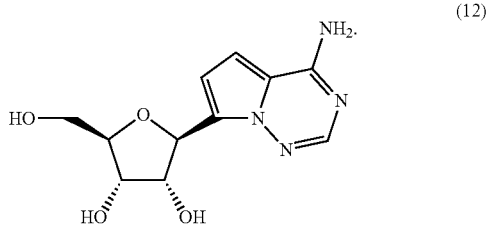 [SMILES: Nc1ncnn2c([C@@H]3O[C@H](CO)[C@@H](O)[C@H]3O)ccc12]

(12)

In one embodiment the invention provides a compound of Formula I as described above, wherein R is $OR_a$, Cl, $SR_a$, $NR_aR_b$, or $NR_aNR_bF$; or a pharmaceutically acceptable salt or prodrug thereof.

In one embodiment the invention provides a compound of Formula I as described above, wherein R is $NR_aR_b$; $R_a$ is selected from the group consisting of H, alkyl, substituted alkyl, alkenyl, substituted alkenyl, alkynyl, substituted alkynyl, cycloalkyl, heterocyclic, aryl, substituted aryl, acyl, substituted acyl, $SO_2$-alkyl and NO; and $R_b$ is selected from the group consisting of H, alkyl, substituted alkyl, alkenyl, substituted alkenyl, alkynyl, substituted alkynyl, cycloalkyl, heterocyclic, aryl, substituted aryl, acyl, substituted acyl, $SO_2$-alkyl and NO; or $R_a$ and $R_b$ together with the nitrogen to which they are attached form a pyrrolidino, piperidino, piperazino, azetidino, morpholino, or thiomorpholino ring.

In one embodiment the invention provides a compound of Formula I as described above, wherein R is $NR_aNR_bR_c$, alkyl, substituted alkyl, alkenyl, substituted alkenyl, alkynyl, substituted alkynyl, aryl, substituted aryl, $(CH_2)_n$—$CH(NHR_a)$ $CO_2R_b$, Cl, F, Br, I, CN, $COOR_a$, $CONR_aR_b$, $NHC(=NR_a)$ $NHR_b$, $NR_aOR_b$, $NR_aNO$, $NHCONHR_a$, $NR_aN=NR_b$, $NR_aN=CHR_b$, $NR_aC(O)NR_bR_c$, $NR_aC(S)NR_bR_c$, $NR_aC(O)OR_b$, $CH=N-OR_a$, $NR_aC(=NH)NR_bR_c$, $NR_aC(O)NR_bNR_cR_d$, O—$C(O)R_a$, $OC(O)$—$OR_a$, ONH—$C(O)O$-alkyl, $ONHC(O)O$-aryl, $ONR_aR_b$, $SNR_aR_b$, S—$ONR_aR_b$, or $SO_2NR_aR_b$.

In one embodiment the invention provides a compound of Formula I as described above, wherein $R^1$ is H or $NR_aR_b$; or a pharmaceutically acceptable salt or prodrug thereof.

In one embodiment the invention provides a compound of Formula I as described above, wherein $R^2$ is a nucleoside sugar group of Group A, B, C, D, E, or F described hereinbelow; or a pharmaceutically acceptable salt or prodrug thereof.

In another embodiment the invention provides a compound of Formula I as described above, wherein $R^2$ is ribose, 2-methylribose, 2-deoxyribose; 2-deoxy-2-fluororibose; arabinose; 2-deoxy-2-fluoroarabinose; 2,3-dideoxyribose; 2,3-dideoxy-2-fluoroarabinose; 2,3-dideoxy-3-fluororibose; 2,3-dideoxy-2,3-didehydroribose; 2,3-dideoxy-3-azidoribose; 2,3-dideoxy-3-thiaribose; or 2,3-dideoxy-3-oxaribose; or a pharmaceutically acceptable salt or prodrug thereof.

In another embodiment the invention provides a compound of Formula I as described above, wherein $R^2$ is thioribose, 2-deoxythioribose; 2-deoxy-2-fluorothioribose; thioarabinose; 2-deoxy-2-fluorothioarabinose; 2,3-dideoxythioribose; 2,3-dideoxy-2-fluorothioarabinose; 2,3-dideoxy-3-fluorothioribose; 2,3-dideoxy-2,3-didehydrothioribose; or 2,3-dideoxy-3-azidothioribose; or a pharmaceutically acceptable salt or prodrug thereof.

In another embodiment the invention provides a compound of Formula I as described above, wherein $R^2$ is 4-hydroxymethylcyclopent-2-ene; 2,3-dihydroxy-4-hydroxymethylcyclopent-4-ene; 3-hydroxy-4-hydroxymethylcyclopentane; 2-hydroxy-4-hydroxymethylcyclopentene; 2-fluoro-3-hydroxy-4-hydroxymethylcyclopentane; 2,3-dihydroxy-4-hydroxymethyl-5-methylenecyclopentane; 4-hydroxymethylcyclopentane, 2,3-dihydroxy-4-hydroxymethylcyclopentane; or 2,3-dihydroxymethylcyclobutane; or a pharmaceutically acceptable salt or prodrug thereof.

In another embodiment the invention provides a compound of Formula I as described above, wherein $R^2$ is 4-hydroxymethylpyrrolidine; 2,3-dihydroxy-4-hydroxymethylpyrrolidine; 2/3-hydroxy-4-hydroxymethylpyrrolidine; 2-fluoro-3-hydroxy-4-hydroxymethylpyrrolidine; or 3-fluoro-2-hydroxy-4-hydroxymethyl-pyrrolidine; or a pharmaceutically acceptable salt or prodrug thereof.

In another embodiment the invention provides a compound of Formula I as described above, wherein $R^3$ is CN, $NO_2$, alkyl, substituted alkyl, alkenyl, substituted alkenyl, alkynyl, substituted alkynyl, $CH=CF_2$, $CH(=NR_a)OR_b$, CHO, $CH=CH-OCH_3$, $NHCONH_2$, $NHCSNH_2$, $CONR_aR_b$, $CSNR_aR_b$, $CO_2R_a$, alkoxy, $NH_2$, alkylamino, dialkylamino, halogen, (1,3-oxazol-2-yl), (1,3-oxazol-5-yl), (1,3-thiazol-2-yl), (imidazol-2-yl), (2-oxo[1,3]dithiol-4-yl), (furan-2-yl), (2H[1,2,3]triazol-4-yl), $C(=NH)NH_2$, $C(=NH)NHOH$, $C(=NOH)NH_2$, acyl, substituted acyl, $OR_a$, $C(=NR_a)R_b$, $CH=NNR_aR_b$, $CH=NOR_a$, $CH(OR_a)_2$, $B(OR_a)_2$, $C\equiv C$—$C(=O)NR_aR_b$, $(CH_2)_n$—S-alkyl, $(CH_2)_n$—S-aryl, $(CH_2)_n$—S(O)-alkyl, $(CH_2)_n$—S(O)-aryl, $(CH_2)_n$—$S(O_2)$-alkyl, $(CH_2)_n$—$S(O_2)$-aryl, or $(CH_2)_n$—$SO_2NR_aR_b$, $(CH_2)_n$—$OR_a$.

In another embodiment the invention provides a compound of Formula I as described above, wherein $R^3$ is CN, substituted alkyl, alkenyl, $CONR_aR_b$, $CO_2R_a$, halogen, or $C(=NH)NH_2$.

In another embodiment the invention provides a compound of Formula I as described above, wherein $R^3$ is CN, hydroxymethyl, 1,2-dihydroxyethyl, vinyl, aminocarbonyl, methoxycarbonyl, carboxy, fluoro, bromo, or $C(=NH)NH_2$.

In another embodiment the invention provides a compound of Formula I as described above, wherein $R_a$, $R_b$, $R_c$, and $R_d$ are independently selected from the group consisting of H, alkyl, and substituted alkyl; or $R_a$ and $R_b$ together with the nitrogen to which they are attached form a pyrrolidino, piperidino, piperazino, azetidino, morpholino, or thiomorpholino ring; or $R_b$ and $R_c$ together with the nitrogen to which they are attached form a pyrrolidino, piperidino, piperazino, azetidino, morpholino, or thiomorpholino ring.

In another embodiment the invention provides a compound of Formula I, which is a compound of the following formula (11);

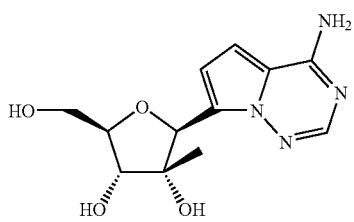

or a pharmaceutically acceptable salt or prodrug thereof.

In another embodiment the invention provides a compound of Formula I, which is a compound of the following formula (III);

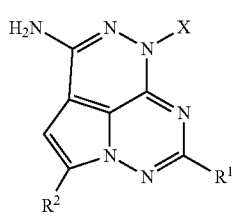

or a pharmaceutically acceptable salt or prodrug thereof; wherein X is H or alkyl.

In one embodiment of the invention, "halogen" is Br, Cl, or F.

Prodrugs

The term "prodrug" as used herein refers to a compound that can be metabolized in vivo to provide a compound of Formula I. Thus prodrugs include compounds that can be prepared by modifying one or more functional groups in a compound of Formula I to provide a corresponding compound that can be metabolized in vivo to provide a compound of Formula I. Such modifications are known in the art. For example, one or more hydroxy groups or amine groups in a compound of Formula I can be acylated with alkyl-C(=O)- groups or with residues from amino acids to provide a prodrug. Alternatively, one or more pendent hydroxyl groups from a mono-, di-, or tri-phosphate functionality in a compound of Formula I can be converted to an alkoxy, substituted alkoxy, aryloxy, or substituted aryloxy group.

In one embodiment, the term prodrug includes a compound wherein one or more hydroxy groups on a nucleoside sugar group (e.g. a 2', 3', or 5' hydroxy group) have been converted to a group that can be metabolized in vivo to provide a compound of Formula I. For example, the invention provides a compound wherein one or more hydroxy groups on a nucleoside sugar group (e.g. a 2', 3', or 5' hydroxy group) have been converted to an acyloxy, acylamino or R—O group, wherein R is a carboxy-linked amino acid.

In one embodiment, the term prodrug includes a compound wherein one or more pendent hydroxyl groups from a mono-, di-, or tri-phosphate functionality in a compound of Formula I is converted to a group $R_y$—O—; wherein each $R_y$ is independently a 1-20 carbon branched or unbranched, saturated or unsaturated chain, wherein one or more (e.g. 1, 2, 3, or 4) of the carbon atoms is optionally replaced with —O— or —S— and wherein one or more of the carbon atoms is optionally substituted with oxo (=O) or thioxo (=S) (See Lefebvre et al., J. Med. Chem. 1995, 38, 3941-50).

In another embodiment, the term prodrug includes a compound wherein one or more pendent hydroxyl groups from a mono-, di-, or tri-phosphate functionality in a compound of Formula I is converted to a group $R_z$—N—; wherein each $R_z$ is a residue of an amino acid. Thus, in the methods of treatment of the present invention, the term "administering" includes administration of a compound of Formula I, as well as administration of a prodrug which converts to a compound of Formula I or a salt thereof in vivo. Conventional procedures for the selection and preparation of prodrug derivatives are described, for example, in "Design of Prodrugs", ed. H. Bundgaard, Elsevier, 1985; and in International Patent Application Publication Number WO 2005/084192. A variety of prodrugs are also described in International Patent Application Number PCT US2004/013063, which was published as International Publication Number WO 2004/096286.

In another embodiment the prodrug comprises one of more groups of formula:

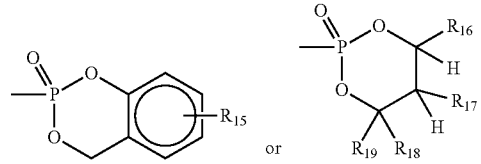

wherein:

$R_{15}$ is H, alkyl, substituted alkyl, aryl, substituted aryl, cycloalkyl, substituted cycloalkyl, heteroaryl, substituted heteroaryl, heterocyclic, substituted heterocyclic, and an amino acid;

$R_{16}$ is H, optionally substituted monocyclic aryl, or optionally substituted monocyclic heteroaryl; and $R_{17}$ is H, halogen, CN, —CO—$R_{20}$, —CON($R_{21}$)$_2$, —CO$_2R_{20}$, —SO$_2R_{20}$, —SO$_2$N($R_{21}$)$_2$, —OR$_{21}$, —SR$_{21}$, —R$_{21}$, —N($R_{21}$)$_2$, —O—COR$_{20}$, —O—CO$_2R_{20}$, —SCOR$_{20}$, —S—CO$_2R_{20}$, —NHCOR$_{21}$, —NHCO$_2R_{21}$, —(CH$_2$)$_p$—OR$_{22}$, or —(CH$_2$)$_p$—SR$_{22}$; or $R_{16}$ and $R_{17}$ are connected via an additional 3-5 atoms to form a cyclic group, optionally containing one heteroatom, that is fused to an aryl group at the beta and gamma position to the O attached to the phosphorus; or $R_{17}$ and $R_{18}$ are connected as described below;

$R_{18}$ and $R_{19}$ are each independently H, alkyl, aryl, heterocycloalkyl, aralkyl, optionally substituted monocyclic aryl or optionally substituted monocyclic heteroaryl; or $R_{18}$ and $R_{19}$ are connected via an additional 2-5 atoms to form a cyclic group, optionally containing 0-2 heteroatoms; or $R_{17}$ and $R_{18}$ are connected via an additional 3-5 atoms to form a cyclic group, optionally containing one heteroatom and $R_{19}$ is H, alkyl, aryl, heterocycloalkyl, aralkyl, optionally substituted monocyclic aryl or optionally substituted monocyclic heteroaryl; and $R_{20}$ is alkyl, aryl, heterocycloalkyl, or arylalkyl;

$R_{21}$ is H, alkyl, aryl, heterocycloalkyl, or arylalkyl;

$R_{22}$ is H or lower acyl;

n is an integer from 2-5;

m is an integer from 10-20; and p is an integer from 2-3.

Prodrug forms of a compound bearing various nitrogen functions (amino, hydroxyamino, amide, etc.) may include the following types of derivatives where each $R_p$ group individually may be hydrogen, substituted or unsubstituted alkyl, aryl, alkenyl, alkynyl, heterocycle, alkylaryl, aralkyl, aralkenyl, aralkynyl, cycloalkyl or cycloalkenyl groups as defined earlier.

(a) Carboxamides, represented as —NHC(O)$R_p$ (b) Carbamates, represented as —NHC(O)O$R_p$ (c) (Acyloxy)alkyl Carbamates, represented as NHC(O)OROC(O)$R_p$ (d) Enamines, represented as —NHCR(=CHCO$_2R_p$) or —NHCR(=CHCONR$_p$R$_p$)

(e) Schiff Bases, represented as —N=CR$_p$R$_p$ (f) Mannich Bases (from carboximide compounds), represented as RCONHCH$_2$NR$_p$R$_p$ Preparations of such prodrug derivatives are discussed in various literature sources (examples are: Alexander et al., J. Med. Chem. 1988, 31, 318; Aligas-Martin et al., PCT WO0041531, p. 30).

Prodrug forms of carboxyl-bearing compounds include esters (—CO$_2$R$_m$) where the R$_m$ group corresponds to any alcohol whose release in the body through enzymatic or hydrolytic processes would be at pharmaceutically acceptable levels. Another prodrug derived from a carboxylic acid form of the disclosure may be a quaternary salt type of structure described by Bodor et al., J. Med. Chem. 1980, 23, 469.

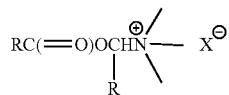

Nucleoside Sugar Groups

The term "nucleoside sugar group" as used herein includes cyclic and acyclic groups that can be included as the sugar portion of a nucleoside analog of Formula I. Many examples of such groups are known in the field of nucleoside chemistry (See for example Antiviral Drugs by John S. Driscoll (2002) published by Ashgate Publishing Ltd.).

The term nucleoside sugar group includes substituted and unsubstituted tetrahydrofuranyl and dihydrofuranyl compounds including those set forth in group (A) below, substituted and unsubstituted tetrahydrothiophenyl and dihydrothiophenyl compounds including those set forth in group (B) below, substituted and unsubstituted alkyl compounds including those set forth in group (C) below, substituted and unsubstituted cycloalkyl and cycloalkenyl compounds including those set forth in group (D) below, substituted and unsubstituted dihydropyrrolidinyl and tetrahydropyrrolidinyl compounds including those set forth in group (E) below, and substituted and unsubstituted dioxolane, substituted and unsubstituted thioxolane, and substituted and unsubstituted dithiolane compounds including those set forth in group (F) below.

Group A

Examples of substituted tetrahydro and dihydrofuranyl compounds include those compounds represented by the general structures:

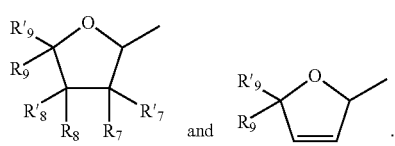

Specific examples include, but are not limited to, the following compounds:

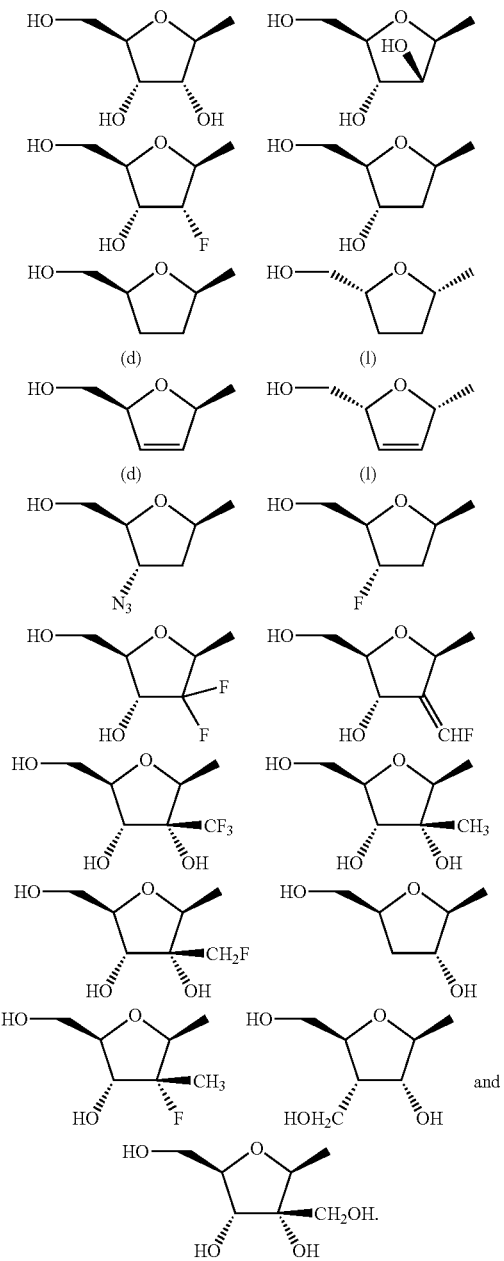

Group B

Examples of substituted tetrahydrothiophenyl and dihydrothiophenyl compounds include those compounds represented by the general structures:

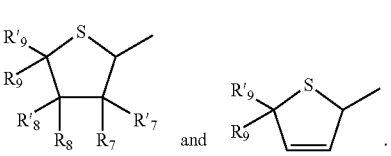

Specific examples include, but are not limited to, the following compounds:

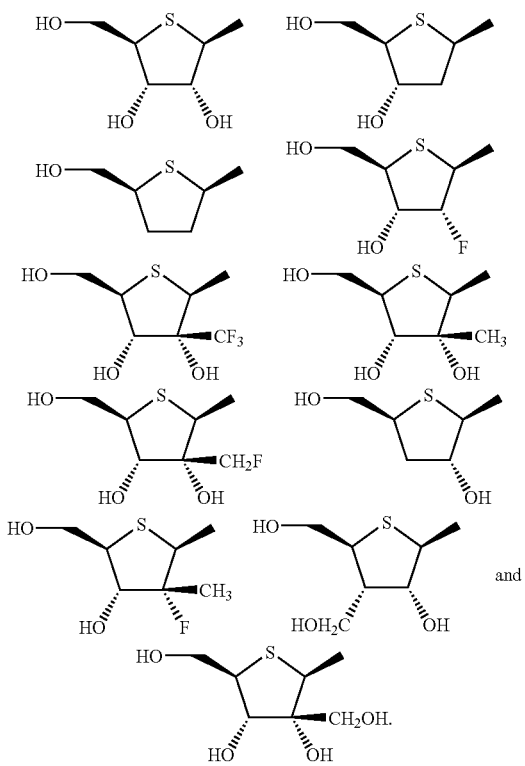

Group C

Examples of substituted alkyl compounds include those compounds represented by:

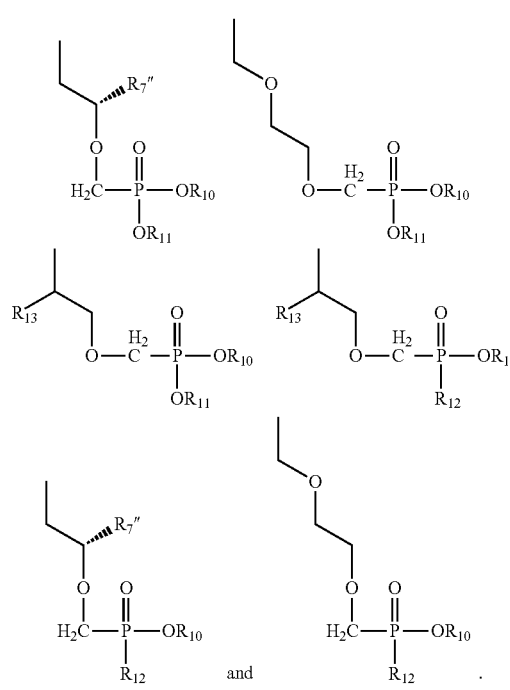

Specific examples include, but are not limited to, the following compounds:

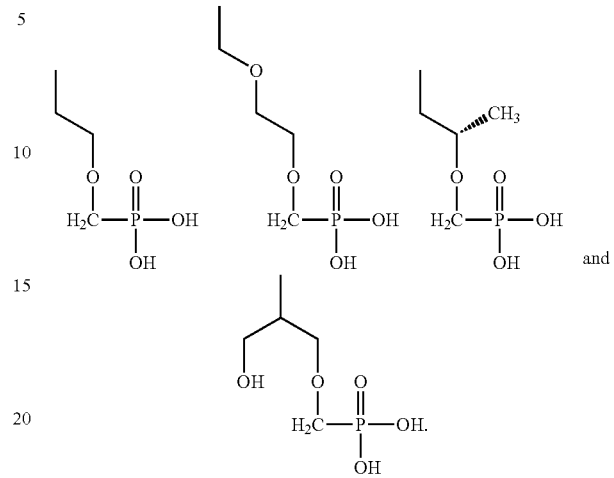

Group D

Examples of substituted cycloalkyl and cycloalkenyl compounds include those compounds represented by the general structures:

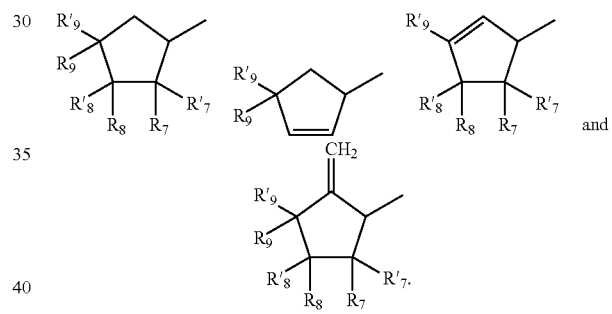

Specific examples include, but are not limited to, the following compounds:

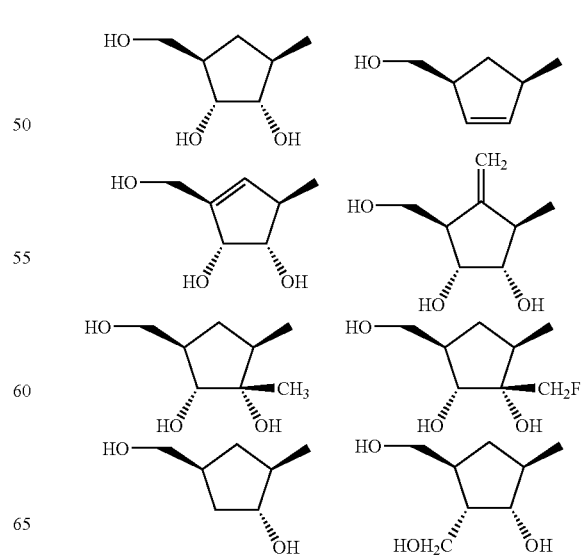

-continued

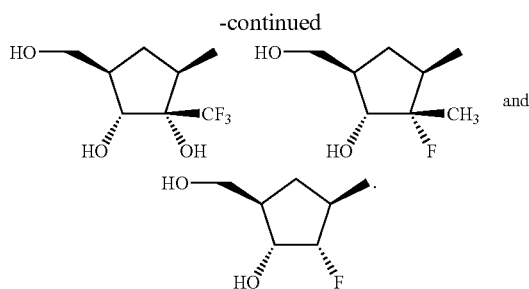

Group E

Examples of substituted dihydropyrrolidinyl and tetrahydropyrrolidinyl compounds include those compounds represented by the general structures:

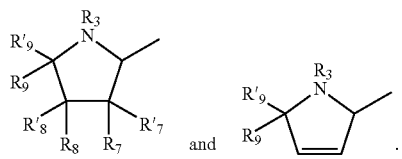

Specific examples include, but are not limited to, the following compounds:

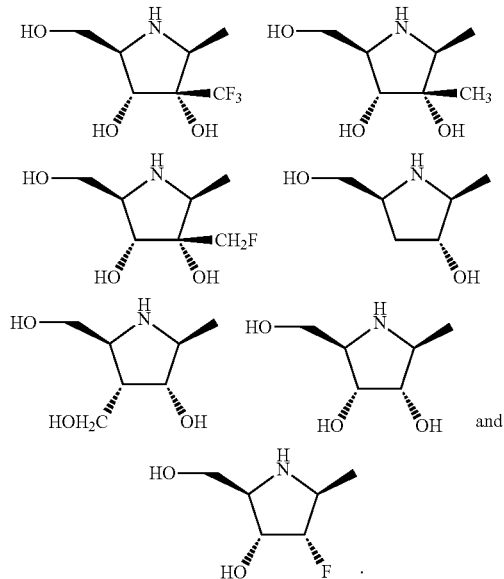

Group F

Examples of substituted dioxolane, substituted thioxolane and substituted dithiolane compounds include those compounds represented by the general structures:

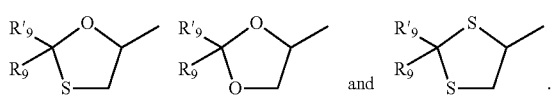

Specific examples include, but are not limited to, the following compounds:

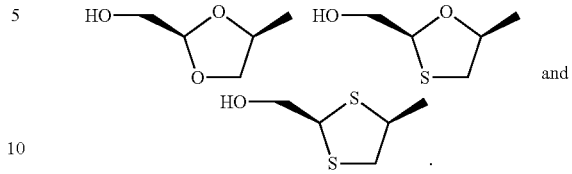

For the structures in Groups A-F, the following definitions apply:

$R_7$ is H, $OR_{14}$, $N_3$, $NH_2$, or F; and $R'_7$ is H, F, OH, O-alkyl, alkyl, substituted alkyl, alkenyl, substituted alkenyl, alkynyl, or substituted alkynyl; or $R_7$ and $R'_7$ together may be $=CH_2$, $=CHF$; wherein both $R_7$ and $R'_7$ are not OH; and when one of $R_7$ and $R'_7$ is $NH_2$, the other is not OH; and when one of $R_7$ and $R'_7$ is $N_3$, the other is not OH;

$R_8$ is H, $OR_{14}$, $N_3$, $NH_2$, or F; and $R'_8$ is H, F, OH, O alkyl, alkyl, substituted alkyl, alkenyl, substituted alkenyl, alkynyl, or substituted alkynyl; or $R_8$ and $R'_8$ together may be $=CH_2$, $=CHF$; wherein both $R_8$ and $R'_8$ are not OH; and when one of $R_8$ and $R'_8$ is $NH_2$, the other is not OH; and when one of $R_8$ and $R'_8$ is $N_3$, the other is not OH;

or $R_7$ and $R_8$ together can form

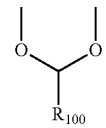

wherein: $R_{100}$ is $C_{1-12}$ alkyl $C_{3-8}$ cycloalkyl, aryl or heteroaryl; wherein any $C_{1-12}$ alkyl and $C_{3-8}$ cycloalkyl of $R_{100}$ is unsubstituted or is substituted with 1-3 substituents selected from halogen, hydroxy, carboxy, and $C_{1-4}$ alkoxy; and wherein any aryl or heteroaryl of $R_{100}$ is unsubstituted or is substituted with 1-5 substituents independently selected from $R_{100}$;

each $R_{101}$ is independently halo, $C_{1-4}$ alkyl, $C_{1-4}$ alkoxy, $C_{1-4}$ alkylthio, $C_{1-4}$ alkylsulfoyl, cyano, nitro, amino, phenyl, carboxy, trifluoromethyl, trifluoromethoxy, $C_{1-4}$ alkylamino, di($C_{1-4}$ alkyl)amino, $C_{1-4}$ alkanoyl, $C_{1-4}$ alkanoyloxy, or $C_{1-4}$ alkyloxycarbonyl;

$R_9$ is H, $CH_3$, $C_2H_5$, or $N_3$;

$R'_9$ is $CH_2OR_{14}$, $CH_2F$, $CH_2SH$, $CHFOH$, $CF_2OH$, $CH_2$-diphosphate, $CH_2$-triphosphate,

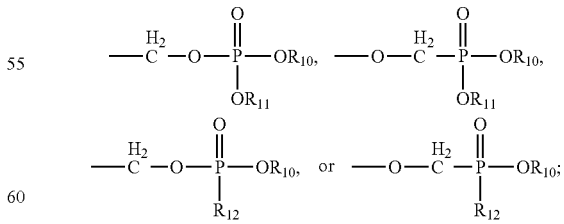

$R_{10}$ and $R_{11}$ are each independently H, alkyl, aryl, substituted aryl, acyloxyalkyl, or $(CH_2)_n$—O—$(CH_2)_mCH_3$;

$R_{12}$ is an N-linked amino acid residue (e.g. —NH—CH($CH_3$)$CO_2$alkyl or —NH—CH(isopropyl)-$CO_2$alkyl); and $R_{14}$ is H;

n is 2-5; and m is 10-20.

In one specific embodiment of the invention for the structures in Groups A-F:

$R_7$ is H, $OR_{14}$, $N_3$, $NH_2$, or F; and $R'_7$ is H, F, OH, O-alkyl, alkyl, substituted alkyl, alkenyl, substituted alkenyl, alkynyl, or substituted alkynyl; or $R_7$ and $R'_7$ together may be $=CH_2$, $=CHF$; wherein both $R_7$ and $R'_7$ are not OH; and when one of $R_7$ and $R'_7$ is $NH_2$, the other is not OH; and when one of $R_7$ and $R'_7$ is $N_3$, the other is not OH; $R_7''$ is alkyl or substituted alkyl.

$R_8$ is H, $OR_{14}$, $N_3$, $NH_2$, or F; and $R'_8$ is H, F, OH, O alkyl, alkyl, substituted alkyl, alkenyl, substituted alkenyl, alkynyl, or substituted alkynyl; or $R_8$ and $R'_8$ together may be $=CH_2$, $=CHF$; wherein both $R_8$ and $R'_8$ are not OH; and when one of $R_8$ and $R'_8$ is $NH_2$, the other is not OH; and when one of $R_8$ and $R'_8$ is $N_3$, the other is not OH;

$R_9$ is H, $CH_3$, $C_2H_5$, or $N_3$;

$R'_9$ is $CH_2OR_{14}$, $CH_2F$, $CH_2SH$, $CHFOH$, $CF_2OH$,

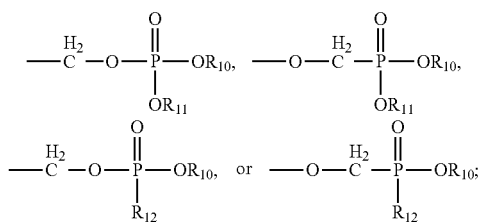

$R_{10}$ and $R_{11}$ are each independently H, alkyl, aryl, substituted aryl, acyloxyalkyl, or $(CH_2)_n\text{—}O\text{—}(CH_2)_mCH_3$;

$R_{12}$ is an N-linked amino acid residue (e.g. —NH—CH($CH_3$)$CO_2$alkyl or —NH—CH(isopropyl)-$CO_2$alkyl);

$R_{13}$ is H, $CH_3$, $C_2H_5$, $CH_2F$, $CH_2OH$, $CH_2CH_2F$, $CH_2CH_2OH$, $CH_2N_3$, $CH_2CH_2N_3$, $CH_2NH_2$, or $CH_2CH_2NH_2$;

$R_{14}$ is H;

n is 2-5; and m is 10-20.

In one embodiment, for a compound of Formula I, $R_{14}$ is replaced to form a pharmaceutically acceptable prodrug, for example, a prodrug selected from the group consisting of: acyl, oxyacyl, phosphonate, phosphate, phosphate esters, phosphonamidate, phosphorodiamidate, phosphoramidate mono ester, cyclic phosphoramidate, cyclic phosphorodiamidate, phosphoramidate diester, C(O) $CHR_{15}NH_2$,

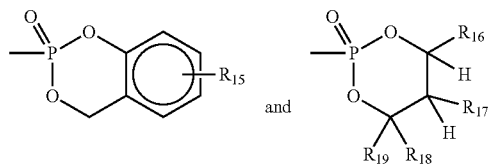

wherein:

$R_{15}$ is H, alkyl, substituted alkyl, aryl, substituted aryl, cycloalkyl, substituted cycloalkyl, heteroaryl, substituted heteroaryl, heterocyclic, substituted heterocyclic, or an amino acid;

$R_{16}$ is H, optionally substituted monocyclic aryl, or optionally substituted monocyclic heteroaryl; and $R_{17}$ is H, halogen, CN, —CO—$R_{20}$, —CON($R_{21}$)$_2$, —$CO_2R_{20}$, —$SO_2R_{20}$, —$SO_2N(R_{21})_2$, —$OR_{21}$, —$SR_{21}$, —$R_{21}$, —$N(R_{21})_2$, —O—$COR_{20}$, —O—$CO_2R_{20}$, —$SCOR_{20}$, —S—$CO_2R_{20}$, —$NHCOR_{21}$, —$NHCO_2R_{21}$, —$(CH_2)_p$—$OR_{22}$, or —$(CH_2)_p$—$SR_{22}$; or $R_{16}$ and $R_{17}$ are connected via an additional 3-5 atoms to form a cyclic group, optionally containing one heteroatom, that is fused to an aryl group at the beta and gamma position to the O attached to the phosphorus; or $R_{17}$ and $R_{18}$ are connected as described below;

$R_{18}$ and $R_{19}$ are each independently H, alkyl, aryl, heterocycloalkyl, aralkyl, optionally substituted monocyclic aryl or optionally substituted monocyclic heteroaryl; or $R_{18}$ and $R_{19}$ are connected via an additional 2-5 atoms to form a cyclic group, optionally containing 0-2 heteroatoms; or $R_{17}$ and $R_{18}$ are connected via an additional 3-5 atoms to form a cyclic group, optionally containing one heteroatom and $R_{19}$ is H, alkyl, aryl, heterocycloalkyl, aralkyl, optionally substituted monocyclic aryl or optionally substituted monocyclic heteroaryl; and $R_{20}$ is alkyl, aryl, heterocycloalkyl, or arylalkyl;

$R_{21}$ is H, alkyl, aryl, heterocycloalkyl, or arylalkyl;

$R_{22}$ is H or lower acyl; and p is an integer from 2-3.

Synthetic Processes

Processes for preparing compounds of Formula I, or a pharmaceutically acceptable salts or prodrugs thereof, as well as processes for preparing intermediate compounds that can be used to prepare compounds of Formula I or pharmaceutically acceptable salts or prodrugs thereof are provided as further embodiments of the invention. For example in one embodiment the invention provides a method for preparing a pharmaceutically acceptable salt of compound of Formula I comprising converting a corresponding compound of Formula I to the salt.

In another embodiment the invention provides a method for preparing a prodrug of a compound of Formula I comprising converting a corresponding compound of Formula I to the prodrug.

In another embodiment the invention provides a method for preparing a compound of Formula I comprising deprotecting a corresponding compound of Formula I that comprises one or more protecting groups to provide the compound of Formula I.

Synthetic Intermediates

The invention also provides synthetic intermediates that are useful for preparing compounds of Formula I or a salt or prodrug thereof. For example, the invention provides novel synthetic intermediates such as those described in the Examples herein.

Isomers and Physical Forms

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, tautomeric, or stereoisomeric form, or mixtures thereof, of a compound of the invention (e.g. a compound of Formula I, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine anti-viral or anti-cancer activity using the standard tests described herein, or using other similar tests which are well known in the art. Although the invention includes all isomeric forms of the compounds described herein, one embodiment of the invention provides compounds having the absolute stereochemistry depicted in the Examples hereinbelow.

Pharmaceutical Compositions, Modes of Administration and Methods of Treatment

The present disclosure provides compounds of the general Formula I as detailed above which are inhibitors of DNA and/or RNA viral polymerases and anticancer agents. Various forms of DNA and RNA viral polymerases are inhibited by the compounds disclosed, such as but not limited to viral RdRps. The compounds of the present disclosure therefore have utility in treating and/or preventing viral infections in a host and in treatment and/or preventing a variety of disease states and/or conditions caused by or related to such viral infections. In one embodiment, the compounds are useful in the above mentioned treating and/or preventing by inhibiting a viral RNA and DNA polymerases. Such viral agents include, but are not limited to, hepatitis B, hepatitis C, human immunodeficiency virus, Polio, Coxsackie A and B, Rhino, Echo, small pox, Ebola, and West Nile virus. In a particular embodiment, the causative agent of the viral infection is a flavivirus.

The present disclosure provides for a compound of the general Formula I and a pharmaceutical composition comprising a pharmaceutically effective amount of at least one compound of general Formula I as described herein. Such compounds and/or pharmaceutical compositions may be used in the manufacture of a medicament for treating and/or preventing a disease or condition in which it is desirable to inhibit a viral RNA and DNA polymerases. Such pharmaceutical compositions may also comprise a pharmaceutically acceptable carrier and other ingredients known in the art, or may comprise solely a compound of the general Formula I.

The pharmaceutically acceptable carriers described herein, including, but not limited to, vehicles, adjuvants, excipients, or diluents, are well-known to those who are skilled in the art. Typically, the pharmaceutically acceptable carrier is chemically inert to the active compounds and has no detrimental side effects or toxicity under the conditions of use. The pharmaceutically acceptable carriers can include polymers and polymer matrices.

The compounds described in the instant disclosure can be administered by any conventional method available for use in conjunction with pharmaceuticals, either as individual therapeutic agents or in combination with additional therapeutic agents.

The compounds described are administered in a pharmaceutically effective amount. The pharmaceutically effective amount of the compound and the dosage of the pharmaceutical composition administered will, of course, vary depending upon known factors, such as the pharmacodynamic characteristics of the particular agent and its mode and route of administration; the age, health and weight of the recipient; the severity and stage of the disease state or condition; the kind of concurrent treatment; the frequency of treatment; and the effect desired.

A daily dosage of active ingredient can be expected to be about 0.001 to 1000 milligrams (mg) per kilogram (kg) of body weight per day. In one embodiment, the total amount is between about 0.1 mg/kg and about 100 mg/kg of body weight per day; in an alternate embodiment between about 1.1 mg/kg and about 50 mg/kg of body weight per day; in yet another alternate embodiment between 0.1 mg/kg and about 30 mg/kg of body weight per day. The above described amounts may be administered as a series of smaller doses over a period of time if desired. The pharmaceutically effective amount can be calculated based on the weight of the parent compound to be delivered. If the salt or prodrug exhibits activity in itself, the pharmaceutically effective amount can be estimated as above using the weight of the salt or prodrug, or by other means known to those skilled in the art. The dosage of active ingredient may be given other than daily if desired.

The total amount of the compound administered will also be determined by the route, timing and frequency of administration as well as the existence, nature, and extent of any adverse side effects that might accompany the administration of the compound and the desired physiological effect. It will be appreciated by one skilled in the art that various conditions or disease states, in particular chronic conditions or disease states, may require prolonged treatment involving multiple administrations.

Dosage forms of the pharmaceutical compositions described herein (forms of the pharmaceutical compositions suitable for administration) contain from about 0.1 mg to about 3000 mg of active ingredient (i.e. the compounds disclosed) per unit. In these pharmaceutical compositions, the active ingredient will ordinarily be present in an amount of about 0.5-95% weight based on the total weight of the composition. Multiple dosage forms may be administered as part of a single treatment. The active ingredient may be administered to achieve peak plasma concentrations of the active ingredient of from about 0.2 to 70 µM, or from about 1.0 to 10 µM.

The active ingredient can be administered orally in solid dosage forms, such as capsules, tablets, and powders, or in liquid dosage forms, such as elixirs, syrups and suspensions. It can also be administered parenterally, in sterile liquid dosage forms. The active ingredient can also be administered intranasally (nose drops) or by inhalation via the pulmonary system, such as by propellant based metered dose inhalers or dry powders inhalation devices. Other dosage forms are potentially possible such as administration transdermally, via patch mechanisms or ointment.

Formulations suitable for oral administration can include (a) liquid solutions, such as a pharmaceutically effective amount of the compound dissolved in diluents, such as water, saline, or orange juice; (b) capsules, sachets, tablets, lozenges, and troches, each containing a predetermined pharmaceutically effective amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, propylene glycol, glycerin, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of the following: lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acadia, emulsions, and gels containing, in addition to the active ingredient, such carriers as are known in the art.

Formulations suitable for parenteral administration include aqueous and non-aqueous, isotonic sterile injection solutions, which can contain anti-oxidants, buffers, bacteriostats, and solutes that render the formulation isotonic with the blood of the patient, and aqueous and non-aqueous sterile suspensions that can include suspending agents, solubilizers, thickening agents, stabilizers, and preservatives.

The compound can be administered in a physiologically acceptable diluent in a pharmaceutically acceptable carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol such as poly(ethyleneglycol) 400, glycerol ketals, such as 2,2-dimethyl-1,3-dioxolane-4-methanol, ethers, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations, include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyldialkylammonium halides, and alkylpyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene polypropylene copolymers, (d) amphoteric detergents such as, for example, alkyl.beta.-aminopropionates, and 2-alkylimidazoline quaternary ammonium salts, and (e) mixtures thereof.

The parenteral formulations typically contain from about 0.5% to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol.

Pharmaceutically acceptable excipients are also well-known to those who are skilled in the art. The choice of excipient will be determined in part by the particular compound, as well as by the particular method used to administer the composition. Accordingly, there is a wide variety of suitable formulations of the pharmaceutical composition of the present invention. The following methods and excipients are merely exemplary and are in no way limiting. The pharmaceutically acceptable excipients preferably do not interfere with the action of the active ingredients and do not cause adverse side-effects. Suitable carriers and excipients include solvents such as water, alcohol, and propylene glycol, solid absorbants and diluents, surface active agents, suspending agent, tableting binders, lubricants, flavors, and coloring agents.

The compounds of the present invention, alone or in combination with other suitable components, can be made into aerosol formulations to be administered via inhalation. These aerosol formulations can be placed into pressurized acceptable propellants, such as dichlorodifluoromethane, propane, and nitrogen. Such aerosol formulations may be administered by metered dose inhalers. They also may be formulated as pharmaceuticals for non-pressured preparations, such as in a nebulizer or an atomizer.

The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets. The requirements for effective pharmaceutically acceptable carriers for injectable compositions are well known to those of ordinary skill in the art. See Pharmaceutics and Pharmacy Practice, J.B. Lippincott Co., Philadelphia, Pa., Banker and Chalmers, Eds., 238-250 (1982) and ASHP Handbook on Injectable Drugs, Toissel, 4th ed., 622-630 (1986).

Formulations suitable for topical administration include pastilles comprising the active ingredient in an inert base, such as gelatin and glycerin, or sucrose and acacia, as well as creams, emulsions, and gels containing, in addition to the active ingredient, such carriers as are known in the art. Furthermore, transdermal patches can be prepared using methods known in the art.

Additionally, formulations suitable for rectal administration may be presented as suppositories by mixing with a variety of bases such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

One skilled in the art will appreciate that suitable methods of administering a compound of the present invention to an patient are available, and, although more than one route can be used to administer a particular compound, a particular route can provide a more immediate and more effective reaction than another route.

Useful embodiments of pharmaceutical dosage forms for administration of the compounds according to the present invention can be illustrated as follows.

A large number of hard-shell capsules are prepared by filling standard two-piece hard gelatine capsules each with 100 mg of powdered active ingredient, 150 mg of lactose, 50 mg of cellulose and 6 mg of magnesium stearate.

A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

A large number of tablets are prepared by conventional procedures so that the dosage unit is 100 mg of active ingredient, 0.2 mg of colloidal silicon dioxide, 5 mg of magnesium stearate, 275 mg of microcrystalline cellulose, 11 mg of starch, and 98.8 mg of lactose. Appropriate aqueous and non-aqueous coatings may be applied to increase palatability, improve elegance and stability or delay absorption.

Immediate release tablets/capsules are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Moreover, the compounds of the present invention can be administered in the form of nose drops, or metered dose and a nasal or buccal inhaler. The drug is delivered from a nasal solution as a fine mist or from a powder as an aerosol.

In one embodiment, the teachings of the present disclosure provide for the use of such pharmaceutical compositions and medicaments in a method of treating a viral infection or treating a disease state and/or condition caused by or related to such viral infection. In one embodiment, the treatment is the result of the inhibition of a viral RNA or DNA polymerase, such as but not limited to a RdRp. Such treatment or inhibition need not be complete to be useful. The method of treatment comprises the steps of: (i) identifying a patient in need of such treatment; (ii) providing such pharmaceutical composition containing at least one compound of the invention; and (iii) administering such pharmaceutical composition in a therapeutically effective amount to treat the viral infection in a patient in need of such treatment or to inhibit the activity of a viral RNA or DNA polymerase in a patient in need of such treatment.

In one embodiment, the teachings of the present disclosure provide for the use of such pharmaceutical compositions and medicaments in a method of preventing or suppressing a viral infection or preventing or suppressing a disease state and/or condition caused by or related to such viral infection. In one embodiment, the prevention or suppression is the result of the inhibition of a viral RNA or DNA polymerase, such as but not limited to a RdRp. Such prevention, suppression or inhibition need not be complete to be useful. The method of preventing or suppressing can optionally comprises the steps of: (i) identifying a patient in need of such prevention; (ii) providing such pharmaceutical composition containing at least one compound of the general Formula I; and (iii) administering such pharmaceutical composition in a therapeutically effective amount to prevent or suppress the viral infection in a patient in need of such treatment or to inhibit the activity of a viral RNA and DNA polymerase in a patient in need of such treatment.

The methods of the treating and preventing a viral infection or a disease state and/or condition caused by or related to said viral infection may further comprise administering a therapeutically effective amount of a compound of the present invention in combination with a therapeutically effective amount of another anti-viral agent which, in particular, may be active against HCV. Agents active against HCV include, but are not limited to, ribavirin, levovirin, viramidine, thymosin alpha-1, an inhibitor of HCV NS3 serine protease, an inhibitor of inosine monophosphatedehydrognease, interferon-α, pegylated interferon-α (peginterferon-α), a combination of interferon-α and ribavirin, a combination of peginterferon-α and ribavirin, a combination of interferon-α and levovirin, and a combination of peginterferon-α and levovirin. Interferon-α includes, but is not limited to, recombinant interferon-α2a, interferon-α2b, a consensus interferon, and a purified interferon-α product.

The compounds and pharmaceutical compositions of the present disclosure can be administered to patients to prevent and/or treat a number of cancers. Cancers include, but are not limited to, leukemias and lymphomas such as acute lymphocytic leukemia, acute nonlymphocytic leukemias, chronic lymphocytic leukemia, chronic myelogenous leukemia, Hodgkin's Disease, non-Hodgkin's lymphomas, and multiple myeloma, childhood solid tumors such as brain tumors, neuroblastoma, retinoblastoma, Wilms Tumor, bone tumors, and soft-tissue sarcomas, common solid tumors of adults such as lung cancer, colon and rectum cancer, breast cancer, prostate cancer, urinary cancers, uterine cancers, oral cancers, pancreatic cancer, melanoma and other skin cancers, stomach cancer, ovarian cancer, brain tumors, liver cancer, laryngeal cancer, thyroid cancer, esophageal cancer, and testicular cancer. The cancer may be related to a viral infection or an activity of a viral DNA or RNA polymerase.

The methods of the treating and preventing cancer may also comprises further administering of a chemotherapeutic agent in combination with any of the compounds or pharmaceutical compositions of the present disclosure. Any suitable chemotherapeutic agent can be employed for this purpose. The chemotherapeutic agent is typically selected from the group consisting of alkylating agents, antimetabolites, natural products, hormonal agents, and miscellaneous agents.

Examples of alkylating chemotherapeutic agents include carmustine, chlorambucil, cisplatin, lomustine, cyclophosphamide, melphalan, mechlorethamine, procarbazine, thiotepa, uracil mustard, triethylenemelamine, busulfan, pipobroman, streptozocin, ifosfamide, dacarbazine, carboplatin, and hexamethylmelamine.

Examples of chemotherapeutic agents that are antimetabolites include cytosine arabinoside, fluorouracil, gemcitabine, hydroxyurea, mercaptopurine, methotrexate, azaserine, thioguanine, floxuridine, fludarabine, cladribine and L-asparaginase.

Examples of chemotherapeutic agents that are natural products include actinomycin D, bleomycin, camptothecins, daunomycin, doxorubicin, etoposide, mitomycin C, TAXOL™ (paclitaxel), taxotere, teniposide, vincristine, vinorelbine, mithramycin, idarubicin, MITHRACIN™. (plicamycin), and deoxycoformycin.

An example of a hormonal chemotherapeutic agent includes tamoxifen. Examples of the aforesaid miscellaneous chemotherapeutic agents include mitotane, mitoxantrone, vinblastine, and levamisole.

The ability of a compound to inhibit viral polymerases can be evaluated using known assays. The ability of a compound to inhibit HCV NS5B polymerase can be evaluated using the following assay.

HCV NS5B Polymerase Assay

Antiviral activity of the test compounds was assessed (Okuse et al., Antiviral Res. 2005, 65, 23-34) in the stably HCV RNA-replicating cell line, AVA5, derived by transfection of the human hepatoblastoma cell line, Huh7 (Blight et al., Sci. 2000, 290, 1972). Compounds were added to dividing cultures once daily for three days. Media was changed with each addition of compound. Cultures generally started the assay at 30-50% confluence and reached confluence during the last day of treatment. Intracellular HCV RNA levels and cytotoxicity were assessed 24 hours after the last dose of compound.

Triplicate cultures for HCV RNA levels (on 48-well and 96-well plates) and cytotoxicity (on 96-well plates) were used. A total of six untreated control cultures, and triplicate cultures treated with α-interferon and ribavirin served as positive antiviral and toxicity controls.

Intracellular HCV RNA levels were measured using a conventional blot hybridization method in which HCV RNA levels are normalized to the levels of B-actin RNA in each individual culture (Okuse et al, Antivir. Res. 2005, 65, 23-34). Cytotoxicity was measured using a neutral red dye uptake assay (Korbai and Gerin, Antivir. Res. 1992, 19, 55). HCV RNA levels in the treated cultures are expressed as a percentage of the mean levels of RNA detected in untreated cultures.

Representative compounds of Formula I demonstrated significant activity in this assay.

compound Synthesis

Compound of Formula I can be prepared using synthetic intermediates and synthetic procedures that are known, or they can be prepared using the synthetic intermediates and synthetic procedures described herein, for example, as described in the following Schemes.

The following abbreviations are used herein.
Tr: trityl
Bn: benzyl
TBDPS: tert-butyldiphenylsilyl
m-CPBA: 3-chloroperoxybenzoic acid
TFA: trifluoroacetic acid
TBDMSCl: tert-butyldimethylsilyl chloride
DMF: dimethylformamide
THF: tetrahydrofuran
LDA: lithium diisopropylamine
TEAB: triethylammonium bicarbonate
MmTrCl: monomethoxytrityl chloride
MMTrCl: monomethoxytrityl chloride
DMAP: dimethylaminopyridine
DEAE: diethylaminoethyl-sepharose
CMA-80: Chloroform 80:MeOH 18: $NH_4OH$:2
CMA-50: Chloroform 50:MeOH 40: $NH_4OH$:10
Bz: benzoyl
BnBr: benzyl bromide
LiHMDS: lithium hexamethyldisalazane
TBDPSCl: tert-butyldiphenylsilyl chloride
DMSO: dimethylsulfoxide
RMgBr: alkyl magnesium bromide
DIBAL: diisobutylaluminum hydride
DBN: 1,5-diazabicyclo[4.3.0]non-5-ene
DBU: 1,8-diazabicyclo[5.4.0]undec-7-ene
MeMgBr: methylmagnesium bromide
P: Represents a suitable protecting group

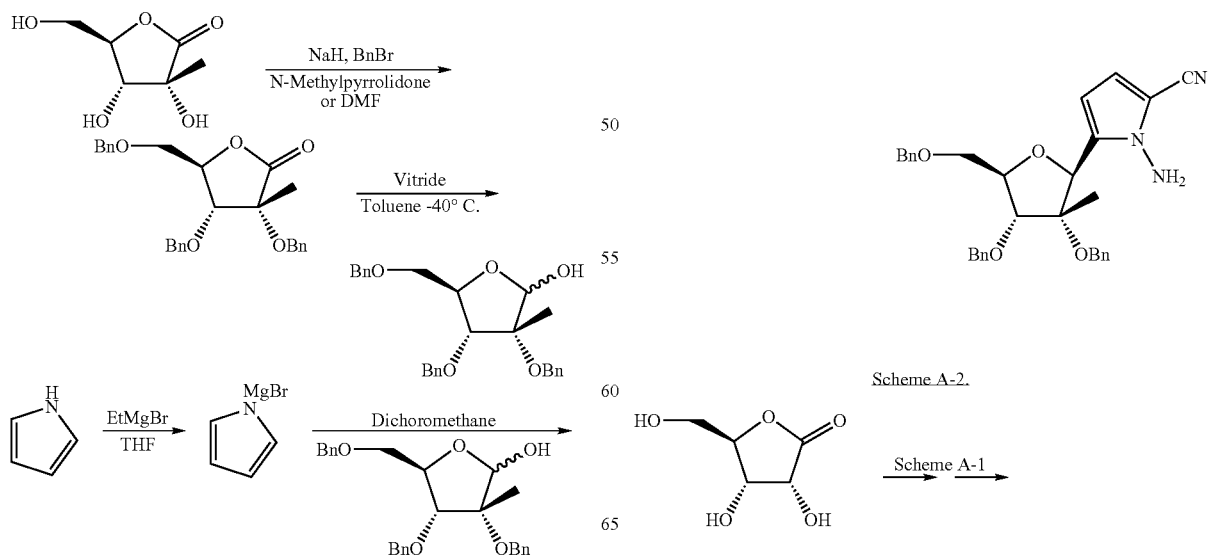

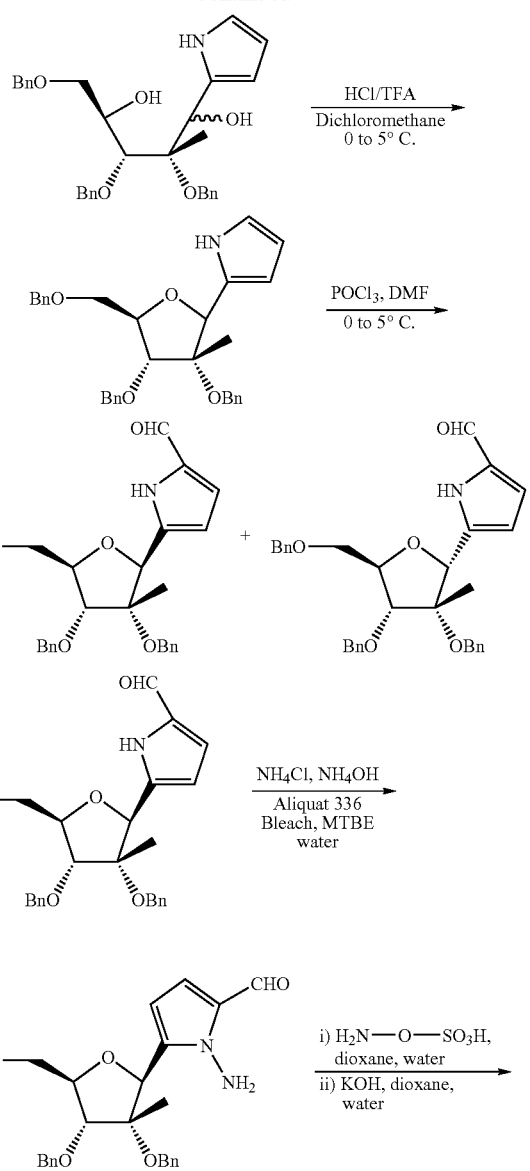

29
-continued

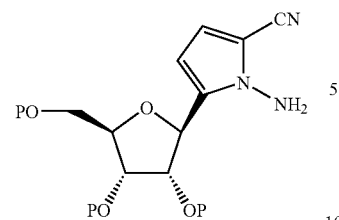

Compounds without 2'-C-methyl are prepared in the same way as given in Scheme A-1 starting from ribonolactone or ribose with minor modifications.

Scheme A-3.

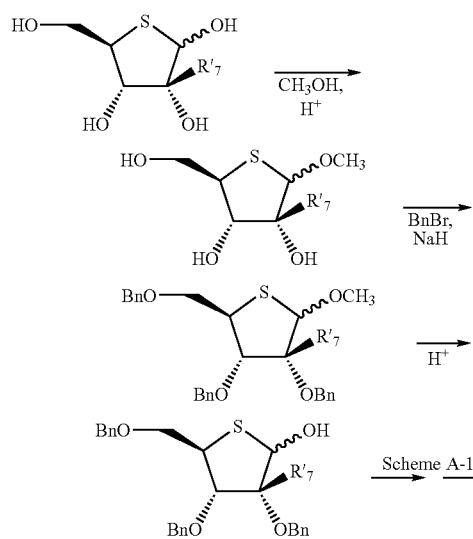

Compounds with S in the ring and with/without 2'-CH₃ are prepared in the same way as given in Scheme A-1 with minor modifications.
R'₇ = H, CH₃, etc.

Scheme A-4.

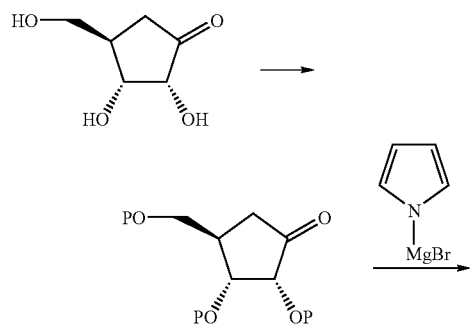

30
-continued

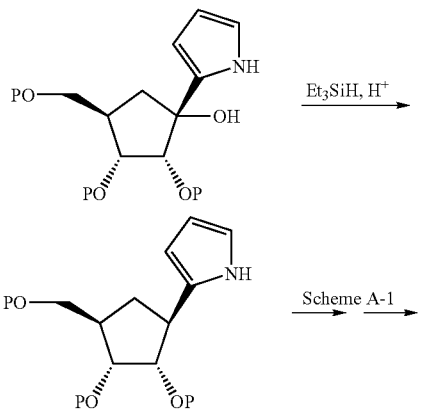

Scheme A-5.

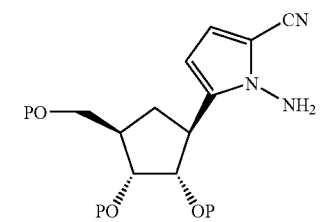

Compounds with cyclopentane ring are prepared starting from suitably protected cyclopentanone derivative.

Compounds with pyrrolidine ring system are prepared by the following route.

The imine can be prepared using standard procedures described in the literature.

Scheme A-6.

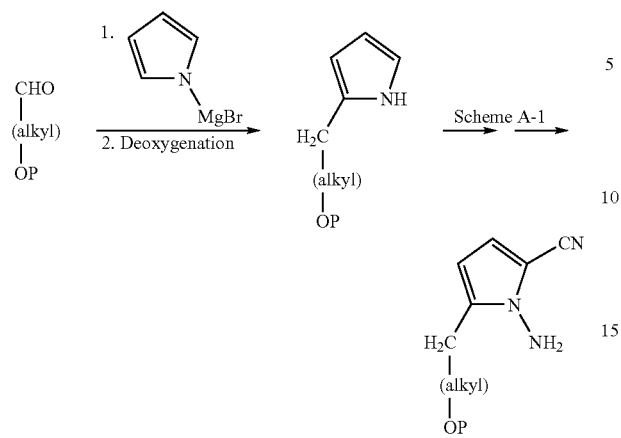

Compounds with alkyl side chain are also prepared the same way as given in Scheme A-1 starting from the corresponding aldehyde.

The compounds with modified ribose (such as 2-deoxyribose, 2-fluoro-2-deoxyribose, arabinose, 2,2'-difluoro-2-deoxyribose, 3-deoxyribose, 2,3-dideoxyribose, 2,3-dideoxydidehydroribose, 4-azidoribose, etc.), thiaribose, pyrrolidine, cyclopentane ring systems are prepared from well known procedures in the literature and are converted to the desired precursor with amino and cyano group in the pyrrole ring according to Scheme A-1.

Scheme B-1.

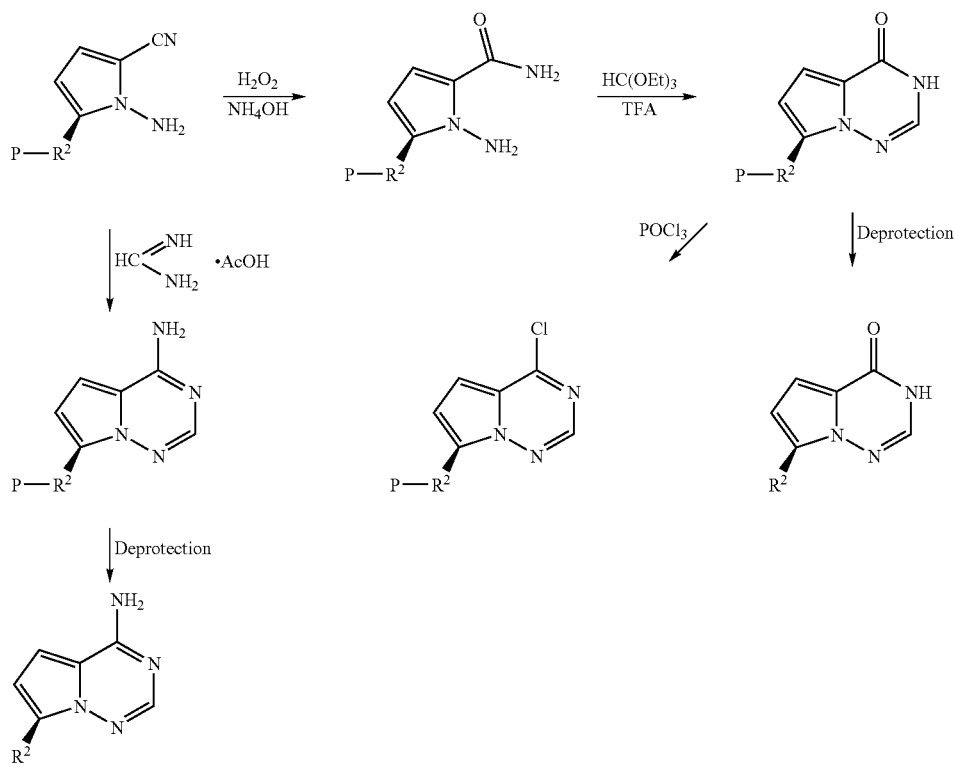

Protecting group (P) could be any suitable group which can be deprotected under normal conditions without affecting other groups in the molecule or the molecule itself.

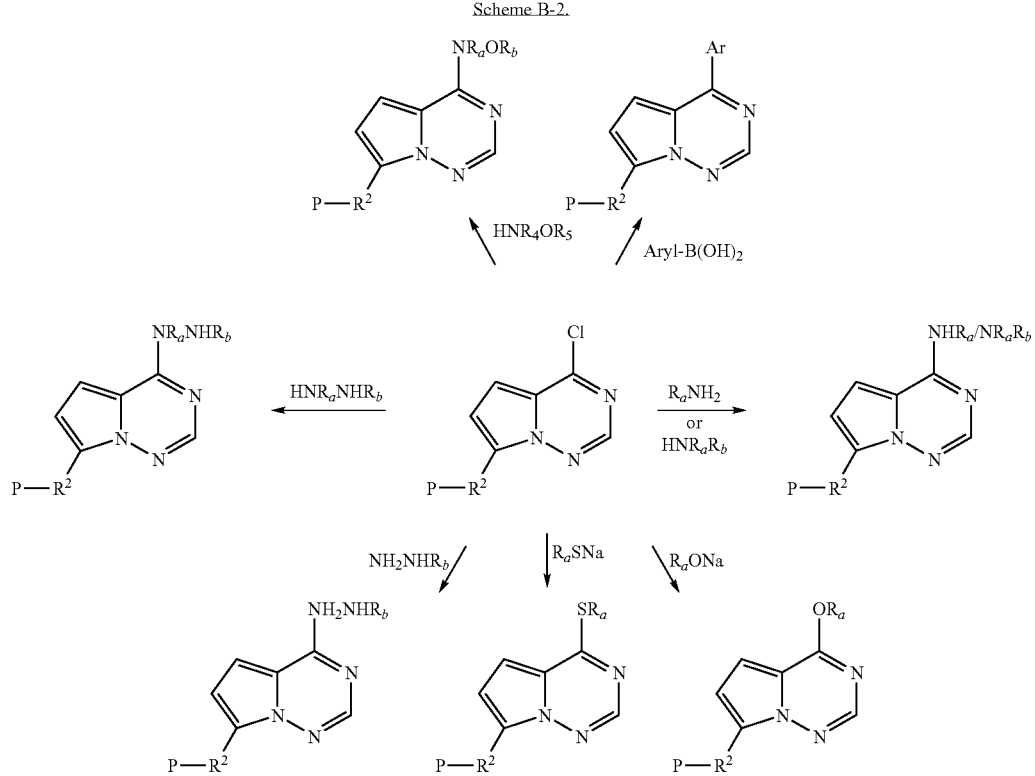
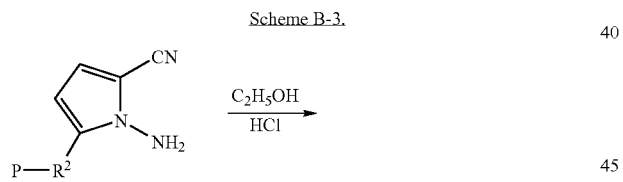
Compounds with R substituent in structure (I) are prepared by the following Scheme. Some examples of the groups are given in this Scheme.
Removal of protecting groups "P" provides compounds of the invention
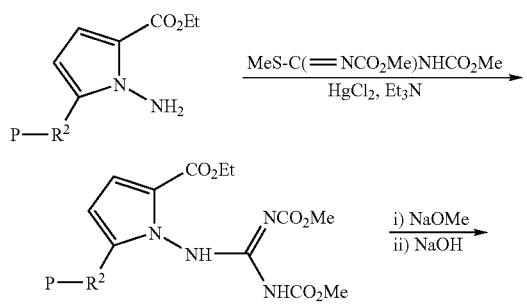
-continued
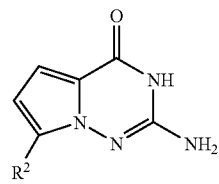
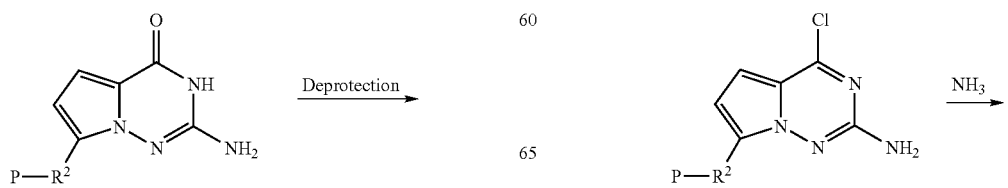

35
-continued
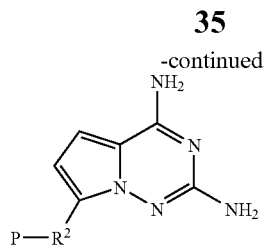
→ Deprotection →
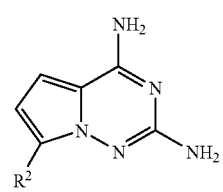
Scheme B-5.
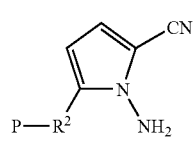 → Et₃N, H₂S →
36
-continued
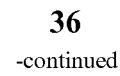
→ CH(OEt)₃ →
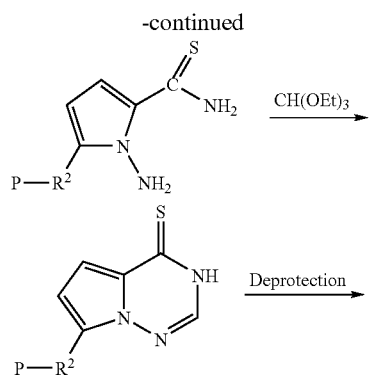
→ Deprotection →
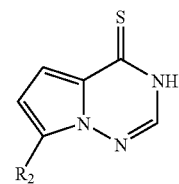
Scheme B-6.
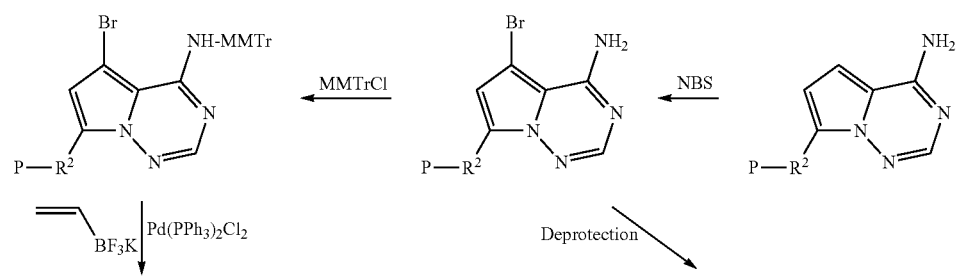
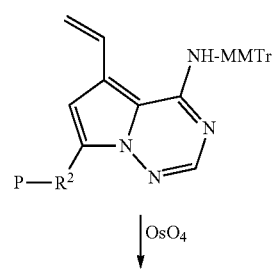
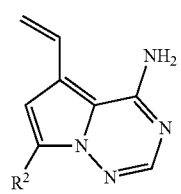
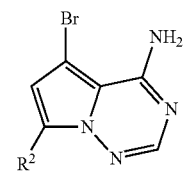
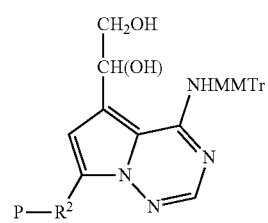
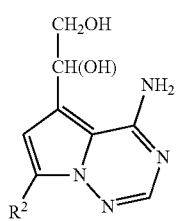
Compounds with R³ substituent in structure (I) are prepared by the following Schemes Scheme B-7.
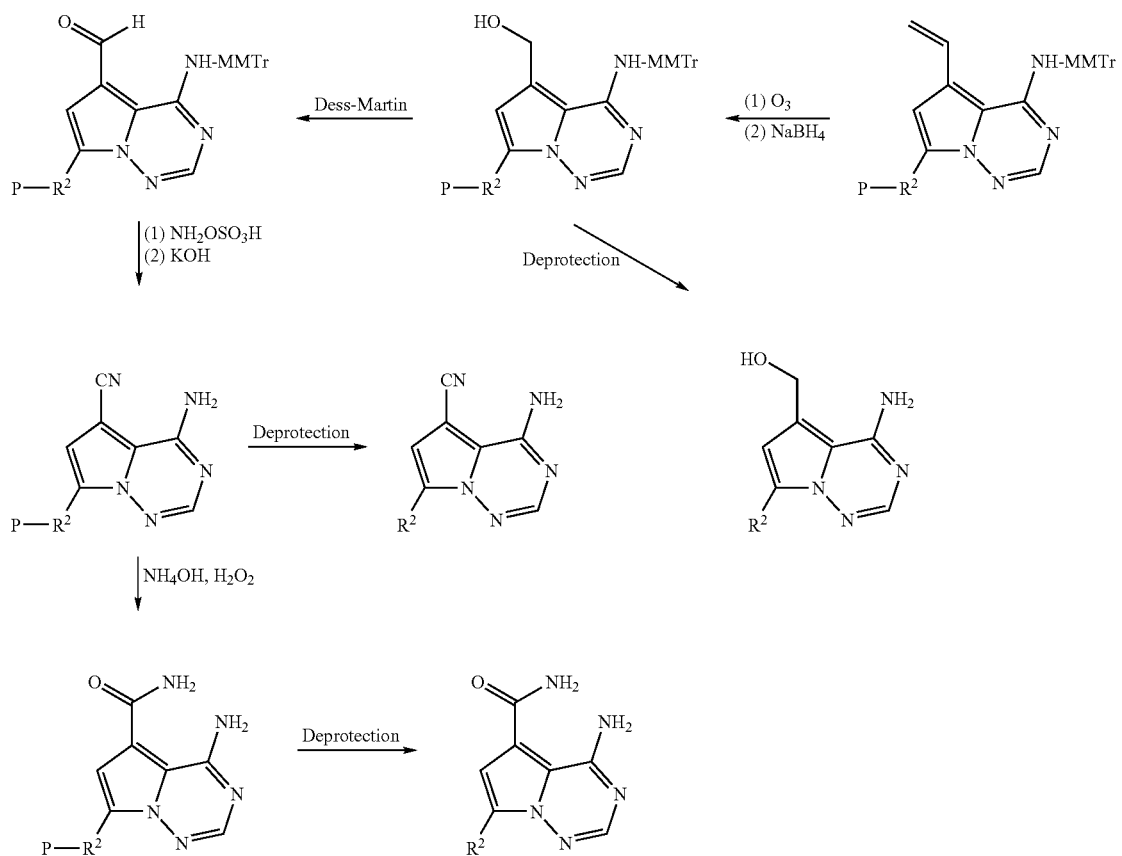
Scheme B-8.
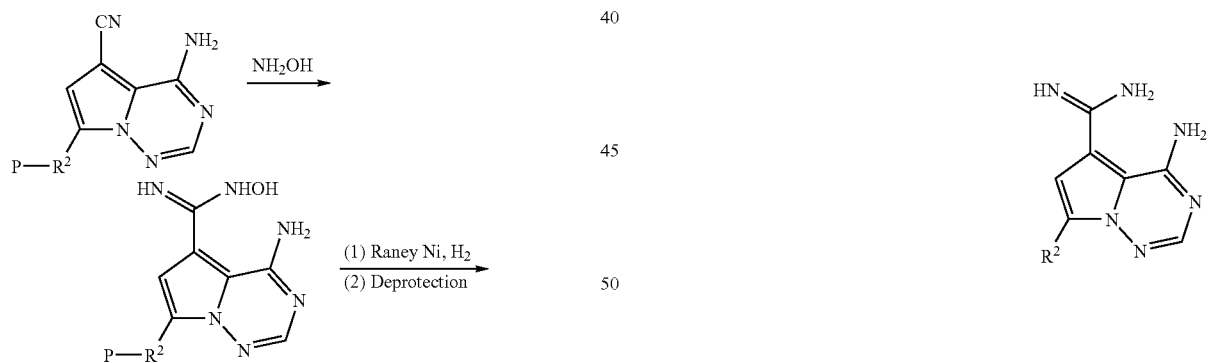
Scheme B-9.
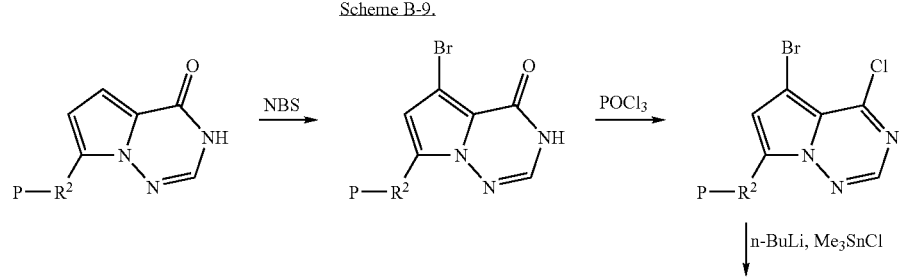

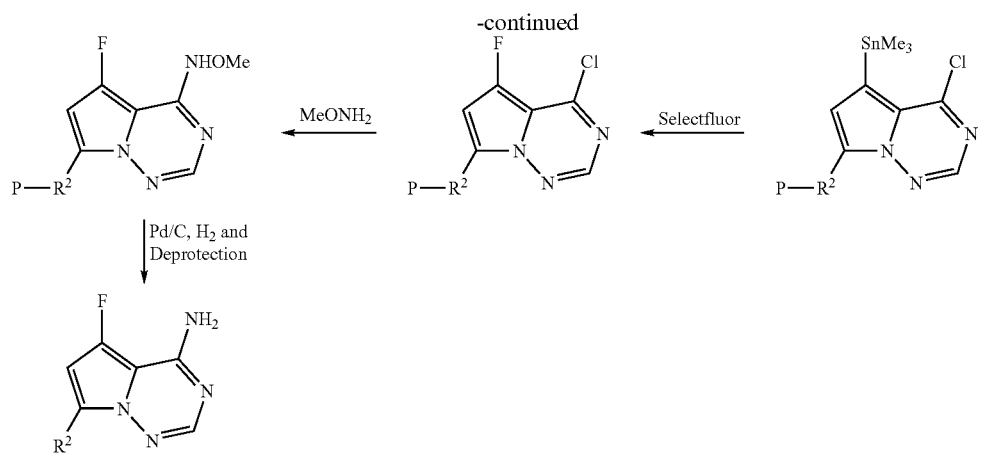
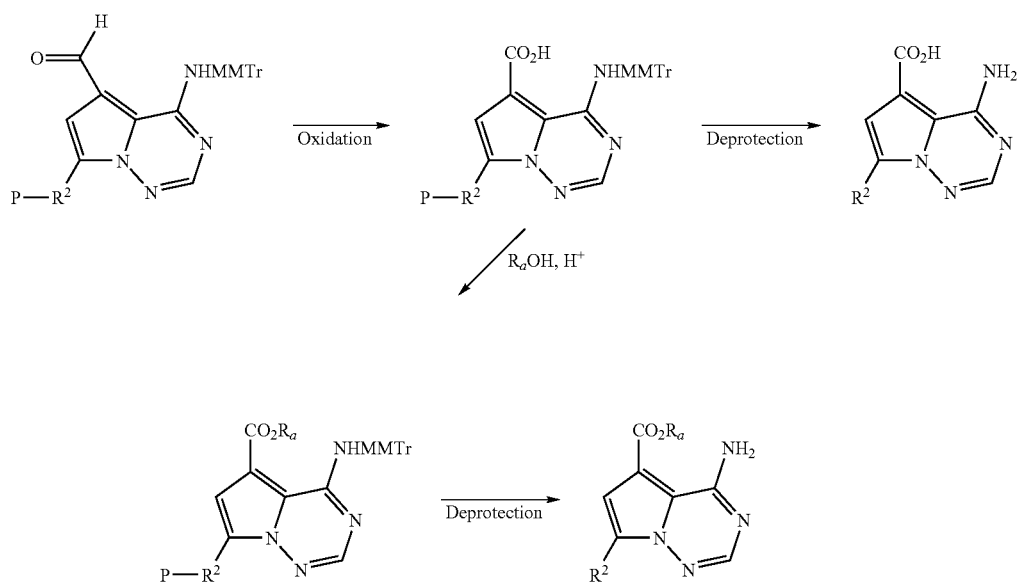
Scheme B-10.
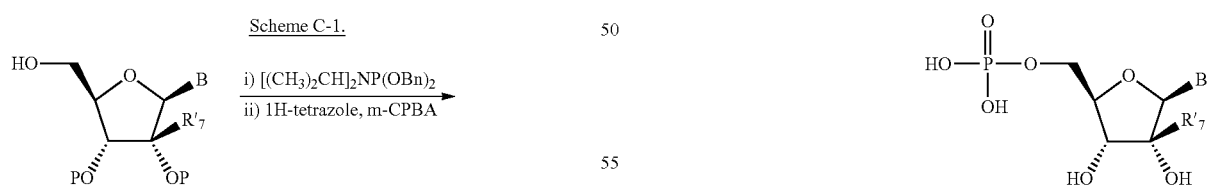
Scheme C-1.
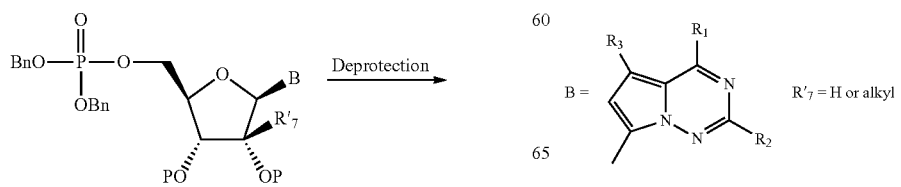
Preparation of phosphates, phosphonates and triphosphates.
$R'_7$ = H or alkyl Scheme C-2.

B and R'$_7$ are the same as in Scheme C-1

Scheme C-3.

Prodrugs of such phosphonates can be prepared by literature procedures.

Schemes D-1 and D-2 illustrate the preparation of prodrugs of the invention.

Scheme D-1.

B and R'$_7$ are the same as in scheme C-1
R'=aminoacid ester

Scheme D-2.

B and R'$_7$ are the same as in scheme C-1
R'=CH$_3$, C(CH$_3$)$_3$

Scheme E-1.

(Scheme B-9)

43
-continued
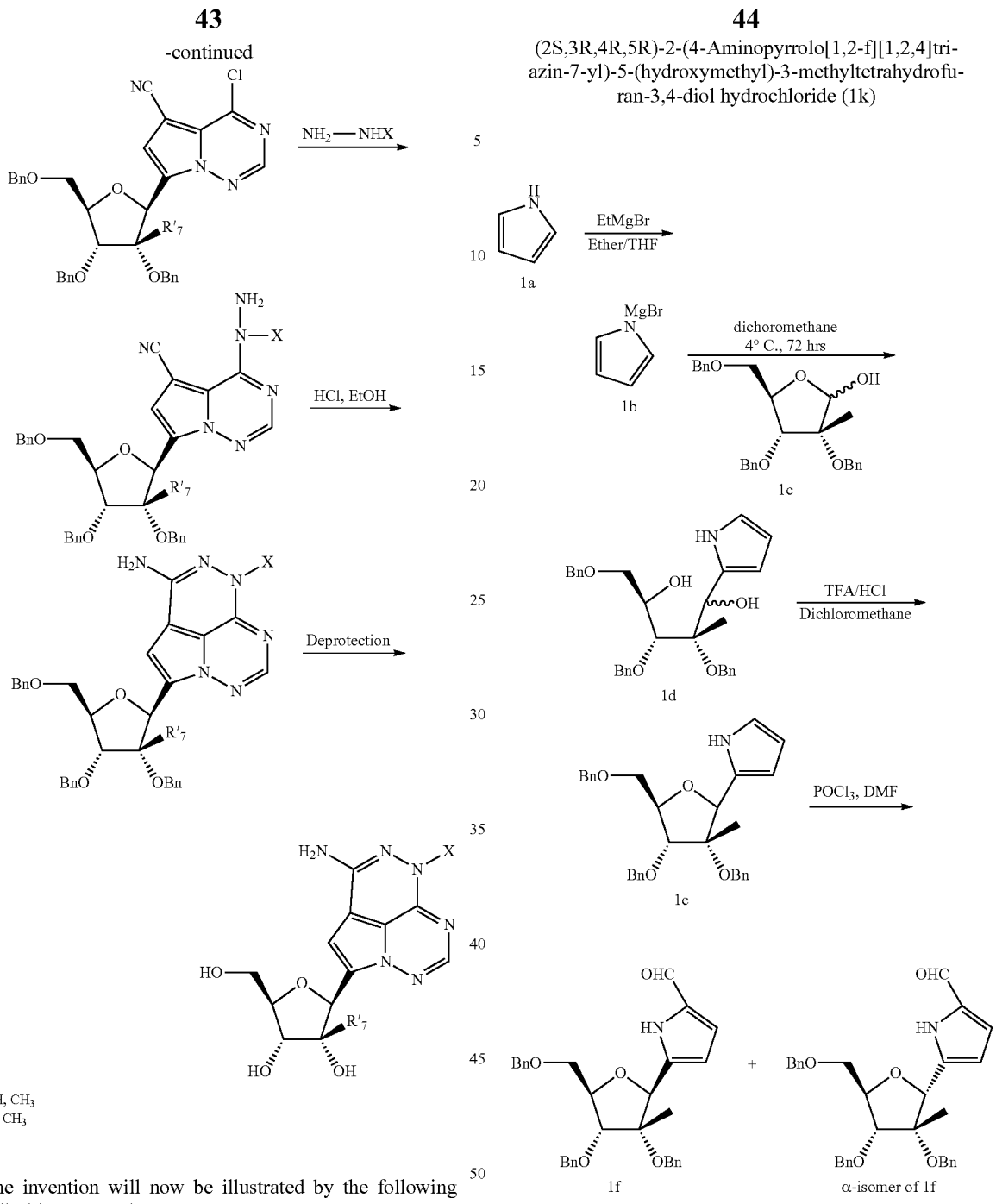
R'7 = H, CH3
X = H, CH3
The invention will now be illustrated by the following non-limiting Examples.
Example 1
44
(2S,3R,4R,5R)-2-(4-Aminopyrrolo[1,2-f][1,2,4]triazin-7-yl)-5-(hydroxymethyl)-3-methyltetrahydrofuran-3,4-diol hydrochloride (1k)
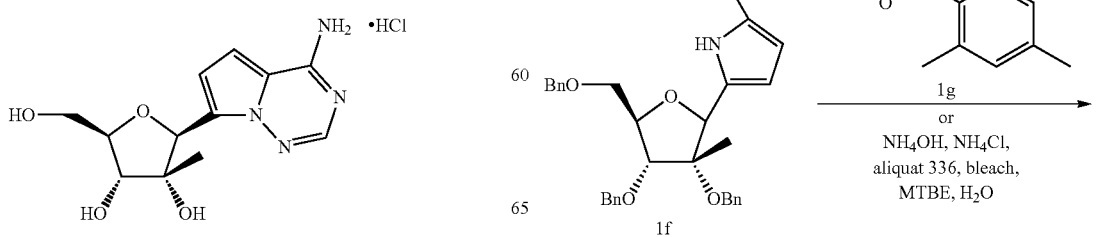

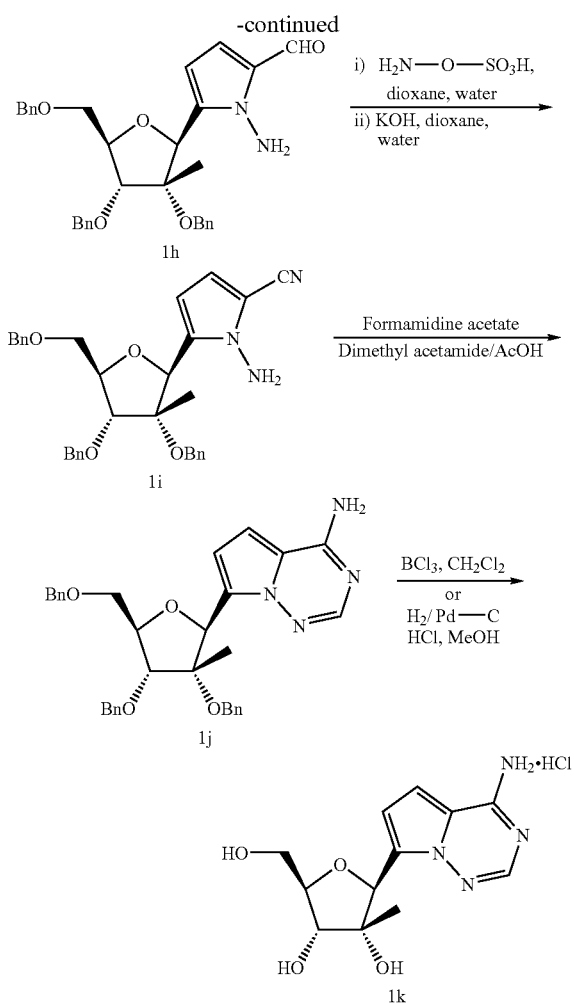

a. To a stirred solution of freshly distilled pyrrole (6.79 g, 100.89 mmol) in diethyl ether (100 mL) was added ethyl magnesium bromide (33.6 mL, 100.89 mmol, 3M solution in ether) slowly at 20° C. The reaction mixture was further stirred at 20° C. for 1 h and the solvent was removed under vacuum to give 1b. To 1b in dichloromethane (500 mL) at 0° C. was added a solution of (3R,4R,5R)-3,4-bis(benzyloxy)-5-(benzyloxymethyl)-3-methyltetrahydrofuran-2-ol (1c, WO 2006/050161, 10.96 g, 25.22 mmol) in dichloromethane (100 mL) and further stirred at 4° C. for 72 h. The reaction mixture was quenched by adding saturated solution of ammonium chloride (200 mL) and organic layer was separated. The aqueous layer was further extracted with dichloromethane (2×200 mL). The combined organic extracts were washed with water (2×50 mL) and brine (1×50 mL) and dried over MgSO$_4$. After filtration, the filtrate containing 1d was treated with trifluoroacetic acid (4.14 g, 36.34 mmol) at 20° C. and stirred for 14 h. The reaction mixture was washed with water (2×100 mL) and brine (1×50 mL) and dried (MgSO$_4$). After filtration, the filtrate was concentrated to give 12.5 g of crude 1e.

NOTE: THF was also used to make Grignard reagent instead of diethyl ether. THF was removed by distillation and the traces by azeotroping with toluene.

b. Phosphorousoxy chloride (19.33 g, 126.1 mmol) was added to N,N-dimethylformamide (100 mL) at 0° C. and stirred for 30 min. To this solution was added 1e (12.1 g, 25.22 mmol) in dichloromethane (50 mL) slowly over a period of 15 min. at 0° C. and stirring was continued for 1 h. The reaction mixture was quenched by adding saturated solution of sodium acetate (100 mL) and stirred for 30 min. The reaction mixture was concentrated to remove dichloromethane and the residue was diluted with ethyl acetate (200 mL). The organic layer was separated and washed with water (2×100 mL) and brine (1×50 mL) and dried (MgSO$_4$). After filtration, the filtrate was concentrated and the residue was purified by flash chromatography using ethyl acetate in hexanes (0 to 12%) to give 2.92 g (22.6% from 1c) of 1f as dark brown syrup. MS (ES$^-$): 510.2 (M−H)$^-$.

NOTE: Only DMF was also used as solvent; there was no need of dichloromethane. For workup, 2N NaOH was used in place of sodium acetate.

c. To a stirred solution of above obtained 1f (2.5 g, 4.88 mmol) in tetrahydrofuran (50 mL) was added sodium hydride (0.39 g, 9.77 mmol, 60% dispersion in mineral oil) at 0° C. After stirring for 30 min at 0° C., O-(mesitylsulfonyl)hydroxylamine (1g, 1.15 g, 5.37 mmol, prepared by the method of Krause, J. G. *Synthesis*, 1972, 140) was added at 0° C. and further stirred for 2 h. The reaction mixture was quenched by adding water (20 mL) and extracted with ethyl acetate (2×50 mL). The combined organic extracts were washed with water (2×25 mL) and brine (1×25 mL) and dried (MgSO$_4$). After filtration, the filtrate was concentrated to give 2.75 g of 1 h as dark syrup. MS (ES$^+$): 527.43 (M+H)$^+$.

The compound 1h can also be prepared as follows.

d. Aldehyde 1f (5.2 Kg, 10.16 moles) was dissolved in methyl tert-butyl ether (72.8 L) and charged into a clean SS reactor (600 L). Aliquot 336 (0.25 Kg, 0.61 mole) and ammonium chloride (6.53 Kg, 122.07 moles) were added to the reactor and reaction mixture was cooled to 0-5° C. Ammonium hydroxide (19.08 L, 137 moles, 28% solution in water) was added at 0-5° C. followed by addition of a cold (0-5° C.) sodium hydroxide solution (16.59 Kg in 66 L water, 414.75 moles) at the same temperature over a period of 3 h. Sodium hypochlorite (251 L, 222.58 moles, 6% solution) addition was started at 0° C. and during the addition the temperature was allowed to rise to 15° C. The reaction mixture was further stirred at RT for 2 h. TLC showed completion of the reaction. Ethyl acetate (104 L) was added to the reaction mixture and layers were separated. The aqueous layer was re-extracted with ethyl acetate (2×104 L). The combined organic layers were washed with water (52 L), sodium thiosulfate (2×156 L, 10% solution), water (52 L) and brine (70 L) and dried over sodium sulfate (10.4 Kg). After filtration, the filtrate was concentrated under vacuum below 40° C. to afford crude compound 1h (4.4 kg) as dark syrup.

e. To a stirred solution of 1h (2.56 g, 4.88 mmol) in dioxane (50 mL) was added water (15 mL) and cooled to 0° C. To this cooled solution at 0° C. was added hydroxylamine-O-sulfonic acid (1.93 g, 17.10 mmol). After stirring for 1 h, a cold solution of potassium hydroxide (2.19 g, 39.0 mmol) in water and dioxane (20 mL+20 mL) was added and further stirred at 0° C. for 1 h. The reaction mixture was diluted with ethyl acetate (100 mL), the organic layer was separated and washed with water (2×50 mL) and brine (1×50 mL) and dried (MgSO$_4$). After filtration, the filtrate was concentrated to afford 2.6 g of 1i, which was used as such for the next step.

f. To a stirred solution of 1i (2.55 g, 4.88 mmol) in N,N-dimethylacetamide (70 mL) was added formamidine acetate (5.08 g, 48.88 mmol) and the reaction mixture was stirred at 140° C. for 3 h. Most of the N,N-dimethylacetamide was removed under vacuum and the residue was suspended in water (100 mL), which was extracted with ethyl acetate (2×250 mL). The combined organic extracts were washed with water (50 mL) and brine (50 mL) and dried (MgSO$_4$).

After filtration, the filtrate was concentrated and the residue was purified by flash chromatography using a mixture of ethyl acetate and methanol (9:1) in hexanes (0 to 30%) to provide impure compound (1.25 g). Further purification by chromatography on silica gel gave 0.48 g (17.8% from 1f) of 1j, 7-((2S,3S,4R,5R)-3,4-bis(benzyloxy)-5-(benzyloxymethyl)-3-methyltetrahydrofuran-2-yl)pyrrolo[1,2-f][1,2,4]triazin-4-amine, as a light brown solid. $^1$H NMR (CDCl$_3$): δ 7.87 (s, 1H), 7.43-7.21 (m, 15H), 6.88 (d, J=4.5 Hz, 1H), 6.50 (d, J=4.5 Hz, 1H), 5.87 (s, 1H), 5.36 (b, 2H, D$_2$O exchangeable), 4.83 (dd, J=31.8, 12.2 Hz, 2H), 4.68-4.52 (m, 4H), 4.40-4.35 (m, 1H), 4.04 (d, J=8.8 Hz, 1H), 3.88 (dd, J=10.9, 2.3 Hz, 1H), 3.69 (dd, J=11.1, 3.6 Hz, 1H), 1.00 (s, 3H). MS (ES$^+$): 551.40 (M+H)$^+$.

NOTE: Acetic acid and n-BuOH can also be used as solvent in place of dimethyl acetamide.

g. To a stirred solution of 1j (0.27 g, 0.484 mmol) in dichloromethane (25 mL) was added boron trichloride (4.84 mL, 4.84 mmol, 1M solution in dichloromethane) at −40° C. and the mixture was further stirred at −40° C. for 30 min and slowly brought to 0° C. in about 30 min and stirred at 0° C. for 20 min. The reaction was quenched by adding ethyl alcohol (50 mL) and concentrated under reduced pressure. Again, ethyl alcohol (50 mL) was added and concentrated. This operation was repeated 4 times. After concentration, the residue was dissolved in mixture of isopropyl alcohol and methanol (20 and 2 mL) and methanol was removed by concentration under vacuum. Solid separated out, which was collected by filtration and dried at 60° C. under vacuum to provide 39 mg (25%) of 1k, (2S,3R,4R,5R)-2-(4-aminopyrrolo[1,2-f][1,2,4]triazin-7-yl)-5-(hydroxymethyl)-3-methyltetrahydrofuran-3,4-diol, as a colorless solid. $^1$H NMR (DMSO-d$_6$): δ 9.71 (bs, 1H, D$_2$O exchangeable), 8.99 (bs, 1H, D$_2$O exchangeable), 8.16 (s, 1H), 7.41 (d, J=4.5 Hz, 1H), 6.97 (d, J=4.7 Hz, 1H), 5.34 (s, 1H), 4.8-4.0 (m, 3H, D$_2$O exchangeable), 3.81-3.56 (m, 4H), 0.79 (s, 3H). MS (ES$^+$): 281.6 (M+H)$^+$. Analysis: Calc for C$_{12}$H$_{16}$N$_4$O$_4$. HCl: C, 45.50; H, 5.40; N, 17.68; Cl, 11.19. Found: C, 45.53; H, 5.54; N, 17.93; Cl, 11.17.

Compound 1k can also be prepared as follows.

h. To a solution of compound 1j (128 g) in methanol (1.4 L), conc. HCl (130 mL) was added followed by 10% Pd/C (12 g) and the mixture was hydrogenated at 70 psi for 10 h. Since the compound precipitated out of the solution, water (500 mL) was added to the mixture and heated at 60° C. for about 1 h and filtered through a Celite pad. The Celite pad with palladium was re-suspended in a mixture of water (400 mL) and methanol (400 mL) and heated at 60° C. for about 1 h and again filtered through Celite. This operation was repeated until there was no compound left un-dissolved. The combined filtrates were concentrated under vacuum and recrystallized from water and ethanol (1:20) to afford 32.5 g of the desired product 1k as pale yellow crystals. The mother liquor was concentrated and recrystallized again to afford another crop of 5.6 g.

Example 2

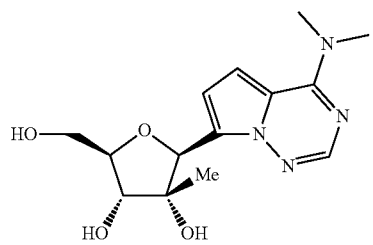 [SMILES: CN(C)c1ncnn2c([C@@H]3O[C@H](CO)[C@@H](O)[C@@]3(C)O)ccc12]

(2S,3R,4R,5R)-2-(4-(Dimethylamino)pyrrolo[1,2-f][1,2,4]triazin-7-yl)-5-(hydroxymethyl)-3-methyltetrahydrofuran-3,4-diol (2e)

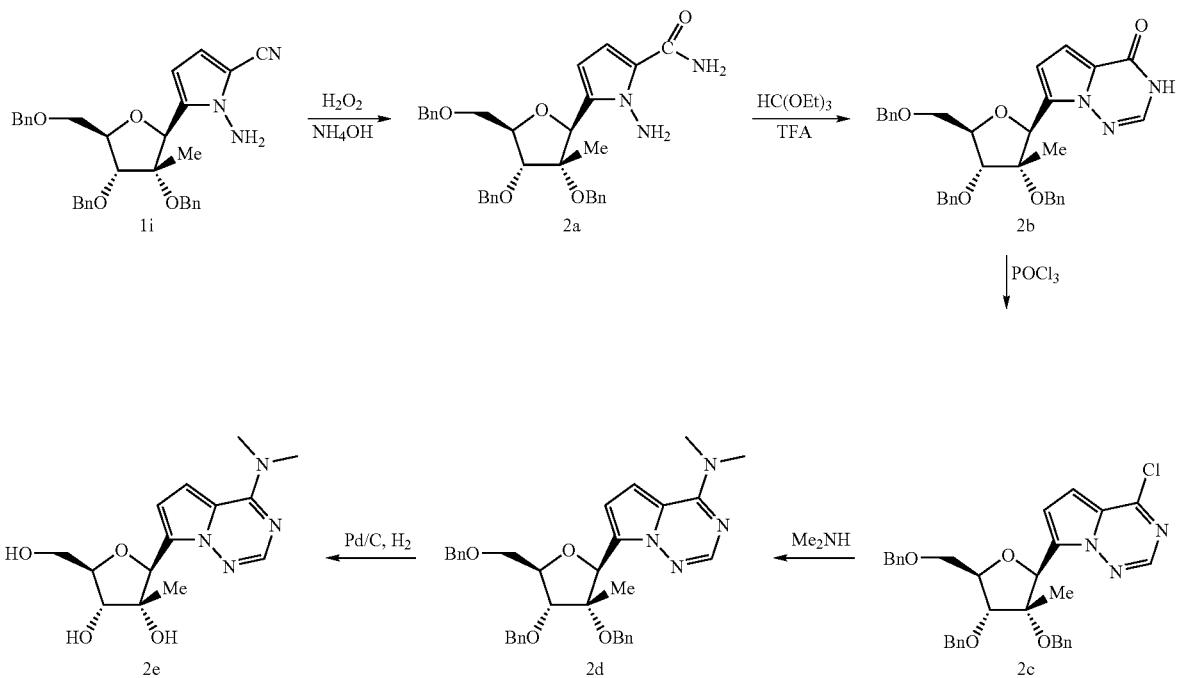

a. A solution of 1i (500 mg, 0.95 mmol, preparation given under Example 1) in EtOH (25 mL) was treated with conc. NH₄OH (28-30%, 9.5 mL) and hydrogen peroxide (30% in water, 0.3 mL) followed by stirring at RT for 20 h. Additional hydrogen peroxide (30% in water, 0.1 mL) was added and stirring was continued for 4 h. The reaction mixture was concentrated to dryness. The residue was treated with chloroform (50 mL) and washed with water (50 mL). The aqueous phase was extracted again with chloroform (50 mL). The combined extracts were washed with brine (50 mL), dried over MgSO₄, filtered, and concentrated to give yellow syrup (2a, 0.51 g). MS (ES⁻): 540.1 (M–H)⁻. The crude 2a (0.48 g) was dissolved in triethyl orthoformate (10 mL) and treated with TFA (0.07 mL, 0.91 mmol) followed by stirring at 80° C. for 45 min and concentration to dryness. The residue was purified by column chromatography on silica gel (hexanes/EtOAc, 1:0 to 1:1) to give 2b (375 mg, 76% for 2 steps, $R_f$=0.33, hexanes/EtOAc=1:0) as a light brown syrup. ¹H NMR (DMSO-d₆): δ 11.70 (bs, 1H), 7.90 (d, J=3.1 Hz, 1H), 7.43-7.20 (m, 15H), 6.84 (d, J=4.4 Hz, 1H), 6.67 (d, J=4.4 Hz, 1H), 5.56 (s, 1H), 4.77-4.53 (m, 6H), 4.22-4.15 (m, 1H), 3.99 (d, J=8.2 Hz, 1H), 3.85-3.65 (m, 2H), 1.07 (s, 3H); MS (ES⁻): 550.6 (M–H)⁻.

b. A solution of 2b (3.413 g, 6.19 mmol) in acetonitrile (80 mL) was treated with benzyltriethylammonium chloride (2.88 g, 98%, 12.39 mmol) and N,N-dimethylaniline (1.2 mL, 9.37 mmol). The mixture was heated to 80° C. and treated with phosphorous oxychloride (3.5 mL, 37.85 mol) followed by stirring at 80° C. for 45 min. Additional phosphorous oxychloride (15 mL) was added and the stirring at 80° C. was continued for 2.5 h. The third portion of phosphorous oxychloride (10 mL) was added and the stirring at 80° C. was continued for another 3 h. The reaction mixture was concentrated to dryness. The residue was dissolved in chloroform (400 mL) and washed with 1M NaHCO₃ (200 mL), water (200 mL), brine (100 mL), and dried over MgSO₄. After filtration, the filtrate was concentrated and purified by column chromatography on silica gel (hexanes/EtOAc, 1:0 to 4:1) to give 2c (2.67 g, 76%, $R_f$=0.45, hexanes/EtOAc=4:1) as a yellow oil. ¹H NMR (DMSO-d₆): δ 8.49 (s, 1H), 7.44-7.22 (m, 16H), 7.07 (d, J=4.7 Hz, 1H), 5.74 (s, 1H), 4.79-4.55 (m, 6H), 4.29-4.21 (m, 1H), 4.05 (d, J=8.0 Hz, 1H), 3.89-3.70 (m, 2H), 1.03 (s, 3H).

c. A solution of 2c (200 mg, 0.35 mmol) in EtOH (6 mL) and chloroform (1.5 mL) was treated with triethylamine (0.92 mL, 6.6 mmol) and then dimethylamine (40% in water, 0.44 mL, 3.51 mmol) followed by stirring at 50° C. for 12 h. The reaction mixture was concentrated and purified by column chromatography on silica gel (hexanes/EtOAc, 1:0 to 1:1) to give 2d (189 mg, 93%, $R_f$=0.42, hexanes/EtOAc=1:1) as a light yellow syrup. ¹H NMR (DMSO-d₆): δ 7.87 (s, 1H), 7.42-7.25 (m, 15H), 6.91 (d, J=4.6 Hz, 1H), 6.78 (d, J=4.6 Hz, 1H), 5.70 (s, 1H), 4.80-4.54 (m, 6H), 4.23-4.15 (m, 1H), 3.99 (d, J=8.5 Hz, 1H), 3.87-3.67 (m, 2H), 3.36 (s, 6H), 1.03 (s, 3H); MS (ES⁺): 579.1 (M+H)⁺.

d. A solution of 2d (109 mg, 0.19 mmol) in MeOH (15 mL) was treated with 1N HCl (aq. 0.69 mL) and Pd/C (10%, 50 mg) followed by hydrogenation (60 psi) for 20 h. The reaction mixture was filtered and concentrated. The residue was purified by column chromatography on silica gel (chloroform/CMA 80, 1:0 to 1:1) to give the desired compound, 2e (52 mg, 89%, $R_f$=0.60, chloroform/CMA 80=1:1) as a white solid. Mp: 181° C.; ¹H NMR (DMSO-d₆): δ 7.83 (s, 1H), 6.93 (d, J=4.5 Hz, 1H), 6.77 (d, J=4.5 Hz, 1H), 5.42 (s, 1H), 4.89 (d, J=7.0 Hz, 1H), 4.80 (t, J=5.4 Hz, 1H), 4.70 (s, 1H), 3.80-3.54 (m, 4H), 3.35 (s, 3H), 0.77 (s, 3H); MS (ES⁺): 309.5 (M+H)⁺; IR (KBr): 3477, 3382, 2913, 1593, 1559, 1416, 1054 cm⁻¹.

Anal. Calcd for C₁₄H₂₀N₄O₄: C, 54.53; H, 6.54; N, 18.17. Found: C, 54.45; H, 6.72; N, 17.70.

Example 3

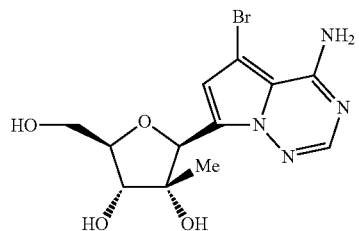 [SMILES: C[C@@]1(O)[C@H](O)[C@@H](CO)O[C@H]1c1cc(Br)c2c(N)ncnn12]

(2S,3R,4R,5R)-2-(4-Amino-5-bromopyrrolo[1,2-f][1,2,4]triazin-7-yl)-5-(hydroxymethyl)-3-methyltetrahydrofuran-3,4-diol (3b)

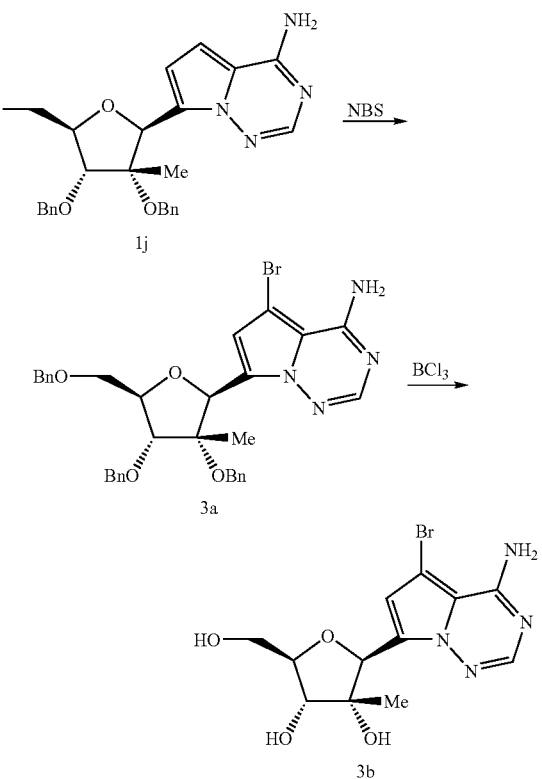

a. A solution of 1j (100 mg, 0.18 mmol, preparation given under Example 1) in CH₂Cl₂ (9 mL) was cooled with ice/water bath and treated with NBS in several portions (32 mg, 0.18 mmol) followed by stirring at RT for 1 h. The reaction mixture was concentrated and purified by column chromatography on silica gel (chloroform/methanol, 1:0 to 20:1) to give 3a (102 mg, 90%, $R_f$=0.53, chloroform/MeOH=95:5) as a yellow solid. ¹H NMR (DMSO-d₆): δ 7.89 (s, 1H), 7.42-7.25 (m, 15H), 6.91 (s, 1H), 5.64 (s, 1H), 4.74 (s, 2H), 4.66-4.52 (m, 4H), 4.22-4.16 (m, 1H), 4.03 (d, J=8.7 Hz, 1H), 3.90-3.68 (m, 2H), 1.05 (s, 3H); MS (ES⁺): 631.3 (M+H)⁺.

b. A solution of 3a (87 mg, 0.14 mmol) in dichloromethane (2.5 mL) was cooled to −78° C. and treated with BCl₃ dropwise (1M in dichloromethane, 1.4 mL) followed by stirring at −78° C. for 2 h and at −25° C. for 2.5 h. The reaction mixture was treated with CH$_2$Cl$_2$/MeOH (1:1, 1.5 ml) and stirred at −15° C. for 0.5 h. It was then neutralized with conc. NH$_4$OH at 0° C. and stirred at room temperature for 15 min followed by concentration under vacuum. The residue was treated with MeOH (25 mL) and 4M HCl in 1,4-dioxane (12.5 mL) and stirred at room temperature for 1 h followed by concentration. The residue was purified on a silica gel column using chloroform: CMA 80 (1:0 to 1:1, R$_f$=0.24, chloroform:CMA 80=1:1) as eluent. It was further purified by HPLC(CH$_3$CN/H$_2$O, 0-40 min, 0-30% CH$_3$CN, monitoring at 244 nm). Fractions containing the desired product, 3b (t$_R$=30.5 min) were concentrated to give a white solid (15.7 mg, yield: 31%, purity checked by HPLC: 98.4%). $^1$H NMR (DMSO-d$_6$, D$_2$O exchange): δ 7.85 (s, 1H), 6.94 (s, 1H), 5.36 (s, 1H), 3.78-3.50 (m, 4H), 0.79 (s, 3H); MS (ES$^-$): 357.2 (M−H)$^-$; IR (KBr): 3465, 1636, 1473, 1065 cm$^{-1}$.

Example 4

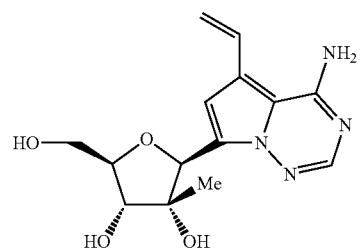 [SMILES: C=Cc1cc([C@@H]2O[C@H](CO)[C@@H](O)[C@@]2(C)O)n2ncnc(N)c12]

(2S,3R,4R,5R)-2-(4-Amino-5-vinylpyrrolo[1,2-f][1,2,4]triazin-7-yl)-5-(hydroxymethyl)-3-methyltetrahydrofuran-3,4-diol (4f)

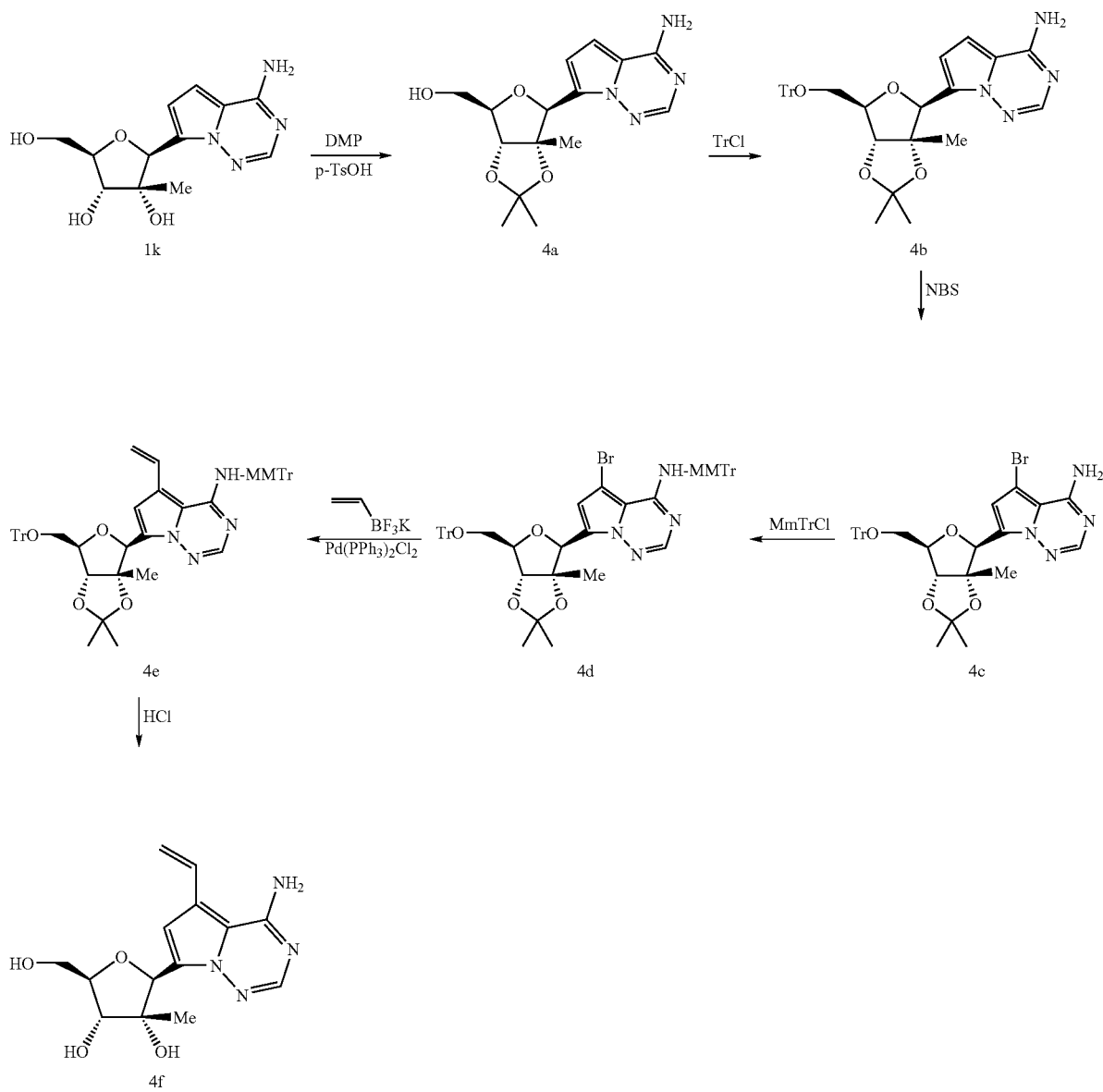

a. A suspension of 1k HCl (504 mg, 1.59 mmol) in DMF (15 mL) and acetone (15 mL) was treated with 2,2-dimethoxypropane (3.5 mL, 98%, 27.96 mmol) and p-TsOH (440 mg, 98.5%, 2.28 mmol) followed by stirring at RT for 5 h. The reaction mixture was neutralized with 2N NaOH (aq.) followed by concentration to dryness. The residue was purified by column chromatography on silica gel (chloroform/methanol, 1:0 to 95:5) to give 4a (504 mg, 99%, $R_f$=0.33, chloroform/methanol=95:5) as a yellow solid. $^1$H NMR (DMSO-$d_6$): δ 7.83 (s, 1H), 7.68 (bs, 2H), 6.87 (d, J=4.6 Hz, 1H), 6.63 (d, J=4.6 Hz, 1H), 5.54 (s, 1H), 4.97 (t, J=5.8 Hz, 1H), 4.37 (d, J=2.4 Hz, 1H), 4.03-3.96 (m, 1H), 3.65-3.50 (m, 2H), 1.55 (s, 3H), 1.33 (s, 3H), 1.15 (s, 3H); MS (ES$^+$): 321.2 (M+H)$^+$.

b. A solution of 4a (467 mg, 1.46 mmol) in pyridine (14 mL) was treated with DMAP (46 mg, 99%, 0.37 mmol) and trityl chloride (630 mg, 2.21 mmol) followed by stirring at RT for 16 h. Additional trityl chloride (900 mg, 3.16 mmol) was added and the stirring was continued at RT for 70 h. The reaction mixture was diluted with EtOAc (200 mL) and washed with water (2×100 mL) and brine (100 mL), dried over MgSO$_4$, filtered, and the filtrate was concentrated. The residue was purified by column chromatography on silica gel (hexanes/EtOAc/MeOH, 1:1:0 to 1:1:0.1) to give 4b (682 mg, 83%, $R_f$=0.48, hexanes/EtOAc/MeOH=1:1:0.1) as a yellow oil. $^1$H NMR (DMSO-$d_6$): δ 7.83 (s, 1H), 7.70 (s, 2H), 7.50-7.24 (m, 15H), 6.89 (d, J=4.3 Hz, 1H), 6.55 (d, J=4.3 Hz, 1H), 5.57 (s, 1H), 4.26 (d, J=3.0 Hz, 1H), 4.20-4.12 (m, 1H), 3.23 (d, J=5.2 Hz, 2H), 1.54 (s, 3H), 1.31 (s, 3H), 1.08 (s, 3H); MS (ES$^+$): 585.1 (M+Na)$^+$.

c. A solution of 4b (606 g, 1.08 mmol) in CH$_2$Cl$_2$ (50 mL) was cooled with ice/water and treated with NBS in several portions (627 mg, 3.49 mmol) followed by stirring at RT for 1 h. The reaction mixture was concentrated and purified by column chromatography on silica gel (hexanes/EtOAc/MeOH, 1:1:0 to 1:1:0.1) to give 4c (626 mg, 90%, $R_f$=0.62, hexanes/EtOAc/MeOH=1:1:0.1) as a white solid. $^1$H NMR (DMSO-$d_6$): δ 7.87 (s, 1H), 7.50-7.25 (m, 17H), 6.64 (s, 1H), 5.53 (s, 1H), 4.26 (d, J=3.1 Hz, 1H), 4.23-4.16 (m, 1H), 3.23 (d, J=5.5 Hz, 2H), 1.53 (s, 3H), 1.31 (s, 3H), 1.03 (s, 3H); MS (ES$^+$): 663.1 (M+Na).

d. A solution of 4c (15.45 g, 24.08 mmol) in pyridine (260 mL) was treated with 4-methoxytriphenylmethyl chloride (38 g, 97%, 119.36 mmol) followed by stirring at 70° C. for 37 h. The reaction mixture was diluted with EtOAc (800 mL) and washed with water (2×500 mL) and brine (300 mL), dried over MgSO$_4$, filtered, and concentrated. The residue was purified by column chromatography on silica gel (hexanes/EtOAc, 1:0 to 8:1) to give 4d (31 g, used as such for next step, $R_f$=0.56, hexanes/EtOAc=4:1) as a light yellow solid. $^1$H NMR (DMSO-$d_6$): δ 7.94 (s, 1H), 7.63 (s, 1H), 7.50-7.16 (m, 27H), 6.89 (d, J=9.0 Hz, 2H), 6.72 (s, 1H), 5.49 (s, 1H), 4.24 (d, J=2.8 Hz, 1H), 4.22-4.14 (m, 1H), 3.73 (s, 3H), 3.23 (d, J=5.5 Hz, 2H), 1.49 (s, 3H), 1.28 (s, 3H), 1.05 (s, 3H); MS (ES$^+$): 937.3 (M+Na)$^+$.

e. A solution of the above 4d (31 g from the previous step) in DME (500 mL) was treated with potassium vinyltrifluoroborate (7.8 g, 58.23 mmol), NaHCO$_3$ (5.9 g, 70.23 mmol), Pd(PPh$_3$)$_2$Cl$_2$ (1.2 g, 98%, 1.68 mmol), and H$_2$O (55 mL) followed by reflux for 6 h. The reaction mixture was treated with water (500 mL) and extracted with EtOAc (1.0 L and 0.5 L). The combined extracts were washed with brine (500 mL) and dried over MgSO$_4$, filtered, and concentrated. The residue was purified by column chromatography on silica gel (hexanes/EtOAc, 1:0 to 8:1) to give 4e (11.32 g, 55% for two steps, $R_f$=0.22, hexanes/EtOAc=8:1) as a yellow solid. $^1$H NMR (DMSO-$d_6$): δ 7.54 (s, 1H), 7.48-7.20 (m, 28H), 7.13 (dd, J=17.4, 11.0 Hz, 1H), 6.85 (d, J=8.8 Hz, 2H), 6.76 (s, 1H), 5.55 (dd, J=17.4, 1.4 Hz, 1H), 5.50 (s, 1H), 5.29 (dd, J=11.0, 1.4 Hz, 1H), 4.24 (d, J=3.0 Hz, 1H), 4.18-4.12 (m, 1H), 3.71 (s, 3H), 3.22 (d, J=5.3 Hz, 2H), 1.48 (s, 3H), 1.27 (s, 3H), 1.07 (s, 3H).

f. A solution of 4e (205 mg, 0.23 mmol) in acetonitrile (25 mL) was treated with 1N HCl (aq. 2.5 mL) followed by stirring at RT for 23 h. The reaction mixture was concentrated to dryness and purified by column chromatography on silica gel (chloroform/CMA 80, 1:0 to 1:1) to give 4f (36 mg, 51%, $R_f$=0.12, chloroform/CMA 80=1:1) as a yellow solid. mp: 128-131° C.; $^1$H NMR (DMSO-$d_6$): δ 7.78 (s, 1H), 7.32 (s, 2H), 7.23 (dd, J=16.9, 10.8 Hz, 1H), 7.03 (s, 1H), 5.58 dd, J=16.9, 1.5 Hz, 1H), 5.35 (s, 1H), 5.12 (dd, J=10.8, 1.5 Hz, 1H), 4.90 (d, J=6.4 Hz, 1H), 4.83 (t, J=5.5 Hz, 1H), 4.69 (s, 1H), 3.80-3.52 (m, 4H), 0.79 (s, 3H); MS (ES$^+$): 307.1 (M+H)$^+$; HPLC purity: 98.9% (270 nm, $t_R$=10.6 min; solvent A: 0.1M ammonium acetate, solvent B: acetonitrile; 0-5 min, 0% B; 5-15 min, 0-45% B; 15-20 min, 45-90% B; 20-25 min, 90-0% B.); IR (neat): 3323, 1621, 1592, 1377 cm$^{-1}$. Anal. Calcd for $C_{14}H_{18}N_4O_8 \cdot 0.5H_2O \cdot 0.5$ MeOH: C, 52.56; H, 6.39; N, 16.91. Found: C, 52.51; H, 6.00; N, 16.61.

Example 5

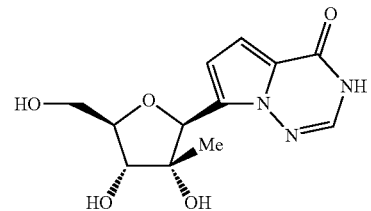 [SMILES: C[C@@]1(O)[C@H](O)[C@@H](CO)O[C@H]1c1ccc2c(=O)[nH]cnn12]

7-((2S,3R,4R,5R)-3,4-Dihydroxy-5-(hydroxymethyl)-3-methyltetrahydrofuran-2-yl)pyrrolo[1,2-f][1,2,4]triazin-4(3H)-one (5)

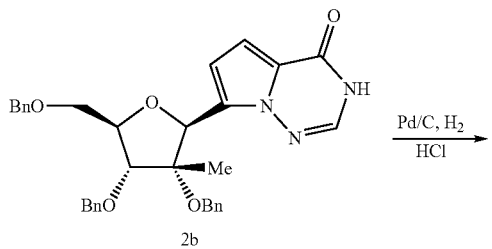

2b

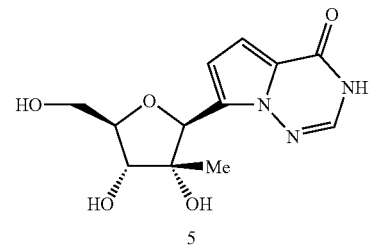

5

A solution of 2b (300 mg, 0.54 mmol, its preparation is described under Example 2) in MeOH (40 mL) was treated with 1N HCl (aq. 1.85 mL) and Pd/C (10%, 150 mg) followed by hydrogenation (60 psi) for 18 h. The reaction mixture was filtered and concentrated. The residue was purified by column chromatography on silica gel (chloroform/CMA 80, 1:0 to 1:1) to give 5 (48 mg, 32%, $R_f$=0.66, chloroform/CMA 80=1:1) as a yellow solid (a mixture of two diastereoisomers, ratio=2:1). $^1$H NMR (DMSO-$d_6$): δ 11.61 (bs, 1H), 7.84 (s) & 7.81 (s) (1H), 6.852 (d, J=4.3 Hz) & 6.846 (d, J=4.3 Hz) (1H), 6.65 (d, J=4.3 Hz) & 6.63 (d, J=4.3 Hz) (1H), 5.28 (s) & 5.23 (s) (1H), 4.96 (d, J=6.6 Hz) & 4.93 (d, J=6.6 Hz) (1H), 4.83-4.62 (m, 2H), 3.86-3.50 (m, 4H), 1.09 (s) & 0.79 (s) (3H); MS (ES$^-$): 280.4 (M−H)$^-$. Anal. Calcd for $C_{12}H_{15}N_3O_5 \cdot 1.75H_2O$: C, 46.08; H, 5.96; N, 13.43. Found: C, 45.91; H, 5.54; N, 13.21.

Example 6

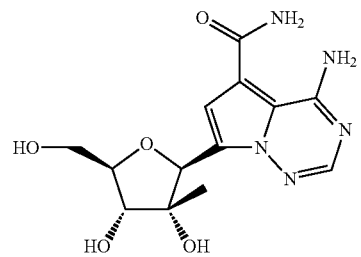 [SMILES: C[C@@]1(O)[C@H](O)[C@@H](CO)O[C@H]1c1cc(C(N)=O)c2c(N)ncnn12]

4-Amino-7-((2S,3R,4R,5R)-3,4-dihydroxy-5-(hydroxymethyl)-3-methyltetrahydrofuran-2-yl)pyrrolo[1,2-f][1,2,4]triazine-5-carboxamide (6g)

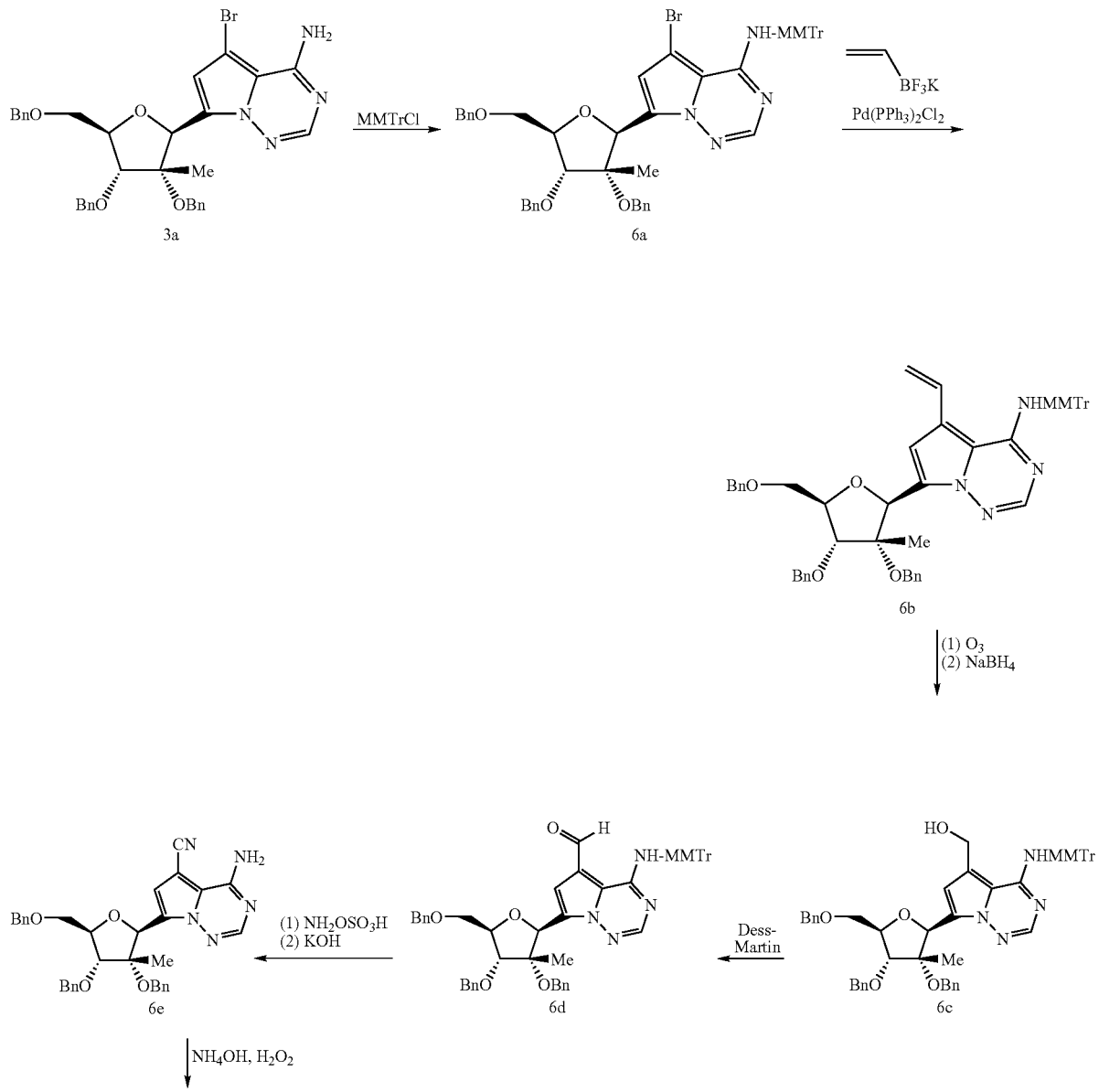

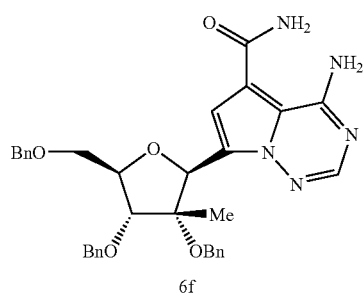

6f

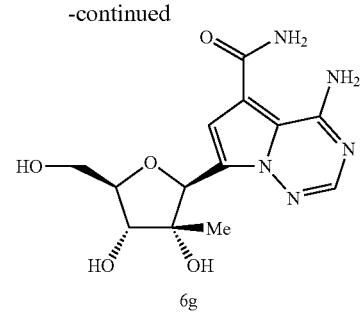

-continued

6g a. A solution of 3a (27.85 g, 44.23 mmol, preparation given under Example 3) in pyridine (400 mL) was treated with 4-methoxytriphenylmethyl chloride (56.74 g, 178.24 mmol) followed by stirring at 70° C. for 16 h. The reaction mixture was diluted with EtOAc (1.5 L) and washed with water (2×700 mL) and brine (500 mL), dried over MgSO$_4$, filtered, and the filtrate was concentrated. The residue was purified by column chromatography on silica gel (hexanes/EtOAc, 1:0 to 4:1) to give 6a (28.38 g, 71%, R$_f$=0.49, hexanes/EtOAc=4:1) as a light yellow solid. $^1$H NMR (DMSO-d$_6$): δ 7.91 (s, 1H), 7.63 (s, 1H), 7.45-7.12 (m, 27H), 6.96 (s, 1H), 6.87 (d, J=8.9 Hz, 2H), 5.56 (s, 1H), 4.74-4.50 (m, 6H), 4.20-4.12 (m, 1H), 4.02 (d, J=8.5 Hz, 1H), 3.87-3.64 (m, 2H), 3.71 (s, 3H), 1.05 (s, 3H).

b. A solution of 6a (26.1 g, 28.94 mmol) in DME (500 mL) was treated with potassium vinyltrifluoroborate (7.2 g, 53.75 mmol), NaHCO$_3$ (7.2 g, 85.70 mmol), Pd(PPh$_3$)$_2$Cl$_2$ (1.4 g, 98%, 1.99 mmol), and H$_2$O (65 mL) followed by reflux for 6 h. The reaction mixture was treated with water (500 mL) and extracted with EtOAc (1.8 L and 0.5 L). The combined extracts were washed with brine (500 mL) and dried over MgSO$_4$, filtered, and the filtrate was concentrated. The residue was purified by column chromatography on silica gel (hexanes/EtOAc, 1:0 to 6:1) to give 6b (18.3 g, 74%, R$_f$=0.39) as a light yellow solid. $^1$H NMR (DMSO-d$_6$): δ 7.56 (s, 1H), 7.44-7.12 (m, 28H), 7.01 (dd, J=17.2, 11.0 Hz, 1H), 6.93 (s, 1H), 6.84 (d, J=8.8 Hz, 2H), 5.57 (s, 1H), 5.31 (d, J=17.2 Hz, 1H), 5.16 (d, J=11.0 Hz, 1H), 4.76-4.52 (m, 6H), 4.22-4.13 (m, 1H), 4.04 (d, J=8.4 Hz, 1H), 3.88-3.70 (m, 2H), 3.71 (s, 3H), 1.05 (s, 3H); MS (ES$^+$): 849.5 (M+H)$^+$ c. A solution of 6b (8 g, 9.42 mmol) in dichloromethane (250 mL) and MeOH (40 mL) was cooled to −78° C. and bubbled with O$_3$ until a blue color appeared. The reaction mixture was treated with NaBH$_4$ (1.8 g, 46.63 mmol) at −78° C., warmed up, and stirred at RT for 19 h. It was then neutralized with HOAc followed by concentration to remove most of solvent. The residue was treated with EtOAc (500 mL) and washed with water (2×400 mL). The aqueous layer was extracted again with EtOAc (300 mL). The combined organic extracts were washed with brine (500 mL), dried over MgSO$_4$, filtered, and concentrated. The residue was purified by column chromatography on silica gel (hexanes/EtOAc, 1:0 to 3:1) to give 6c (3.987 g, 50%, R$_f$=0.46) as a white solid. $^1$H NMR (DMSO-d$_6$): δ 9.77 (s, 1H), 7.49 (s, 1H), 7.40-7.12 (m, 27H), 6.81 (d, J=9.0 Hz, 2H), 6.66 (s, 1H), 6.27 (t, J=5.0 Hz, 1H), 5.57 (s, 1H), 4.74-4.50 (m, 8H), 4.20-4.12 (m, 1H), 4.01 (d, J=8.4 Hz, 1H), 3.86-3.66 (m, 2H), 3.70 (s, 3H), 1.06 (s, 3H); MS (ES$^+$): 853.2 (M+H)$^+$ d. A solution of 6c (717 mg, 0.84 mmol) in dichloromethane (40 mL) was treated with Dess-Martin reagent (15%, w/w, 2.8 mL, 1.33 mmol) followed by stirring at RT for 4 h. The reaction mixture was diluted with EtOAc (20 mL), treated with a little MgSO$_4$, concentrated, and purified by column chromatography on silica gel (hexanes/EtOAc, 1:0 to 3:1) to give 6d (621 mg, 87%, R$_f$=0.48) as a white solid. $^1$H NMR (DMSO-d$_6$): δ 10.89 (s, 1H), 9.28 (s, 1H), 7.84 (s, 1H), 7.47 (s, 1H), 7.44-7.10 (m, 27H), 6.84 (d, J=8.9 Hz, 2H), 5.56 (s, 1H), 4.76-4.50 (m, 6H), 4.24-4.14 (m, 1H), 4.06 (d, J=8.3 Hz, 1H), 3.90-3.70 (m, 2H), 3.71 (s, 3H), 1.09 (s, 3H).

e. A solution of 6d (220 mg, 0.26 mmol) in 1,4-dioxane (3.4 mL) was treated with water (1.0 mL) and then hydroxylamine-O-sulfonic acid (106 mg, 97%, 0.91 mmol) followed by stirring at RT for 45 min. Additional hydroxylamine-O-sulfonic acid (318 mg, 97%, 2.73 mmol) was added and stirring was continued for 2 h. The reaction mixture was cooled with ice/water and reacted with a cold suspension of KOH (7.09 mmol) in water (2 mL) and 1,4-dioxane (2 mL) followed by stirring at RT for 2 h. It was diluted with EtOAc (100 mL) and washed with water (60 mL). The aqueous layer was extracted again with EtOAc (80 mL). The combined extracts were washed with water (60 mL) and brine (500 mL), dried over MgSO$_4$, filtered, and concentrated. The residue was purified by column chromatography on silica gel (hexanes/EtOAc, 1:0 to 2:1) to give 6e (86 mg, 57%, R$_f$=0.25, hexanes/EtOAc=2:1) as a light brown gel. $^1$H NMR (DMSO-d$_6$): δ 8.13 (s, 1H), 7.45-7.25 (m, 16H), 5.63 (s, 1H), 4.74 (s, 2H), 4.68-4.53 (m, 4H), 4.25-4.17 (m, 1H), 4.04 (d, J=8.5 Hz, 1H), 3.91-3.70 (m, 2H), 1.06 (s, 3H); MS (ES$^+$): 598.1 (M+Na)$^+$ f. A solution of 6e (20 mg, 0.035 mmol) in EtOH (6 mL) was treated with conc. NH$_4$OH (28-30%, 1.8 mL) and then H$_2$O$_2$ dropwise (30% in H$_2$O, 0.011 mL was taken and added into 0.2 mL of EtOH) followed by stirring at RT for 18 h. the reaction mixture was concentrated and purified by column chromatography on silica gel (hexanes/EtOAc, 1:0 to 1:1, then hexanes/EtOAc/MeOH 1:1:0.1) to give 6f (12 mg, 58%, R$_f$=0.36, hexanes/EtOAc/MeOH=1:1:0.1) as a white solid. $^1$H NMR (MeOH-d$_4$): δ 7.87 (s, 1H), 7.40-7.00 (m, 16H), 5.70 (s, 1H), 4.75-4.42 (m, 6H), 4.26-4.18 (m, 1H), 3.90 (d, J=8.0 Hz, 1H), 3.82-3.64 (m, 2H), 1.04 (s, 3H); MS (ES$^+$): 594.1 (M+H)$^+$.

g. A solution of 6f (10 mg, 0.017 mmol) in MeOH (15 mL) was treated with 1N HCl (aq., 0.69 mL) and Pd/C (10%, 50 mg) followed by hydrogenation (60 psi) for 15 h. The reaction mixture was filtered and concentrated. The residue was purified by column chromatography on silica gel (chloroform/CMA 80, 1:0 to 0:1, then CMA80/CMA 50 1:1, R$_f$=0.55, CMA 80/CMA 50=1:1) followed by HPLC purification (CH$_3$CN/H$_2$O, 0-40 min, 0-35% CH$_3$CN, monitoring at 244 nm) and column purification again on silica gel (CMA80/CMA 50, 1:0 to 1:1) to give 6g (3.3 mg, colorless film, 60%). $^1$H NMR (MeOH-d$_4$): δ 8.06 (s, 2H), 7.89 (s, 1H), 7.30 (s, 1H), 5.57 (s, 1H), 4.02-3.80 (m, 4H), 0.99 (s, 3H); MS (ES⁺): 324.2 (M+H)⁺; IR (neat): 3550, 3020, 2917, 1674, 1334 cm⁻¹.

Example 7

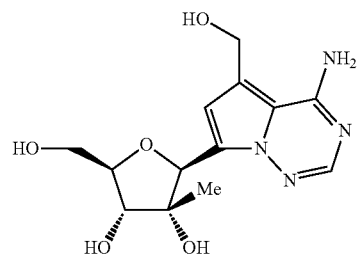 [SMILES: C[C@@]1(O)[C@H](O)[C@@H](CO)O[C@H]1c1cc(CO)c2c(N)ncnn12]

(2S,3R,4R,5R)-2-(4-Amino-5-(hydroxymethyl)pyrrolo[1,2-f][1,2,4]triazin-7-yl)-5-(hydroxymethyl)-3-methyltetrahydrofuran-3,4-diol (7)

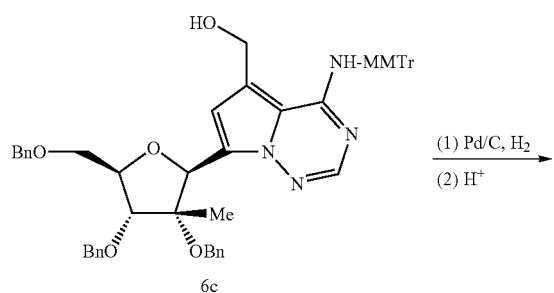

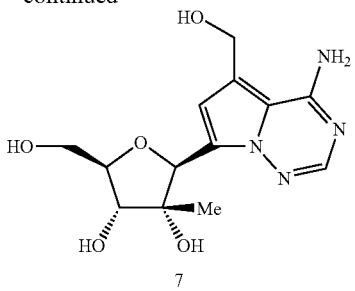

A solution of 6c (120 mg, 0.14 mmol, preparation given under Example 6) in MeOH (15 mL) was treated with 1N HCl (aq. 0.69 mL) and Pd/C (10%, 50 mg) followed by hydrogenation (60 psi) for 24 h. The reaction mixture was filtered and concentrated. The residue was treated with acetonitrile (15 mL) and 1N HCl (aq. 1.5 mL) followed by stirring at RT for 16 h. It was then concentrated to dryness and purified by column chromatography on silica gel (chloroform/CMA 80, 1:0 to 0:1) to give 7 (17 mg, 39%, R$_f$=0.33, CMA 80) as a yellow oil. ¹H NMR (DMSO-d₆, D₂O exchange): δ 7.80 (s, 1H), 6.63 (s, 1H), 5.37 (s, 1H), 4.69 (s, 2H), 3.84-3.40 (m, 4H), 0.81 (s, 3H); MS (ES⁺): 311.1 (M+H)⁺.

Example 8

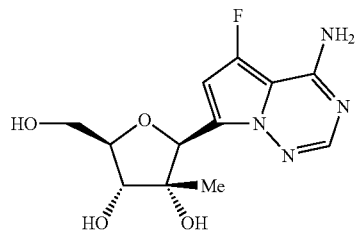 [SMILES: C[C@@]1(O)[C@H](O)[C@@H](CO)O[C@H]1c1cc(F)c2c(N)ncnn12]

(2S,3R,4R,5R)-2-(4-Amino-5-fluoropyrrolo[1,2-f][1,2,4]triazin-7-yl)-5-(hydroxymethyl)-3-methyltetrahydrofuran-3,4-diol (8f)

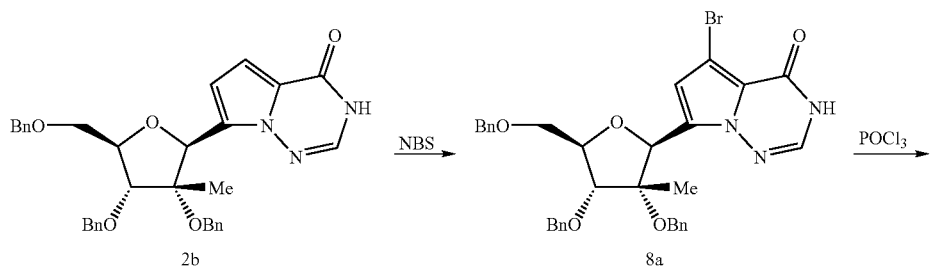

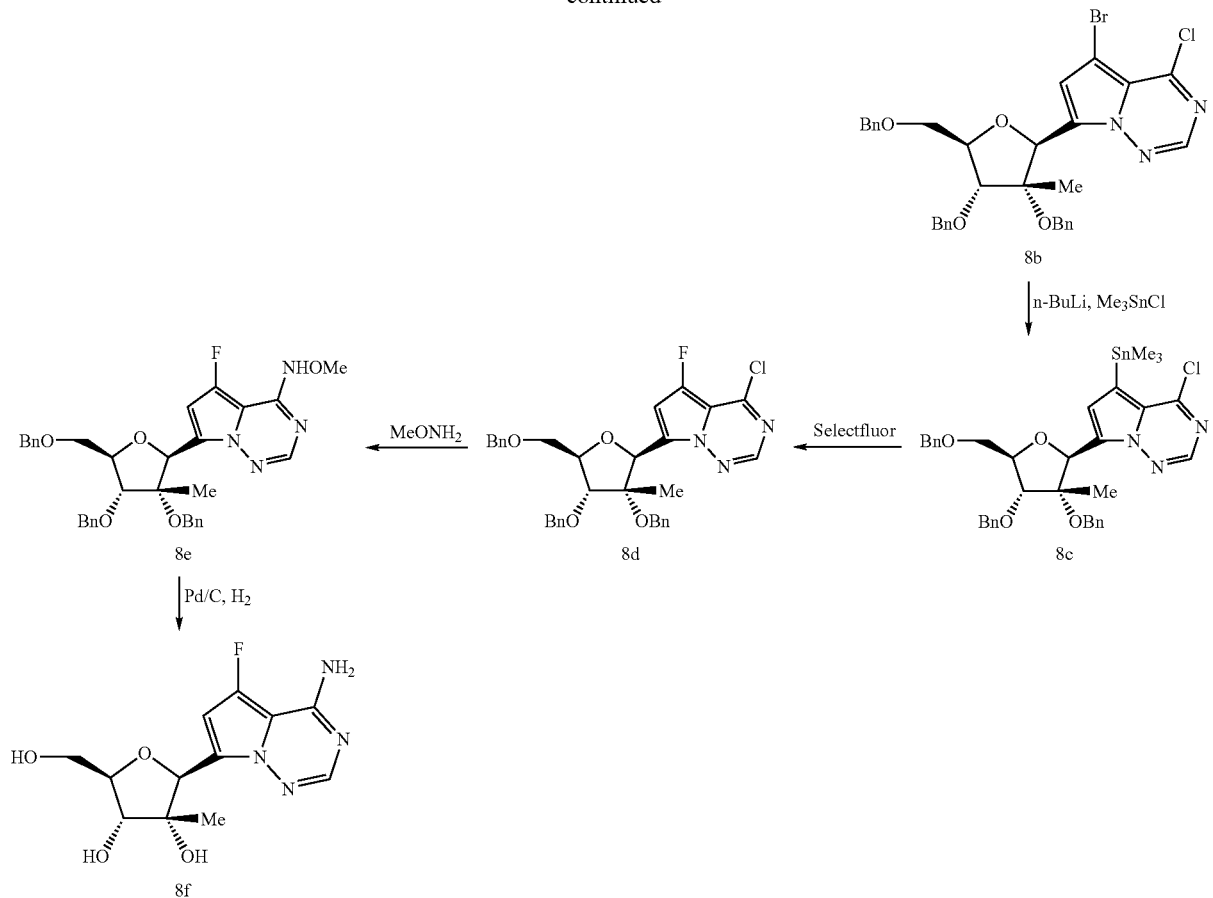

a. A solution of 2b (200 mg, 0.36 mmol, preparation given under Example 2) in dichloromethane (16 mL) was cooled with ice/water and treated with NBS (65 mg, 0.36 mmol) in several portions followed by stirring at RT for 22 h. The reaction mixture was concentrated and purified by column chromatography on silica gel (hexanes/EtOAc, 1:0 to 1:1, $R_f$=0.58, hexanes/EtOAc=1:1) to give 8a (155 mg, colorless, oil, 68%). $^1$H NMR (DMSO-$d_6$): δ 11.79 (s, 1H), 7.92 (s, 1H), 7.44-7.20 (m, 15H), 6.79 (s, 1H), 5.53 (s, 1H), 4.77-4.50 (m, 6H), 4.22-4.14 (m, 1H), 4.01 (d, J=8.9 Hz, 1H), 3.90-3.66 (m, 2H), 1.08 (s, 3H); MS (ES$^-$): 628.5 (M−H)$^-$.

b. A solution of 8a (2.42 g, 3.84 mmol) in POCl$_3$ (40 mL) was stirred at 80° C. for 4 h and concentrated to dryness. The residue was treated with chloroform (300 mL) and washed with 1M NaHCO$_3$ (150 mL), water (150 mL), brine (100 mL), and dried over MgSO$_4$. After filtration and concentration, the residue was purified by column chromatography on silica gel (hexanes/EtOAc, 1:0 to 8:1, $R_f$=0.53, hexanes/EtOAc=6:1) to give 8b (1.68 g, 68%) as a yellow syrup. MS (ES$^+$): 670.2 (M+Na)$^+$.

c. A solution of 8b (2.2 g, 3.39 mmol) in THF (24 mL) was cooled to −78° C. and treated with n-BuLi dropwise (2.5 M in hexane, 2.95 mL, 7.38 mmol). The reaction mixture was stirred at −78° C. for 0.5 h and treated with trimethyltin chloride dropwise (1M in THF, 3.4 mL, 3.4 mmol) at −78° C. followed by warming up to RT and stirring at RT for 19 h. It was then treated with sat. NH$_4$Cl (aq. 200 mL) and extracted with EtOAc (2×200 mL). The combined extracts were washed with brine (150 mL), dried over MgSO$_4$, filtered and the filtrate was concentrated. The residue was purified by column chromatography on silica gel (hexanes/EtOAc, 1:0 to 6:1, $R_f$=0.59, hexanes/EtOAc=6:1) to give 8c (386 mg, still not pure, used as such for next step) as a yellow oil. MS (ES$^+$): 733.4 (M+H)$^+$.

d. A solution of the above product 8c (351 mg) in acetonitrile (7 mL) was treated with Selectfluor™ (180 mg, 95%, 0.48 mmol) followed by stirring at RT for 17 h. The reaction mixture was filtered, the filtrate was concentrated, and the residue was purified by column chromatography on silica gel (hexanes/EtOAc, 1:0 to 6:1, $R_f$=0.25, hexanes/EtOAc=6:1) to give 8d (120 mg, used as such for next step) as a yellow oil. MS (ES$^+$): 610.0 (M+Na)$^+$.

e. A solution of the above product 8d (114 mg) in EtOH (3 mL) and chloroform (0.75 mL) was treated with triethylamine (0.57 mL, 4.09 mmol) and then methoxylamine hydrochloride (172 mg, 98%, 2.20 mmol) followed by stirring at 50° C. for 14 h. The reaction mixture was concentrated and purified by column chromatography on silica gel (hexanes/EtOAc, 1:0 to 2:1, $R_f$=0.42, hexanes/EtOAc=2:1) to give 8e (13.5 mg, used as such for next step) as a colorless film. MS (ES$^+$): 599.1 (M+H)$^+$.

f. A solution of the above product 8e (6.5 mg) in MeOH (10 mL) was treated with 1N HCl (aq. 0.46 mL) and Pd/C (10%, 35 mg) followed by hydrogenation (60 psi) for 22 h. The reaction mixture was filtered, concentrated, and purified by column chromatography on silica gel (chloroform/CMA 80, 1:0 to 0:1, $R_f$=0.39, CMA 80) followed by HPLC purification (CH$_3$CN/H$_2$O, 0-40 min, 0-35% CH$_3$CN, monitoring at 244 nm) and column purification again (chloroform/CMA 80, 1:0 to 0:1) to give 8f (2.0 mg, 0.5% for 4 steps) as a white solid. $^1$H NMR (MeOH-$d_4$): δ 7.70 (s, 1H), 6.62 (s, 1H), 5.55 (s, 1H), 4.00-3.60 (m, 4H), 0.97 (s, 3H); $^{19}$F NMR (MeOH-d$_4$): 6-160.93 (s, 1F); MS (ES$^+$): 299.1 (M+H)$^+$; IR (neat): 3296, 2919, 1620, 1530 cm$^{-1}$.
Example 9
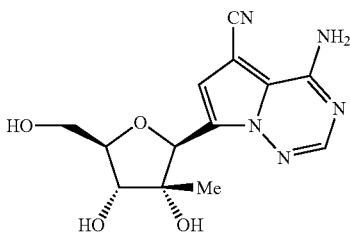 [SMILES: C[C@@]1(O)[C@H](O)[C@@H](CO)O[C@H]1c1cc(C#N)c2c(N)ncnn12]
4-Amino-7-((2S,3R,4R,5R)-3,4-dihydroxy-5-(hydroxymethyl)-3-methyltetrahydrofuran-2-yl)pyrrolo[1,2-f][1,2,4]triazine-5-carbonitrile (9d)
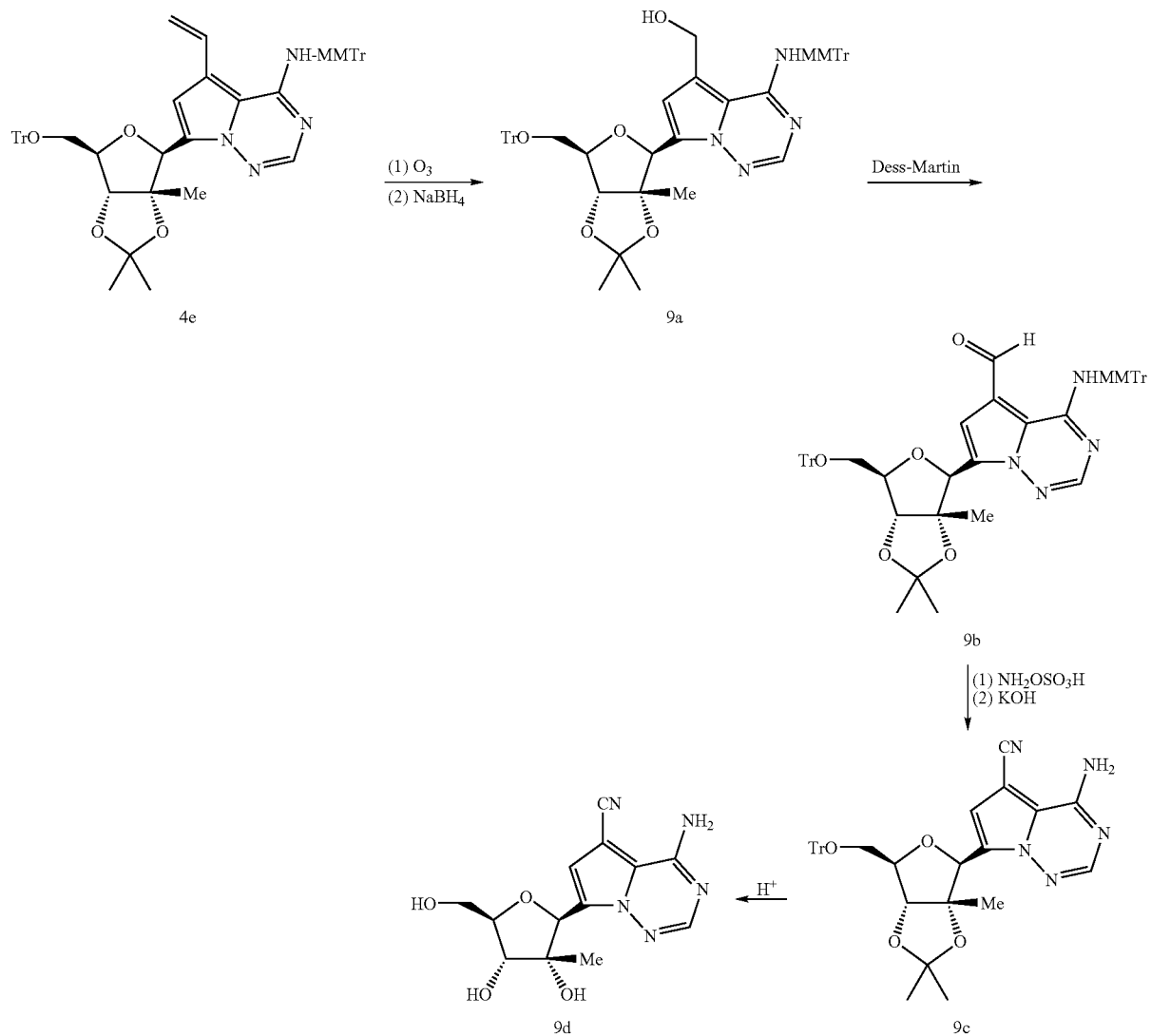

a. A solution of 4e (2 g, 2.32 mmol, preparation given under Example 4) in dichloromethane (60 mL) and MeOH (9.6 mL) was cooled to −78° C. and bubbled with O₃ until a blue color appeared. The reaction mixture was treated with NaBH₄ (440 mg, 11.40 mmol) at −78° C., warmed up, and stirred at RT for 20 h. Additional NaBH₄ (500 mg, 12.95 mmol) was added and stirring was continued at RT for 1 h. The reaction mixture was neutralized with HOAc followed by concentration to remove most of solvent. The residue was treated with EtOAc (300 mL) and washed with water (2×150 mL) and brine (100 mL), dried over MgSO₄, filtered, and concentrated. The residue was purified by column chromatography on silica gel (hexanes/EtOAc, 1:0 to 3:1) to give 9a (529 mg, 26%, $R_f$=0.49, hexanes/EtOAc=1:0) as a white solid. ¹H NMR (DMSO-d₆): δ 9.80 (s, 1H), 7.50-7.12 (m, 28H), 6.82 (d, J=8.9 Hz, 2H), 6.49 (s, 1H), 6.31 (t, J=5.1 Hz, 1H), 5.50 (s, 1H), 4.81 (d, J=5.1 Hz, 2H), 4.22 (d, J=3.0 Hz, 1H), 4.16-4.08 (m, 1H), 3.70 (s, 3H), 3.32-3.12 (m, 2H), 1.47 (s, 3H), 1.26 (s, 3H), 1.09 9s, 3H); MS (ES⁻): 863.2 (M−H)⁻.

b. A solution of 9a (487 mg, 0.56 mmol) in dichloromethane (25 mL) was treated with Dess-Martin reagent (15%, w/w, 1.9 mL, 0.9 mmol) followed by stirring at RT for 3 h. The reaction mixture was diluted with EtOAc (10 mL), treated with a little of MgSO₄, and silica gel followed by concentration and column purification (hexanes/EtOAc, 1:0 to 3:1) to give 9b (448 mg, 93%, $R_f$=0.64) as a white solid. ¹H NMR (DMSO-d₆): δ 10.96 (s, 1H), 9.73 (s, 1H), 7.82 (s, 1H), 7.50-7.16 (m, 28H), 6.85 (d, J=8.9 Hz, 2H), 5.48 (s, 1H), 4.26 (d, J=2.8 Hz, 1H), 4.22-4.14 (m, 1H), 3.71 (s, 3H), 3.34-3.16 (m, 2H), 1.49 (s, 3H), 1.28 (s, 3H), 1.08 (s, 3H).

c. A solution of 9b (244 mg, 0.28 mmol) in 1,4-dioxane (4.4 mL) was treated with water (1.1 mL) and then hydroxylamine-O-sulfonic acid (460 mg, 97%, 3.95 mmol) followed by stirring at RT for 1.5 h. Additional hydroxylamine-O-sulfonic acid (230 mg, 97%, 1.97 mmol) was added and stirring was continued for 2 h. The reaction mixture was cooled with ice/water and treated slowly with a cold suspension of KOH (11.51 mmol) in water (3 mL) and 1,4-dioxane (3 mL) followed by stirring at RT for 2 h. It was diluted with EtOAc (100 mL), washed with water (60 mL). The aqueous layer was extracted again with EtOAc (80 mL). The combined extracts were washed with water (60 mL) and brine (60 mL), dried over MgSO₄, filtered, and concentrated. The residue was purified by column chromatography on silica gel (hexanes/EtOAc, 1:0 to 2:1) to give 9c (76 mg, 46%, $R_f$=0.29, hexanes/EtOAc=2:1) as a clear oil. ¹H NMR (DMSO-d₆): δ 8.10 (s, 1H), 7.50-7.74 (m, 15H), 7.00 (s, 1H), 5.51 (s, 1H), 4.28-4.12 (m, 2H), 3.34-3.12 (m, 2H), 1.53 (s, 3H), 1.30 (s, 3H), 1.00 (s, 3H); MS (ES⁻): 586.1 (M−H)⁻.

d. A solution of 9c (63 mg, 0.11 mmol) in acetonitrile (12 mL) was treated with 1N HCl (aq., 1.2 mL) followed by stirring at RT for 19 h. The reaction mixture was concentrated and purified by column chromatography on silica gel (chloroform/CMA 80, 1:0 to 0:1, $R_f$=0.50, CMA 80) to give 9d (26 mg, 77%) as a white solid. ¹H NMR (DMSO-d₆): δ 8.12 (s, 1H), 7.36 (s, 1H), 5.36 (s, 1H), 4.97 (d, J=6.7 Hz, 1H), 4.89 (t, J=5.2 Hz, 1H), 4.83 (s, 1H), 3.82-3.56 (m, 4H), 0.81 (s, 3H); MS (ES⁺): 328.1 (M+Na)⁺; HPLC purity: 99.5% (270 nm, $t_R$=9.7 min; solvent A: 0.1 M ammonium acetate, solvent B: acetonitrile; 0-5 min, 0% B; 5-15 min, 0-45% B; 15-20 min, 45-90% B; 20-25 min, 90-0% B.); IR (neat): 3374, 3257, 2215, 1657, 1517, 1034 cm⁻¹.

Example 10

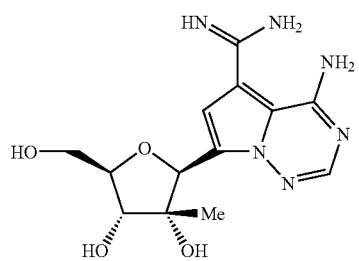 [SMILES: C[C@@]1(O)[C@H](O)[C@@H](CO)O[C@H]1c1cc(C(=N)N)c2c(N)ncnn12]

4-Amino-7-((2S,3R,4R,5R)-3,4-dihydroxy-5-(hydroxymethyl)-3-methyltetrahydrofuran-2-yl)pyrrolo[1,2-f][1,2,4]triazine-5-carboximidamide (10b)

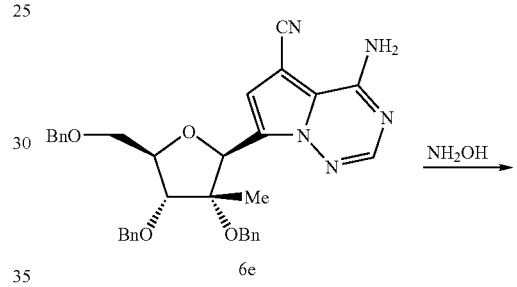

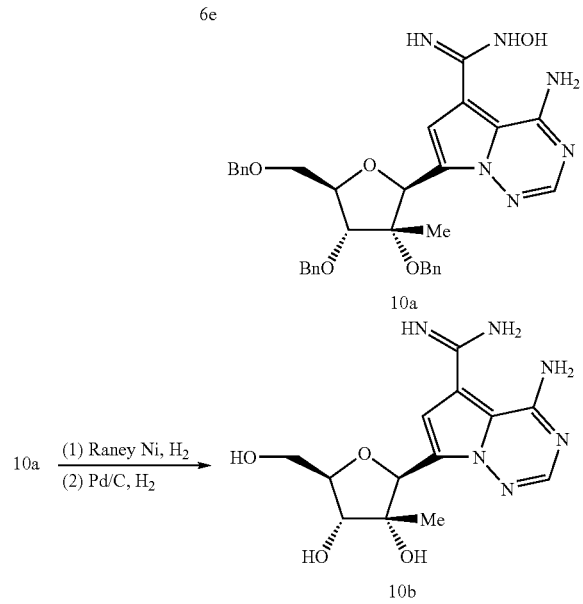

A solution of 6e (31 mg, 0.054 mmol, preparation given under Example 6) in EtOH (5 mL) was treated with NH₂OH (50% in H₂O, 0.5 mL, 8.16 mmol) followed by reflux for 1 h and concentration to give 10a, MS (ES⁻): 607.6 (M−H)⁻. The residue was dissolved in EtOH (15 mL), treated with HOAc (1.5 mL) and small amount of Raney nickel followed by hydrogenation (60 psi) for 21 h. The reaction mixture was filtered and concentrated. The residue was dissolved in MeOH (15 mL) and treated with 1N HCl (aq., 0.92 mL) and Pd/C (10%, 60 mg) followed by hydrogenation (60 psi) for 22 h. The reaction mixture was filtered and concentrated. The residue was purified twice by column chromatography on silica gel (CMA 80/CMA 50, 1:0 to 1:1, $R_f$=0.28, CMA 80/CMA 50=1:1) to give 10b (5.7 mg, 33%) as a light brown film. $^1$H NMR (MeOH-$d_4$): δ 7.96 (s, 1H), 7.20 (s, 1H), 5.50 (s, 1H), 3.92-3.66 (m, 4H), 0.88 (s, 3H). MS (ES$^+$): 323.1 (M+H)$^+$.

Example 11

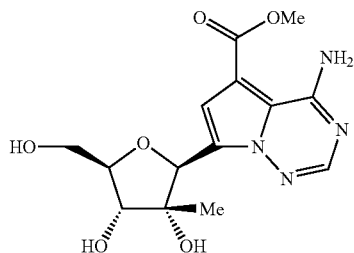 [SMILES: COC(=O)c1cc([C@@H]2O[C@H](CO)[C@@H](O)[C@@]2(C)O)n2ncnc(N)c12]

Methyl 4-amino-7-((2S,3R,4R,5R)-3,4-dihydroxy-5-(hydroxymethyl)-3-methyltetrahydrofuran-2-yl)pyrrolo[1,2-f][1,2,4]triazine-5-carboxylate (11c)

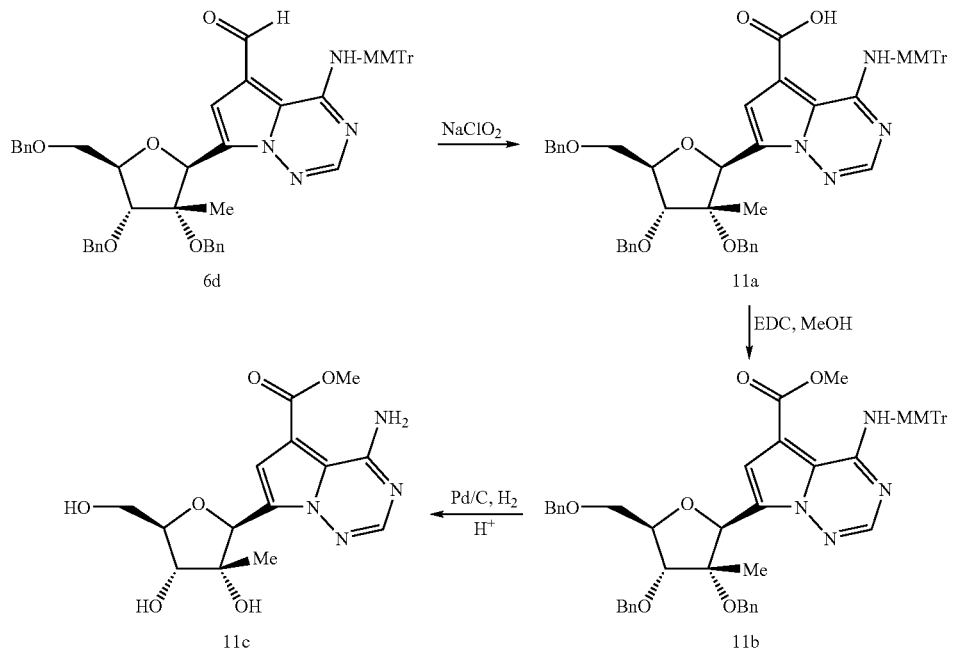

ether (100 mL) again. The combined extracts were washed with brine (50 mL), dried over MgSO$_4$, filtered, and concentrated. The residue was purified by column chromatography on silica gel (hexanes/EtOAc/MeOH, 3:1:0 to 3:1:0.08) to give 11a (60 mg, 29%, $R_f$=0.43, hexanes/EtOAc/MeOH=3:1:0.08) as a clear oil. $^1$H NMR (DMSO-$d_6$): δ 7.70 (s, 1H), 7.62 (s, 1H), 7.44-7.14 (m, 28H), 6.83 (d, J=9.0 Hz, 2H), 5.58 (s, 1H), 4.74-4.52 (m, 6H), 4.20-4.10 (m, 1H), 3.99 (1H), 3.84-3.64 (m, 2H), 3.70 (s, 3H), 1.06 (s, 3H).

b. A solution of 11a (50 mg, 0.058 mmol) in DMF (2 mL) was treated with MeOH (0.05 mL, 1.23 mmol), DMAP (14 mg, 0.113 mmol), and N-(3-dimethylaminopropyl)-N'-ethylcarbodiimide hydrochloride (240 mg, 1.25 mmol) followed by stirring at RT for 16 h. The reaction mixture was diluted with EtOAc (120 mL), washed with water (2×60 mL) and brine (60 mL), dried over MgSO$_4$, filtered, and concentrated. The residue was purified by column chromatography on silica gel (hexanes/EtOAc, 1:0 to 4:1) to give 11b (20 mg, 39%, $R_f$=0.48, hexanes/EtOAc=4:1) as a clear oil. $^1$H NMR (CHCl$_3$-d): δ 11.45 (s, 1H), 7.86 (s, 1H), 7.44-7.04 (m, 28H), 6.83 (d, J=8.8 Hz, 2H), 5.78 (s, 1H), 4.90-4.46 (m, 6H), 4.44-4.32 (m, 1H), 4.08 (d, J=8.7 Hz, 1H), 3.96-3.60 (m, 2H), 3.80 (s, 3H), 3.75 (s, 3H), 1.12 (s, 3H).

a. A solution of 6d (200 mg, 0.24 mmol, its preparation is described under example 6) in acetonitrile (5.4 mL) and t-BuOH (1.8 mL) was treated with water (1.0 mL) and cooled to about 8° C. The cooled solution was treated with 2-methyl-2-butene (0.2 mL, 1.89 mmol), NaH$_2$PO$_4$ (48 mg, 0.4 mmol), and NaClO$_2$ (240 mg, 80%, 2.12 mmol) followed by stirring at RT for 23 h. Additional NaClO$_2$ (240 mg, 80%, 2.12 mmol) was added and stirring was continued at RT for 42 h. The reaction mixture was diluted with ether (200 mL) and washed with water (50 mL). The aqueous layer was extracted with c. A solution of 11b (20 mg, 0.023 mmol) in MeOH (10 mL) and EtOAc (5 mL) was treated with 1N HCl (aq., 0.69 mL) and Pd/C (10%, 50 mg) followed by hydrogenation at 60 psi for 23 h. The reaction mixture was filtered and filtrate was concentrated. The residue was purified by column chromatography on silica gel (chloroform/CMA 80, 1:0 to 1:1, $R_f$=0.23, chloroform/CMA 80=1:1) to give 11c (3.1 mg, light brown solid, 40%). $^1$H NMR (MeOH-$d_4$): δ 7.94 (s, 1H), 7.34

(s, 1H), 5.56 (s, 1H), 4.00-3.70 (m, 4H), 3.92 (s, 3H), 0.97 (s, 3H); MS (ES⁺): 337.9 (M−H)⁻.

Example 12

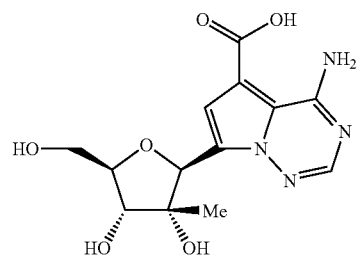 [SMILES: C[C@@]1(O)[C@H](O)[C@@H](CO)O[C@H]1c1cc(C(=O)O)c2c(N)ncnn12]

4-Amino-7-((2S,3R,4R,5R)-3,4-dihydroxy-5-(hydroxymethyl)-3-methyltetrahydrofuran-2-yl)pyrrolo[1,2-f][1,2,4]triazine-5-carboxylic acid (12)

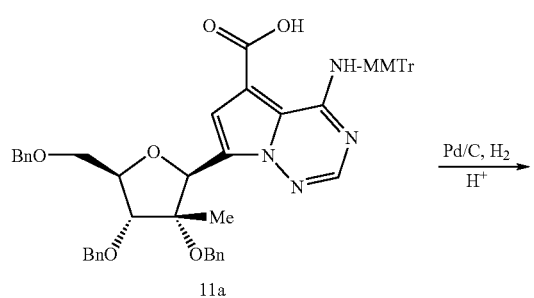

A solution of 11a (77 mg, 0.089 mmol, its preparation is described under example 11) in MeOH (15 mL) was treated with 1N HCl (aq., 0.69 mL) and Pd/C (10%, 50 mg) followed by hydrogenation at 60 psi for 29 h. The reaction mixture was filtered and the filtrate was concentrated. The residue was treated with water (50 mL) and washed with EtOAc (2×25 mL). The aqueous phase was concentrated to dryness and the desired product (12, 12 mg, 42%, yellow solid) was crystallized from MeOH/EtOAc. ¹H NMR (DMSO-d₆): δ 13.28 (s, 1H), 9.59 (s, 1H), 8.49 (s, 1H), 8.07 (s, 1H), 7.30 (s, 1H), 5.37 (s, 1H), 4.10-3.50 (m, 4H), 0.81 (s, 3H); MS (ES⁺): 325.0 (M+H)⁺;

Example 13

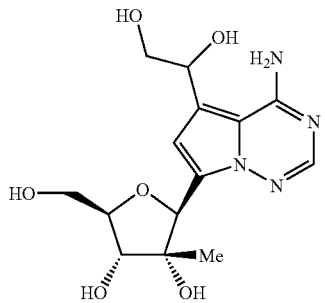 [SMILES: C[C@@]1(O)[C@H](O)[C@@H](CO)O[C@H]1c1cc(C(O)CO)c2c(N)ncnn12]

(2S,3R,4R,5R)-2-(4-Amino-5-(1,2-dihydroxyethyl)pyrrolo[1,2-f][1,2,4]triazin-7-yl)-5-(hydroxymethyl)-3-methyltetrahydrofuran-3,4-diol (13b)

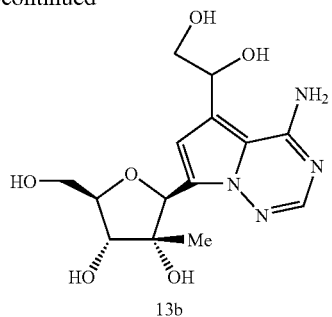

13b a. A solution of 4e (500 mg, 0.58 mmol, its preparation is described under example 4) in acetone/water (9:1, 10 mL) was treated with 4-methylmorpholine N-oxide (140 mg, 97%, 1.16 mmol) and then osmium tetroxide (4% w/v in water, 0.15 mL, 0.024 mmol) followed by stirring at RT for 12 h. The reaction mixture was diluted with water (10 mL) and concentrated to remove acetone only. The aqueous residue was treated with EtOAc (200 mL), washed with water (2×100 mL) and brine (100 mL), dried over MgSO$_4$, filtered, and the filtrate was concentrated. The residue was purified by column chromatography on silica gel (hexanes/EtOAc, 1:0 to 2:1) to give 13a (287 mg, a mixture of diastereoisomers, ratio=1.1/1.0, 55%, R$_f$=0.46, hexanes/EtOAc=2:1) as a clear oil. $^1$H NMR (DMSO-d$_6$): δ 10.02 (s) & 9.95 (s) (1H), 7.28-6.88 (m, 28H), 6.60 (d, J=8.9 Hz, 2H), 6.46 (d, J=3.5 Hz) & 6.39 (d, J=3.8 Hz) (1H), 6.32 (d, J=1.3 Hz, 1H), 5.30 (s, 1H), 4.73-4.61 (m, 2H), 4.02 (d, J=3.0 Hz) & 4.00 (d, J=3.0 Hz) (1H), 3.93-3.86 (m, 1H), 3.49 (s, 3H), 3.48-3.31 (m, 2H), 3.05-2.91 (m, 2H), 1.26 (s, 3H), 1.05 (s, 3H), 0.91 (s) & 0.89 (s) (3H); MS (ES$^-$): 895.3 (M+H)$^+$ b. A solution of 13a (120 mg, 0.13 mmol) in acetonitrile (14 mL) was treated with 1N HCl (aq., 1.4 mL) followed by stirring at RT for 20 h. The reaction mixture was concentrated. The residue was purified by column chromatography on silica gel (chloroform/CMA 80, 1:0 to 0:1, then CMA80/CMA 50 1:1, R$_f$=0.40, CMA 80/CMA 50=1:1) to give 13b (11 mg, a mixture of diastereoisomers, yellow solid, 25%). $^1$H NMR (MeOH-d$_4$): □ 7.77 (s, 1H), 6.75 (s) & 6.74 (s) (1H), 5.55 (s) & 5.54 (s) (1H), 5.02-4.90 (m, 1H), 4.00-3.58 (m, 6H), 0.95 (s, 3H); MS (ES$^+$): 341.1 (M+H)$^+$.

Example 14

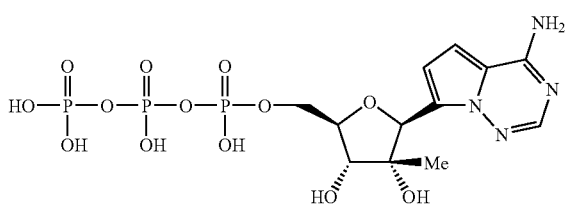 [SMILES: C[C@@]1(O)[C@H](O)[C@@H](COP(=O)(O)OP(=O)(O)OP(=O)(O)O)O[C@H]1c1ccc2c(N)ncnn12]

((2R,3R,4R,5S)-5-(4-Aminopyrrolo[1,2-f][1,2,4]triazin-7-yl)-3,4-dihydroxy-4-methyltetrahydrofuran-2-yl)methyl tetrahydrogen triphosphate (14d)

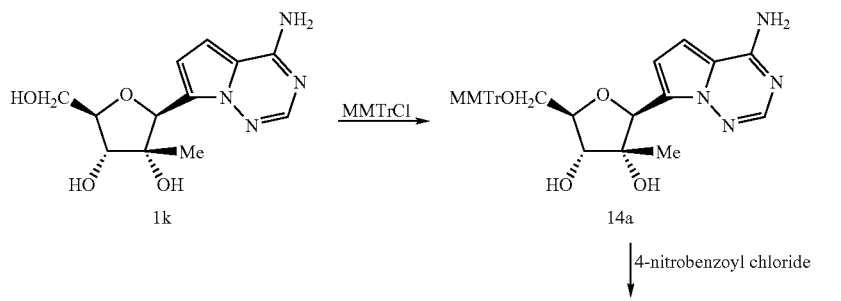

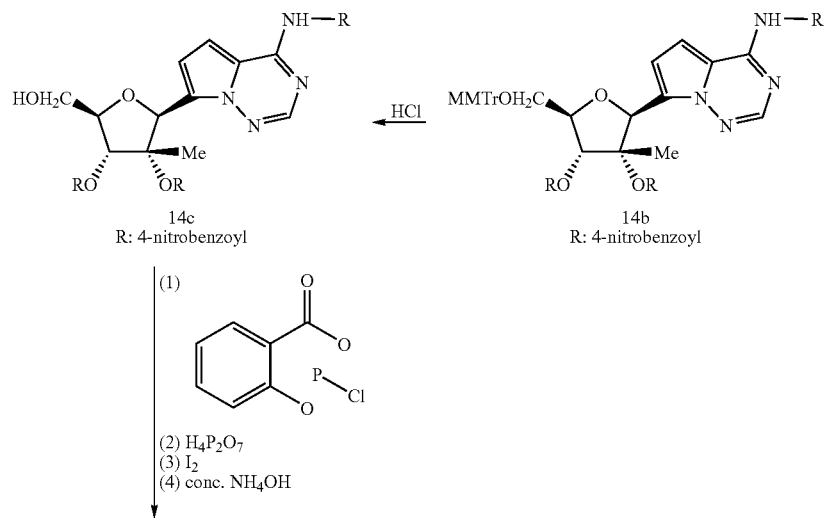

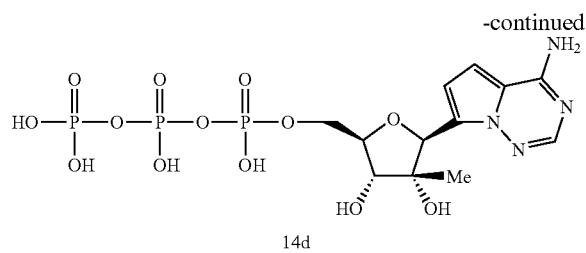

14d a. A suspension of 1k HCl salt (300 mg, 0.95 mmol) in pyridine (9 mL) was treated with DMAP (99%, 30 mg, 0.24 mmol) and MMTrCl (97%, 460 mg, 1.44 mmol) followed by stirring at RT for 15 h. The reaction mixture was diluted with chloroform (150 mL), washed with water (2×60 mL) and dried over $MgSO_4$. After filtration and concentration of the filtrate, the residue was purified by column chromatography on silica gel (hexanes/ethyl acetate, 1:0 to 1:1, then chloroform/CMA 80, 1:0 to 2:1) to give 539 mg of 14a ($R_f$=0.29, chloroform/CMA 80=2/1) as white solid. It was pure enough to be used for the next step. MS ($ES^+$): 575.3 $(M+Na)^+$.

b. A solution of the above 14a (300 mg) in pyridine (20 mL) was treated with DMAP (99%, 35 mg, 0.28 mmol) and 4-nitrobenzoyl chloride (520 mg, 98%, 2.75 mmol) followed by stirring at 70° C. for 14 h. The reaction mixture was diluted with EtOAc (200 mL), washed with water (2×100 mL) and brine (75 mL), dried over $MgSO_4$. After filtration and concentration of the filtrate, the residue was purified by column chromatography on silica gel (hexanes/ethyl acetate, 1:0 to 1:1) to give 14b ($R_f$=0.77, hexanes/ethyl acetate=1/1, 312 mg, 59% for two steps, yellow solid). $^1$H NMR (DMSO-$d_6$): δ 8.44-6.88 (m, 30H), 6.06 (bs, 1H), 5.81 (d, J=3.9 Hz, 1H), 4.50-4.40 (m, 1H), 3.75 (s, 3H), 3.55-3.48 (m, 2H), 1.56 (s, 3H); MS ($ES^-$): 998.8 (M−1).

c. A solution of 14b (276 mg, 0.28 mmol) in $CH_3CN$ (28 mL) was treated with 0.2 N HCl (aq., 1.4 mL) followed by stirring at RT for 2.5 h. The reaction mixture was neutralized with 0.5 N NaOH (aq.) to pH=5 followed by addition of water (40 mL) and concentration under vacuum to remove $CH_3CN$ only. The aqueous residue was extracted with a mixture of $CHCl_3$/MeOH (5:1, 100 mL, 50 mL). The combined organic extracts were dried over $MgSO_4$. After filtration and concentration of the filtrate, the residue was purified by column chromatography on silica gel (hexanes/ethyl acetate, 1:0 to 1:1) to give 14c ($R_f$=0.58, hexanes/ethyl acetate=1/1, 150 mg, 74%) as a yellow solid. $^1$H NMR (DMSO-$d_6$): 8.81-7.80 (m, 14H), 7.32 (bs, 1H), 7.12 (bs, 1H), 6.02 (bs, 1H), 5.73 (d, J=3.4 Hz, 1H), 5.26 (t, 1H), 4.32-4.25 (m, 1H), 3.90-3.80 (m, 2H), 1.52 (s, 3H); MS ($ES^+$): 728.2 $(M+H)^+$. Anal. Calcd for $C_{33}H_{25}N_7O_{13}$.0.25 EtOAc: C, 54.48; H, 3.63; N, 13.08. Found: C, 54.72; H, 3.84; N, 12.71.

d. A suspension of 14c (50 mg, 0.069 mmol) in a mixture of pyridine (70 µL) and dioxane (210 µL) was treated with a freshly prepared solution of chloro-4H-1,3,2-benzodioxaphosphorin-4-one (1M in dioxane, 80 µL). The reaction mixture was stirred at room temperature for 20 min followed by treatment with a solution of tributylammonium pyrophosphate (1.6 $Bu_3N.1.0H_4P_2O_7$, 50 mg, 0.11 mmol) in DMF (220 µL) and tri-n-butylamine (70 µL) simultaneously. The clear solution formed was stirred at room temperature for 30 min followed by treatment with 2.9 mL of 1% $I_2$ in Py/$H_2O$ (98/2). Excess iodine was reduced by 5% aqueous sodium thiosulphate (200 µL) and the resulting solution was concentrated to dryness. The residue was treated with conc. $NH_4OH$ (15 mL) and stirred at room temperature overnight followed by concentration to dryness. The residue was dissolved in $H_2O$ (20 mL) and washed with $CH_2Cl_2$ (2×15 mL). The aqueous phase was concentrated under vacuum for a short period of time to remove the trace of $CH_2Cl_2$ and purified by DEAE ion exchange column chromatography with a linear gradient of TEAB buffer (1M TEAB buffer, pH=8.0/$H_2O$, 0:1 to 1:0, total: 500 mL). The fractions containing the desired nucleotide was combined and concentrated. The residue was re-dissolved in $H_2O$ and purified further by HPLC ($CH_3CN$/0.1 M TEAB buffer, pH=8.0, 0-20 min, 0-35% $CH_3CN$; monitoring at 244 nm) to give 14d ($t_R$=17.00 min). Fractions containing 14d were concentrated and re-dissolved in 3 mL of $H_2O$ and the concentration of 14d was measured to be 4.1 mM (yield: 18%) by UV (244 nm, ε=35,000 $M^{-1}$ $cm^{-1}$). $^1$H NMR ($D_2O$): δ 7.77 (bs, 1H), 6.93 (d, J=4.0 Hz, 1H), 6.85 (d, 1H), 5.45 (s, 1H), 4.34-4.10 (m, 2H), 4.10-3.96 (m, 2H), 0.78 (s, 3H); $^{31}$P NMR ($D_2O$): δ −9.25 (d, J=17.8 Hz, 1P), −9.78 (d, J=17.9 Hz, 1P), −21.70 (m, 1P); MS ($ES^-$): 519.1 (M−1)

Example 15

The following illustrate representative pharmaceutical dosage forms, containing a compound of Formula I, or a pharmaceutically acceptable salt or prodrug thereof ('Compound X'), for therapeutic or prophylactic use in humans.

| (i) Tablet 1 | mg/tablet |
|---|---|
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X = | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| Compound X = (free acid form) | 1.0 |
| Dibasic sodium phosphate | 12.0 |
| Monobasic sodium phosphate | 0.7 |
| Sodium chloride | 4.5 |
| 1.0 N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| Compound X = (free acid form) | 10.0 |
| Monobasic sodium phosphate | 0.3 |
| Dibasic sodium phosphate | 1.1 |
| Polyethylene glycol 400 | 200.0 |
| 01 N Sodium hydroxide solution (pH adjustment to 7.0-7.5) | q.s. |
| Water for injection | q.s. ad 1 mL |

| (vi) Aerosol | mg/can |
|---|---|
| Compound X = | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed:

1. A compound of formula (11):

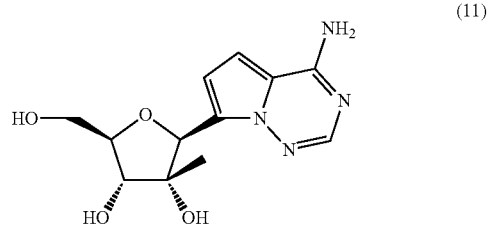 [SMILES: C[C@@]1(O)[C@H](O)[C@@H](CO)O[C@H]1c1ccc2c(N)ncnn12]

(11)

or a pharmaceutically acceptable salt thereof.

* * * * *